(12) United States Patent
Quik et al.

(10) Patent No.: US 7,718,677 B2
(45) Date of Patent: May 18, 2010

(54) METHODS AND COMPOSITIONS FOR REDUCTION OF SIDE EFFECTS OF THERAPEUTIC TREATMENTS

(75) Inventors: Maryka Quik, Palo Alto, CA (US); Donato Di Monte, Cupertino, CA (US); J. William Langston, Los Altos Hills, CA (US)

(73) Assignee: Parkinson's Institute, Sunnyvale, CA (US)

( * ) Notice: Subject to any disclaimer, the term of this patent is extended or adjusted under 35 U.S.C. 154(b) by 34 days.

(21) Appl. No.: 12/061,587

(22) Filed: Apr. 2, 2008

(65) Prior Publication Data
US 2008/0260825 A1    Oct. 23, 2008

Related U.S. Application Data

(60) Provisional application No. 60/909,637, filed on Apr. 2, 2007, provisional application No. 60/956,296, filed on Aug. 16, 2007, provisional application No. 60/956,657, filed on Aug. 17, 2007.

(51) Int. Cl.
*A61K 31/44* (2006.01)
*A61K 31/195* (2006.01)

(52) U.S. Cl. .................... 514/343; 514/567

(58) Field of Classification Search ............. None
See application file for complete search history.

(56) References Cited

U.S. PATENT DOCUMENTS

| | | | |
|---|---|---|---|
| 5,069,904 A | 12/1991 | Masterson | |
| 5,212,188 A | 5/1993 | Caldwell et al. | |
| 5,227,391 A | 7/1993 | Caldwell et al. | |
| 5,232,933 A | 8/1993 | Lippiello et al. | |
| 5,242,934 A | 9/1993 | Lippiello et al. | |
| 5,248,690 A | 9/1993 | Caldwell et al. | |
| 5,662,920 A | 9/1997 | Santus | |
| 6,034,079 A | 3/2000 | Sanberg et al. | |
| 6,211,194 B1 * | 4/2001 | Westman et al. | 514/300 |
| 6,238,689 B1 | 5/2001 | Rhodes et al. | |
| 6,274,606 B1 | 8/2001 | Caldwell et al. | |
| 6,310,102 B1 | 10/2001 | Dull et al. | |
| 6,417,359 B1 | 7/2002 | Crooks et al. | |
| 6,492,399 B1 | 12/2002 | Dull et al. | |
| 6,900,202 B2 | 5/2005 | Imoto et al. | |
| 6,911,475 B1 * | 6/2005 | Cesaro et al. | 514/567 |
| 6,998,176 B2 | 2/2006 | Morita et al. | |
| 7,064,143 B1 | 6/2006 | Gurley et al. | |
| 2002/0002189 A1 | 1/2002 | Smith et al. | |
| 2003/0087937 A1 | 5/2003 | Lindberg | |
| 2003/0119879 A1 | 6/2003 | Landh et al. | |
| 2004/0034068 A1 | 2/2004 | Warchol et al. | |
| 2004/0191322 A1 | 9/2004 | Hansson | |
| 2004/0194793 A1 | 10/2004 | Lindell et al. | |
| 2004/0229908 A1 | 11/2004 | Nelson | |
| 2005/0014779 A1 | 1/2005 | Papke | |
| 2005/0245595 A1 | 11/2005 | Gurley et al. | |
| 2006/0167039 A1 | 7/2006 | Nguyen et al. | |
| 2007/0026054 A1 | 2/2007 | Theobald et al. | |
| 2007/0163610 A1 | 7/2007 | Lindell et al. | |
| 2007/0179172 A1 | 8/2007 | Becker et al. | |

FOREIGN PATENT DOCUMENTS

| | | |
|---|---|---|
| WO | WO 97/34605 A1 | 9/1997 |
| WO | WO 99/66916 A1 | 12/1999 |
| WO | WO 00/35279 A1 | 6/2000 |
| WO | WO 01/15696 A1 | 3/2001 |
| WO | WO 02/076211 A1 | 10/2002 |
| WO | WO 03/026655 A1 | 4/2003 |
| WO | WO 2003/055486 A1 | 7/2003 |
| WO | WO 2003/061656 A1 | 7/2003 |
| WO | WO 2004/098600 A1 | 11/2004 |
| WO | WO2005/018619 A1 | 3/2005 |
| WO | WO 2006/069097 A2 | 6/2006 |
| WO | WO 2006/069097 A3 | 6/2006 |
| WO | WO 2007/104575 A2 | 9/2007 |
| WO | WO 2007/133141 A1 | 11/2007 |
| WO | WO 2007/104575 A3 | 1/2008 |

OTHER PUBLICATIONS

Ahlskog and Muenter, 2001. Frequency of Levodopa-related dyskinesias and motor fluctuation as estimated from the cumulative literature. Movement Disorders, vol. 16(3):448-458 (provided on the May 8, 2008 IDS).*

Petzinger et al, 2001. Reliability and validity of a new global dyskinesia rating scale in the MPTP-lesioned non-human primate. Movement Disorders, vol. 16(2):202-207 (provided on the May 8, 2008 IDS).*

(Continued)

*Primary Examiner*—Jean C. Witz
*Assistant Examiner*—Raymond P Yeager
(74) *Attorney, Agent, or Firm*—Wilson Sonsini, Goodrich & Rosati

(57) ABSTRACT

The invention provides compositions and methods utilizing a nicotinic receptor modulator, e.g., to reduce or eliminate a side effect associated with dopaminergic agent treatment. In some embodiments, the invention provides compositions and methods utilizing a combination of a dopaminergic agent and a nicotinic receptor modulator that reduces or eliminates a side effect associated with dopaminergic agent treatment.

22 Claims, 16 Drawing Sheets

OTHER PUBLICATIONS

Quik et al, 2004. Smoking, nicotine, and Parkinson's disease. TRENDS in Neurosciences, vol. 27(9):561-568 (provided on the May 8, 2008 IDS).*
Quik and Kulak, 2002. Nicotine and nicotinic receptors; relevance to parkinson's disease. NeuroToxicology, vol. 23:581-594 (provided on the May 8, 2008 IDS).*
Domino et al, 1999. Nicotine alone and in combination with L-DOPA methyl ester or the D2 agonist N-0923 in MPTP-induced chronic hemiparkinsonian monkeys. Experimental Neurobiology, vol. 158:414-421 (provided on the May 8, 2008 IDS).*
NINDS Website: Parkinson's Disease. http://www.ninds.nih.gov/disorders/parkinsons_disease/detail_parkinsons_disease.htm (provided on the Jan. 28, 2008 IDS).*
Schneider et al, 1998. Effects of SIB-1508Y, a novel neuronal nicotinic acetylcholine receptor agonist, on motor behavior in Parkonsonian monkeys. Movement Disorders, vol. 13(4):637-642 (provided on the May 8, 2008 IDS).*
De La Fuente-Fernández, et al. The placebo effect in Parkinson's disease. Trends Neurosci. 2002; 25(6):302-6.
Meredith, et al. Behavioral models of Parkinson's disease in rodents: a new look at an old problem. Mov Disord. 2006; 21(10):1595-1606.
Quik, et al. Nicotine and Parkinson's disease: implications for therapy. Mov Disord. 2008; 23(12):1641-52.
Quik, et al. Nicotine neuroprotection against nigrostriatal damage: importance of the animal model. Trends Pharmacol Sci. 2007; 28(5):229-35.
National Institute of Neurological Disorders and Stroke. Parkinson's Disease: Hope Through Reasearch. Available at http://www.ninds.nih.gov/disorders/parkinsons_disease/detail_parkinsons_disease.htm. Accessed Jan. 14, 2009, Ninds Publication 06-139; Publication date Jan. 2006.
Ahlskog, et al. Frequency of levodopa-related dyskinesias and motor fluctuations as estimated from the cumulative literature. Movement Disorders. 2001; 16(3): 448-58.
Angulo, et al. Oral nicotine in treatment of primary sclerosing cholangitis: a pilot study. Dig Dis Sci. Mar. 1999;44(3):602-7.
Bordia, et al. Partial recovery of striatal nicotinic receptors in 1-methyl-4-phenyl-1,2,3,6-tetrahydropyridine (MPTP)-lesioned monkeys with chronic oral nicotinic. The Journal of Pharmacology and Experimental Therapeutics. 2006; 319(1): 285-92.
Bové, et al. Toxin-induced models of Parkinson's disease. NeuroRx. 2005; 2(3): 484-94.
Brotchie, et al. Levodopa-induced dyskinesia in Parkinson's disease. Journal of Neural Transmission. 2005; 112: 359-91.
Chen, et al. Enhanced striatal opioid receptor-mediated G-protein activation in L-DOPA-treated dyskinetic monkeys. Neuroscience. 2005; 132: 409-20.
Di Monte, et al. Relationship among nigrostriatal denervation, parkinsonism, and dyskinesias in the MPTP primate model. Movement Disorders. 2000; 15(3): 459-66.
Domino, et al. Nicotine alone and in combination with L-DOPA methyl ester or the D2 agonist N-0923 in MPTP-induced chronic hemiparkinsonian monkeys. Experimental Neurology. 1999; 158: 414-21.
Ebersbach, et al. Worsening of motor performance in patients with Parkinson's disease following transdermal nicotine administration. Movement Disorders. 1999; 14(6): 1011-13.
Gatto, et al. TC-1734: An orally active neuronal nicotinic acetylcholine receptor modulator with antidepressant, neuroprotective and long-lasting cognitive effects. CNS Drug Rev. 2004; 10(2): 147-66.
Green, et al. An oral formulation of nicotine for release and absorption in the colon: its development and pharmacokinetics. Br J Clin Pharmacol. Oct. 1999;48(4):485-93.
He, et al. Autoradiographic analysis of dopamine receptor-stimulated [35S]GTPγS binding in rat striatum. Brain Research. 2000; 885: 133-6.
He, et al. Autoradiographic analysis of N-methyl-D-aspartate receptor binding in monkey brain: Effects of 1-methyl-4-phenyl-1,2,3,6-tetrahydropyridine and levodopa treatment. Neuroscience. 2000; 99(4): 697-704.

Hsu, et al. Effect of the D3 dopamine receptor partial agonist BP897 [N-[4-(4-(2-methoxyphenyl)piperazinyl)butyl]-2-napthamide] on L-3,4-dihydroxyphenylalanine-induced dyskinesias and parkinsonism in squirrel monkeys. The Journal of Pharmacology and Experimental Therapeutics. 2004; 311(2): 770-7.
Ingram, et al. Preliminary observations of oral nicotine therapy for inflammatory bowel disease: an open-label phase I-II study of tolerance. Inflamm Bowel Dis. Dec. 2005;11(12):1092-6.
Jeyarasasingam, et al. Nitric oxide is involved in acetylcholinesterase inhibitor-induced myopathy in rats. The Journal of Pharmacology and Experimental Therapeutics. 2000; 295(1): 314-20.
Jeyarasasingam, et al. Stimulation of non-α7 nicotinic receptors partially protects dopaminergic neurons from 1-methyl-4-phenylpyridinium-induced toxicity in culture. Neuroscience. 2002; 109(2): 275-85.
Jeyarasasingam, et al. Tacrine, a reversible acetylcholinesterase inhibitor, induces myopathy. Neuroreport. 2000; 11(6): 1173-6.
Kelton, et al. The effects of nicotine on Parkinson's disease. Brain Cogn. 2000; 43(1-3): 274-82.
Kulak, et al. 5-Iodo-A-85380 binds to α-conotoxin MII-sensitive nicotinic acetylcholine receptors (nAChRs) as well as α4β2*. subtypes. J. Neurochem. 2002; 81: 403-6.
Kulak, et al. Declines in different β2* nicotinic receptor populations in monkey striatum after nigrostriatal damage. The Journal of Pharmacology and Experimental Therapeutics. 2002; 303(2): 633-39.
Kulak, et al. Loss of nicotinic receptors in monkey striatum after 1-methyl-4-phenyl-1,2,3,6-tetrahydropyridine treatment is due to a decline in α-conotoxin MII sites. Molecular Pharmacology. 2002; 61(1): 230-8.
Lai, et al. Long-term nicotine treatment decreases striatal α6* nicotinic acetylcholine receptor sites and function in mice. Molecular Pharmacology. 2005; 67(5): 1639-47.
Lai, et al. Selective recovery of striatal 125I-α-conotoxinMII nicotinic receptors after nigrostriatal damage in monkeys. Neuroscience. 2004; 127: 399-408.
Langston, et al. Investigating levodopa-induced dyskinesias in the parkinsonian primate. Ann. Neurol. 2000; 47(4 Suppl 1): S79-89.
Lemay, et al. Lack of efficacy of a nicotine transdermal treatment on motor and cognitive deficits in Parkinson's disease. Prog. Neuropsychopharmacol. Biol. Psychiatry. 2004; 28(1): 31-9.
Linazasoro, G. New ideas on the origin of L-DOPA-induced dyskinesias: Age, genes and neural plasticity. Trends Pharmacol. Sci. 2005; 26(8): 391-7.
Matta, et al. Guidelines on nicotine dose selection for in vivo research. Psychopharmacology (Berl.). 2007; 190(3): 269-319.
McCallum, et al. Compensation in pre-synaptic dopaminergic function following nigrostriatal damage in primates. Journal of Neurochemistry. 2006; 96: 960-72.
McCallum, et al. Decrease in α3*/α6* nicotinic receptors in monkey brain after nigrostriatal damage. Molecular Pharmacology. 2005; 68(3): 737-46.
McCallum, et al. Differential regulation of mesolimbic α3*/α6β2* and α4β2* nicotinic acetylcholine receptor sites and function after long-term oral nicotine to monkeys. The Journal of Pharmacology and Experimental Therapeutics. 2006; 318(1): 381-8.
Mccallum, et al. Increases in α4* but not α3*/α6* nicotinic receptor sites and function in the primate striatum following chronic oral nicotine treatment. Journal of Neurochemistry. 2006; 96: 1028-41.
Meshul, et al. Nicotine alters striatal glutamate function and decreases the apomorphine-induced contralateral rotations in 6-OHDA-lesioned rats. Experimental Neurology. 2002; 175: 257-74.
Olanow, C. The scientific basis for the current treatment of Parkinson's disease. Annu. Rev. Med. 2004; 55: 41-60.
O'Neill, et al. The role of neuronal nicotinic acetylcholine receptors in acute and chronic neurodegeneration. Curr. Drug Targets CNS Disord. 2002; 1(4): 399-411.
Petzinger, et al. Reliability and validity of a new global dyskinesia rating scale in the MPTP-lesioned non-human primate. Movement Disorders. 2001; 16(2): 202-7.
Quik, et al. Chronic oral nicotine normalizes dopaminergic function and synaptic plasticity in 1-methyl-4-phenyl-1,2,3,6-tetrahydropyridine-lesioned primates. The Journal of Neuroscience. 2006; 26(17): 4681-89.

Quik, et al. Chronic oral nicotine treatment protects against striatal degeneration in MPTP-treated primates. Journal of Neurochemistry. 2006; 98(6): 1866-75.

Quik, et al. Differential alterations in nicotinic receptor α6 and β3 subunit messenger RNAs in monkey substantia nigra after nigrostriatal degeneration. Neuroscience. 2000; 100(1): 63-72.

Quik, et al. Differential declines in striatal nicotinic receptor subtype function after nigrostriatal damage in mice. Molecular Pharmacology. 2003; 63(5): 1169-79.

Quik, et al. Differential nicotinic receptor expression in monkey basal ganglia: Effects of nigrostriatal damage. Neuroscience. 2002; 112(3): 619-630.

Quik, et al. Expression of D3 receptor messenger RNA and binding sites in monkey striatum and substantia nigra after nigrostriatal degeneration: Effect of levodopa treatment. Neuroscience. 2000; 98(2): 263-73.

Quik, et al. Increases in striatal preproenkephalin gene expression are associated with nigrostriatal damage but not L-DOPA-induced dyskinesias in the squirrel monkey. Neuroscience. 2002; 113(1): 213-20.

Quik, et al. L-DOPA treatment modulates nicotinic receptors in monkey striatum. Molecular Pharmacology. 2003; 64(3): 619-28.

Quik, et al. Localization of nicotinic receptor subunit mRNAs in monkey brain by in situ hybridization. The Journal of Comparative Neurology. 2000; 425: 58-69.

Quik, et al. Loss of α-conotoxinMII- and A85380-sensitive nicotinic receptors in Parkinson's disease striatum. Journal of Neurochemistry. 2004; 88: 668-79.

Quik, et al. Nicotine administration reduces striatal MPP+ levels in mice. Brain Research. 2001; 917: 219-24.

Quik, et al. Nicotine and nicotinic receptors; relevance to Parkinson's disease. NeuroToxicology. 2002; 23: 581-94.

Quik, et al. Nicotinic receptors and Parkinson's disease. European Journal of Pharmacology. 2000; 393: 223-30.

Quik, et al. Striatal α6* nicotinic acetylcholine receptors: Potential targets for Parkinson's disease therapy. The Journal of Pharmacology and Experimental Therapeutics. 2006; 316(2): 481-9.

Quik, et al. Subunit composition of nicotinic receptors in monkey striatum: Effect of treatments with 1-methyl-4-phenyl-1,2,3,6-tetrahydropyridine or L-DOPA. Molecular Pharmacology. 2005; 67(1): 32-41.

Quik, et al. Vulnerability of 125I-α-conotoxin MII binding sites to nigrostriatal damage in monkey. The Journal of Neuroscience. 2001; 21(15): 5494-500.

Quik, M. Smoking, nicotine and Parkinson's disease. Trends Neurosci. 2004; 27(9): 561-8.

Rueter, et al. ABT-089: Pharmacological properties of a neuronal nicotinic acetylcholine receptor agonist for the potential treatment of cognitive disorders. CNS Drug Rev. 2004; 10(2): 167-82.

Samii, et al. Parkinson's disease. The Lancet. 2004; 363: 1783-93.

Savitt, et al. Diagnosis and treatment of Parkinson disease: molecules to medicine. The Journal of Clinical Investigation. 2006; 116(7): 1744-54.

Schapira, A. Disease modification in Parkinson's disease. Lancet Neurol. 2004; 3(6): 362-8.

Schneider, et al. Effects of SIB-1508Y, a novel neuronal nictonic acetylcholine receptor agonist, on motor behavior in parkinsonian monkeys. Movement Disorders. 1998; 13(4): 637-42.

Schneider, et al. Effects of the nicotinic acetylcholine receptor agonist SIB-1508Y on object retrieval performance in MPTP-treated monkeys: Comparison with levodopa treatment. Ann. Neurol. 1998; 43: 311-17.

Schober, et al. Classic toxin-induced animal models of Parkinson's disease: 6-OHDA and MPTP. Cell Tissue Res. 2004; 318: 215-24.

Togasaki, et al. Dyskinesias in normal squirrel monkeys induced by nomifensine and levodopa. Neuropharmacology. 2005; 48(3): 398-405.

Togasaki, et al. Levodopa induces dyskinesias in normal squirrel monkeys. Ann. Neurol. 2001; 50: 254-7.

Togasaki, et al. The Webcam system: A simple, automated, computer-based video system for quantitative measurement of movement of nonhuman primates. Journal of Neuroscience Methods. 2005; 145: 159-66.

Vieregge, et al. Transdermal nicotine in PD: A randomized, double-blind, placebo-controlled study. Neurology. 2001; 57(6): 1032-5.

Westman, et al. Oral nicotine solution for smoking cessation: a pilot tolerability study. Nicotine Tob Res. Nov. 2001;3(4):391-6.

Meshul, et al. Nicotine Affects Striatal Glutamatergic Function in 6-OHDA Lesioned Rats. Advanced in behavioural Biology. Basal Ganglia VI. 2003; 547: 589-598.

Quik, et al. Nicotine reduces levodopa-induced dyskinesias in lesioned monkeys. Ann Neurol. 2007; 62(6):588-96.

Davie, C. A review of Parkinson's disease. British Medical Bulletin 2008 86(1):109-127.

Stocchi, et al. Motor fluctuations in levodopa treatment: clinical pharmacology. Eur Neurol. 1996;36 Suppl 1:38-42.

* cited by examiner

METHODS AND COMPOSITIONS FOR REDUCTION OF SIDE EFFECTS OF THERAPEUTIC TREATMENTS

CROSS REFERENCE

This application claims the benefit of provisional applications 60/909,637 entitled Methods and Compositions for Reduction of Side Effects of Therapeutic Treatments filed Apr. 2, 2007; 60/956,296 entitled Methods and Compositions for Reduction of Side Effects of Therapeutic Treatments filed Aug. 16, 2007; and 60/956,657 entitled Methods and Compositions for Reduction of Side Effects of Therapeutic Treatments filed Aug. 17, 2007.

GOVERNMENT INTERESTS

Certain embodiments of the present invention were made under research grant numbers NIH NS34886 and NS 42091 from the National Institute of Health, who may have certain rights thereto.

BACKGROUND OF THE INVENTION

Many of the leading treatments for diseases lead to undesired side effects. For instance, levodopa, the standard for Parkinson's disease treatment, is associated with debilitating abnormal involuntary movements or dyskinesias. These motor abnormalities may occur after only a few months of treatment and affect the majority of patients within 5-20 years. They can be quite incapacitating and represent a major complication in Parkinson's disease management. Currently there are only limited therapeutic options for dyskinesias.

Parkinson's disease is extremely common amongst those over 65, and age group that, in North America, is predicted to rise from 12% to 24% over the next 30 year. The overall prevalence of Parkinson's disease in this population is in the order of 1.5-2% and increases with age. Therefore, additional treatments are needed for this disabling complication of levodopa therapy.

SUMMARY OF THE INVENTION

The invention provides methods, compositions, and kits for the use of nicotinic receptor modulator. For example the methods, compositions, and kits described herein are used to reduce or eliminate a side effect. In some embodiments, the methods, compositions, and kits described herein are used to reduce or eliminate a side effect of a dopaminergic agent.

In one aspect, the invention provides compositions including a nicotinic receptor modulator. In some embodiments of this aspect, the invention provides a pharmaceutical composition including a nicotinic receptor modulator. In some embodiments, the invention includes pharmaceutical compositions where the nicotinic receptor modulator is present in an amount sufficient to decrease a side effect of a dopaminergic agent when the composition is administered to an animal. In some embodiments, the invention includes pharmaceutical compositions where the nicotinic receptor modulator is present in an amount sufficient to reduce or eliminate a side effect of a dopaminergic agent and to prevent or reduce the likelihood of addiction to the nicotinic receptor modulator when the composition is administered to an animal. The pharmaceutical compositions including a nicotinic receptor modulator are administered through various routes of delivery further described herein. In some embodiments, the pharmaceutical compositions including a nicotinic receptor modulator are administered orally to an animal. In some embodiments, the invention provides a solid pharmaceutical composition for oral administration containing an effective amount of a nicotinic receptor modulator and a pharmaceutical excipient suitable for oral administration. In some embodiments, the invention provides a liquid pharmaceutical composition for oral administration containing an effective amount of a nicotinic receptor modulator and a pharmaceutical excipient suitable for oral administration.

In some embodiments of this aspect, the invention provides a pharmaceutical composition including a dopaminergic agent and nicotinic receptor modulator. In some embodiments, the invention includes pharmaceutical compositions where the nicotinic receptor modulator is present in an amount sufficient to decrease a side effect of the dopaminergic agent when the composition is administered to an animal.

In some embodiments of this aspect, the nicotinic receptor modulator modulates a nicotinic receptor in the brain. In some embodiments, the nicotinic receptor modulator modulates a nicotinic receptor in the striatum or substantia niagra. In some embodiments, the nicotinic receptor modulator modulates a nicotinic receptor comprising at least one sub-unit or a nicotinic receptor containing at least one α subunit and at least one β subunit. In some embodiments, the αsubunit is selected from the group consisting of α2, α3, α4, α5, α6, α7, α8, α9, and α10 and the β subunit is selected from the group consisting of β2, β3 and β4. In some embodiments, the nicotinic receptor modulator modulates a nicotinic receptor comprising subunits selected from the group consisting of α4β2, α6β2, α4α6β2, α4α5β α4α6β2β3, α6β2β3 and α4α2β2.

In some embodiments of the composition, the nicotinic receptor modulator in the composition includes a nicotinic receptor agonist. In some embodiments, the nicotinic receptor agonist in the composition is selected from the group consisting of a simple or complex organic or inorganic molecule, a peptide, a protein, an oligonucleotide, an antibody, an antibody derivative, an antibody fragment, a vitamin derivative, a carbohydrate, and a toxin. Examples of nicotinic receptor agonists include, but are not limited to, nicotine, conotoxinMII, epibatidine, A-85380, cytisine, lobeline, anabasine, SIB-1508Y, SIB-1553A, ABT-418, ABT-594, ABT-894, TC-2403, TC-2559, RJR-2403, SSR180711, GTS-21 and varenicline. In some embodiments, the agonist is nicotine.

In some embodiments of the composition, the dopaminergic agent is a dopamine precursor or a dopamine receptor agonist. Examples of dopaminergic agents include, but are not limited to, levodopa, bromocriptine, pergolide, pramipexole, cabergoline, ropinorole, apomorphine or a combination thereof. In some embodiments, the dopaminergic agent is levodopa.

In some embodiments of the compositions of the invention, the side effect being treated includes tremors, headache, changes in motor function, changes in mental status, changes in sensory functions, seizures, insomnia, paresthesia, dizziness, coma and dyskinesias. In some embodiments, the side effect is dyskinesias. In some embodiments of the compositions of the invention, the side effects are decreased at least 30% compared to the side effects without the nicotinic receptor modulator. In some embodiments of the invention, the therapeutic effect of dopaminergic agent is increased an average of at least about 5% compared to the therapeutic effect without the nicotinic receptor modulator, when the composition is administered to an animal.

In some embodiments of the compositions of the invention, the nicotinic receptor modulator is administered to an animal suffering or about to suffer from a dopaminergic agent-induced side effect such that the nicotinic receptor modulator or a metabolite reaches an optimal concentration in the blood, plasma and/or target tissues in the animal so the side effect can be decreased. In some embodiments the nicotinic receptor modulator or a metabolite is in the bloodstream of the animal prior to the dopaminergic agent. In some embodiments, the nicotinic receptor modulator or a metabolite is in the bloodstream of the animal after the dopaminergic agent but prior to the beginning of the dopaminergic agent-induced side effect. In some embodiments, the nicotinic receptor modulator or a metabolite is in the bloodstream of the animal after the dopaminergic agent and after the animal is showing the first signs of a dopaminergic agent-induced side effect. In some embodiments, the nicotinic receptor modulator or a metabolite is in the bloodstream of the animal after the dopaminergic agent and after the animal is suffering of a dopaminergic agent-induced side effect.

In some embodiments, the nicotinic receptor modulator is administered through pulsatile delivery. In some embodiments, the nicotinic receptor modulator is administered in an extended release or controlled release formulation. In some embodiments, the nicotinic receptor modulator and/or the dopaminergic agent are administered in a multilayer tablet.

In some embodiments of the compositions of the invention, a pharmaceutical composition includes the composition of the invention and a pharmaceutically acceptable excipient. In some embodiments of the composition, a molar ratio of the dopaminergic agent and the nicotinic receptor modulator is about 0.001:1 to about 10:1. In some embodiments of the composition, the dopaminergic agent is present in an amount of about 0.1 to about 1000 mg and the nicotinic receptor modulator is present in an amount of about 0.1 to about 2000 mg. In some embodiments, the nicotinic receptor modulator is nicotine. In some embodiments, nicotine is present at about 0.1 to about 100 mg. In some embodiments, nicotine is present at about 0.1 to about 10 mg. In some embodiments, nicotine is present at about 0.5 mg. In some embodiments of the compositions of the invention, a pharmaceutical composition includes an effective amount of levodopa and an amount of nicotine sufficient to reduce levodopa induced-dyskinesias and a pharmaceutically acceptable carrier.

In some embodiments, a pharmaceutical composition includes a third agent also used for the treatment of a side effect of the dopaminergic agent. In some embodiments, the side effect treated with the nicotinic receptor modulator and the third agent is the same side effect. In some embodiments, the side effects treated with the nicotinic receptor modulator and the third agent are different side effects. In some embodiments, the third agent is amantadine. In some embodiments, the pharmaceutical compositions of the invention include one or more agents used in the art in combination with a dopamine agent treatment to achieve a therapeutic effect. For instance, in some embodiments, the pharmaceutical compositions of the invention include an agent such as carbidopa, which blocks the conversion of levodopa to dopamine in the blood. In some embodiments, the pharmaceutical compositions of the invention include a COMT Inhibitors, such as entacapone. In some embodiments, the pharmaceutical compositions of the invention include a monoamine oxidase type B (MAO-B) inhibitor such as selegiline.

In some embodiments of the compositions of the inventions, a pharmaceutical composition includes an effective amount of levodopa, an effective amount of carbidopa, an effective amount of nicotine capable of reducing levodopa-induced dyskinesias and a pharmaceutically acceptable carrier.

In some embodiments of the compositions of the inventions, a pharmaceutical composition includes an effective amount of a dopaminergic agent, an effective amount of nicotine and a pharmaceutically acceptable carrier, where nicotine is present at about 0.01 to about 10 mg.

In some embodiments of the compositions of the inventions, a solid pharmaceutical composition for oral administration includes nicotine and a pharmaceutically acceptable carrier, where nicotine is present at about 0.01 mg to about 2.8 mg. In some embodiments of the compositions of the invention, the amount of nicotine present is less than 3 mg.

In some embodiments of the compositions of the inventions, a multilayer tablet includes an immediate release layer and a sustained release layer, where the immediate release layer comprises one or more therapeutic agents independently selected from the group consisting of nicotinic receptor agonist and dopaminergic agent, and the sustained release layer comprises one or more therapeutic agents independently selected from the group consisting of nicotinic receptor agonist and dopaminergic agents. In some embodiments, the immediate release layer or the sustained release agent further comprises a third agent. In some embodiments, the third agent is used to achieve a therapeutic effect in combination with the dopaminergic agent or to treat a side effect of the dopaminergic agent.

In some embodiments of the invention, a kit includes the composition of the invention and instructions for use of the composition.

In another aspect, the invention provides methods utilizing nicotinic receptor agonist. In some embodiments of this aspect, the invention provides a method of treating an animal by administering to an animal an effective amount of a nicotinic receptor agonist sufficient to reduce or eliminate a side effect of a dopaminergic agent. In some embodiments of this aspect, the invention provides a method of treating an animal by administering to an animal an effective amount of a nicotinic receptor agonist sufficient to reduce or eliminate a side effect of a dopaminergic agent and to prevent or reduce the likelihood of addiction to the nicotinic receptor modulator when the composition is administered to an animal. In some embodiments, the nicotinic receptor modulator is administered through various routes of delivery further described herein. In one embodiment, the nicotinic receptor modulator is administered orally to an animal.

In some embodiments of this aspect, the invention provides a method of treating a condition by administering to an animal suffering from the condition an effective amount of a dopaminergic agent and an amount of a nicotinic receptor agonist sufficient to reduce or eliminate a side effect of the dopaminergic agent. In some embodiments, the agonist reduces or eliminates a plurality of side effects of the dopaminergic agent. In some embodiments, the dopaminergic agent and the nicotinic receptor agonist are administered in a single composition. In some embodiments, the dopaminergic agent and the nicotinic receptor agonist are admixed in the composition.

In some embodiments of this aspect, the invention provides a method of decreasing a side effect of treatment with a dopaminergic agent by administering to a human in need of a treatment with a dopaminergic agent an effective amount of nicotine in combination with the dopaminergic agent, where the dopaminergic agent and nicotine are administered simultaneously to the human in an oral composition. In some embodiments, the dopaminergic agent and nicotine are administered in a single composition. In some embodiments, the dopaminergic agent and nicotine are administered in different compositions. In some embodiments, the dopaminergic agent and nicotine are admixed in the composition.

In some embodiments of this aspect, the invention provides a method of decreasing levodopa-induced dyskinesias by administering to a human in need of treatment an effective amount of nicotine in combination with an effective amount of levodopa and an effective amount of carbidopa, where the amount of nicotine is sufficient to reduce the dyskinesias and wherein levodopa and nicotine are administered orally simultaneously to said human.

In some embodiments of the methods of the invention, the dopaminergic agent is present in an amount sufficient to exert a therapeutic effect and the nicotinic receptor agonist is present in an amount sufficient to decrease a side effect of the dopaminergic agent by an average of at least about 30%, compared to the effect without the nicotinic receptor agonist. In some embodiments, the administration is oral administration. In some embodiments, the administration is transdermal administration.

In some embodiments of the methods of the invention, the nicotinic receptor modulator is administered to an animal suffering or about to suffer from a dopaminergic agent-induced side effect such that the nicotinic receptor modulator or a nicotinic receptor modulator metabolite reaches an effective concentration in the blood, plasma and/or target tissues in the animal so as to reduce or eliminate the side effects associated with the dopaminergic agent, where the effective concentration is the concentration necessary to reduce or eliminate the side effect. In some embodiments, the nicotinic receptor modulator or a metabolite is present in the bloodstream of the animal prior to the dopaminergic agent. In some embodiments, the nicotinic receptor modulator or a metabolite is in the bloodstream of the animal after the dopaminergic agent but prior to the beginning of the dopaminergic agent-induced side effect.

In various embodiments, presence of the dopaminergic agent and the nicotinic receptor modulator or a metabolite thereof in the blood is regulated temporally and/or spatially. For example, each agent can be administered at temporally different times (one before the other). In addition, the two agents can be administered at the same time but in a dosage form which functions for regulate release of one versus the other over a period of time (e.g., bi-layered tablet dosage form).

In some embodiments, the nicotinic receptor modulator or a metabolite is present in the bloodstream of the animal after the dopaminergic agent and after the animal exhibits the first signs of a dopaminergic agent-induced side effect. In some embodiments, the nicotinic receptor modulator or a metabolite is present in the bloodstream of the animal after the dopaminergic agent and after the animal exhibits a dopaminergic agent-induced side effect.

In some embodiments, the nicotinic receptor modulator is administered through pulsatile delivery. In some embodiments, the nicotinic receptor modulator is administered in an extended release or controlled release formulation. In some embodiments, the nicotinic receptor modulator and the dopaminergic agent are administered in a multilayer tablet.

In some embodiments of the methods of the invention, the nicotinic receptor agonist in the composition is selected from the group consisting of a simple or complex organic or inorganic molecule, a peptide, a protein, an oligonucleotide, an antibody, an antibody derivative, an antibody fragment, a vitamin derivative, a carbohydrate, and a toxin. Examples of nicotinic receptor agonists include, but are not limited to, nicotine, conotoxinMII, epibatidine, A-85380, cytisine, lobeline, anabasine, SIB-1508Y, SIB-1553A, ABT-418, ABT-594, ABT-894, TC-2403, TC-2559, RJR-2403, SSR180711, GTS-21 and varenicline. In some embodiments, the agonist is nicotine. In some embodiments of the invention, the dopaminergic agent is a dopamine precursor or a dopamine receptor agonist. Examples of dopaminergic agents include, but are not limited to, levodopa, bromocriptine, pergolide, pramipexole, cabergoline, ropinorole, apomorphine or a combination thereof. In some embodiments, the dopaminergic agent is levodopa.

In some embodiments, the methods described herein include a third agent also used for the treatment of a side effect of the dopaminergic agent. In some embodiments, the side effect treated with the nicotinic receptor modulator and the third agent is the same side effect. In some embodiments, the side effects treated with the nicotinic receptor modulator and the third agent are different side effects. In some embodiments, the third agent is amantadine. In some embodiments, the methods described herein include one or more agents used in the art in combination with a dopamine agent treatment to achieve a therapeutic effect. For instance, in some embodiments, the methods described herein include an agent such as carbidopa, which blocks the conversion of levodopa to dopamine in the blood. In some embodiments, the methods described herein include a COMT Inhibitors, such as entacapone. In some embodiments, the methods described herein include a monoamine oxidase type B (MAO-B) inhibitor such as selegiline.

In some embodiments of the methods of the invention, the individual suffers from a condition including Parkinson's disease, Alzheimer, dopa-responsive dystonia, cerebral palsy, postischemic contractile dysfunction, severe ovarian hyperstimulation syndrome, pediatric movement disorders and non-oliguric renal failure.

In another aspect, the invention provides methods of treating dyskinesias by administering to an animal in need of thereof an amount of a nicotinic receptor agonist sufficient to reduce or eliminate the dyskinesias.

In another aspect, the invention provides methods of treating Parkinson's disease by administering to an animal in need of thereof an amount of a nicotinic receptor agonist sufficient to reduce or eliminate Parkinson's disease. In some embodiments, the invention provides methods of treating Parkinson's disease by administering to an animal in need of thereof an amount of a nicotinic receptor agonist sufficient to reduce or eliminate physiological symptoms associated with Parkinson's disease, notwithstanding that the patient may still be afflicted with Parkinson.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the invention will become apparent to those skilled in the art from this detailed description.

All publications, patents, and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
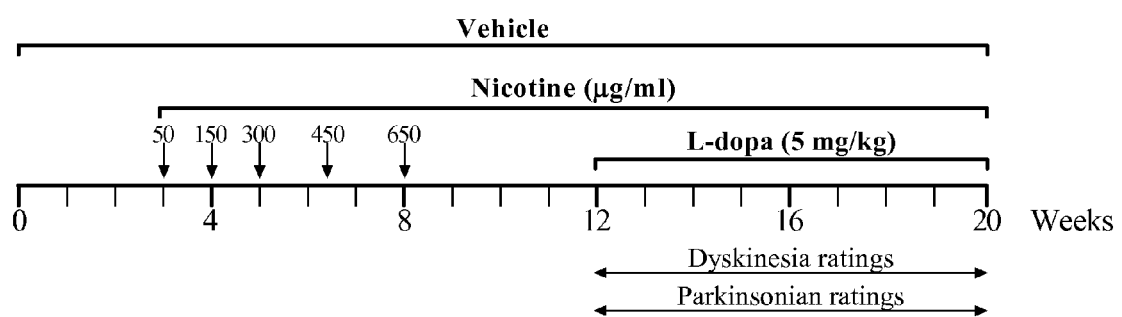
FIG. 1 depicts drug treatments schedule and behavioral testing periods.

Reference will now be made in detail to particularly preferred embodiments of the invention. Examples of the preferred embodiments are illustrated in the following Examples section.

Unless defined otherwise, all technical and scientific terms used herein have the same meaning as is commonly understood by one of skill in the art to which this invention belongs. All patents and publications referred to herein are incorporated by reference.

The invention provides compositions and methods. In some embodiments, the invention provides compositions and methods utilizing a nicotinic receptor modulator, e.g., to reduce or eliminate a side effect associated with dopaminergic agent treatment. In some embodiments, the invention provides compositions and methods utilizing a combination of a dopaminergic agent and a nicotinic receptor modulator. In some embodiments, the nicotinic receptor modulator reduces or eliminates a side effect associated with dopaminergic agent treatment. In some embodiments, the nicotinic receptor modulator is an agonist. Dopaminergic agents include a dopamine precursor or a dopamine receptor agonist. Examples of dopaminergic agents include levodopa, bromocriptine, pergolide, pramipexole, cabergoline, ropinorole, apomorphine or a combination thereof.

Nicotinic Receptor System

A. Striatal Nicotinic Cholinergic System

Localization of cholinergic neurons in striatum. Cholinergic neurons in the striatum are large interneurons that comprise about 2% of the neuronal population. Although limited in number, these interneurons have large axonal arbors that provide for a very dense local innervation in both the caudate and putamen. Indeed, high levels of acetylcholine, the acetylcholine synthesizing enzyme choline acetyltransferase and the acetylcholine degradative enzyme acetylcholinesterase are expressed in the striatum. These cholinergic markers overlap with dopaminergic arbors, containing dopamine, the dopamine synthetic enzyme tyrosine hydroxylase and other dopaminergic markers that are also expressed at a relatively high density. Without being limited to any theory, the overlapping distribution of the cholinergic and dopaminergic system provides the anatomical basis for a functional interaction between these two neurotransmitters.

Nicotinic acetylcholine receptors in striatum Striatal cholinergic interneurons are tonically active with a resultant ongoing release of acetylcholine that is regulated by multiple striatal systems including glutamatergic, dopaminergic, GABAergic, serotonergic, and other inputs. Released acetylcholine interacts with nAChRs present on dopaminergic, as well as other striatal neurons. These receptors are pentameric ligand-gated ion channels composed only of $\alpha$ subunits (homomeric), or of $\alpha$ and $\beta$ subunits (heteromeric receptors). To date, six different $\alpha$ ($\alpha 2$, $\alpha 3$, $\alpha 4$, $\alpha 5$, $\alpha 6$, $\alpha 7$) and three different $\beta$($\beta 2$, $\beta 3$, $\beta 4$) subunits have been identified in the nigrostriatal pathway. These subunits combine to form nAChRs, with the primary subtypes in the striatum composed of $\alpha 4\beta 2^*$ and $\alpha 3/\alpha 6\beta 2^*$ subunits as well as a small population of homomeric $\alpha 7$ nAChRs. (*The asterisks indicate that there are other subunits, some not yet identified that are also present and may be species dependent). The $\alpha 4\beta 2^*$ receptors are localized on dopaminergic terminals as well as other neurons in the striatum and throughout the CNS. However, they are not present in the peripheral nervous system or skeletal muscle. Interestingly, $\alpha 3/\alpha 6\beta 2^*$ receptor subtypes are selectively localized to the dopaminergic nigrostriatal pathway, and only a limited number of other brain areas, suggesting they may be of particular relevance to nigrostriatal function. These latter receptors ($\alpha 3/\alpha 6\beta 2^*$) are designated as expressing $\alpha 3$ and/or $\alpha 6$ subunits, because both are present in monkey striatum, and $\alpha$-conotoxinMII, the ligand used to identify these receptors, interacts with both $\alpha 3$ and $\alpha 6$ nAChR subtypes. Without being limited to any theory, the presence of different receptor populations on dopaminergic neurons raises the possibility that select subtypes may be more directly linked to the development of dyskinesias and the antidyskinetic properties of nicotine. Such knowledge would allow for the development of nAChR agonists more specifically targeted to ameliorating dyskinesias.

Striatal nicotinic receptor activation results in dopamine release. Endogenously released acetylcholine or exogenously applied agents such as nicotine and nicotinic agonists are known to stimulate nAChRs on dopaminergic neurons, with increases in dopamine release in the striatum under both in vitro and in vivo conditions. Agonist-evoked dopamine release in striatum occurs in response to stimulation of nAChR subtypes composed of $\alpha 4\beta 2^*$ and $\alpha 3/\alpha 6\beta 2^*$ subunits. Without being limited to any theory, the antidyskinetic effect of nicotine as described herein may be associated with changes in dopamine release after stimulation of α4β2* and/or α3/α6β2* nAChRs.

B. Striatal Dopaminergic System and its Involvement in Reduction of Dopaminergic Agent Treatment Side Effects.

One of the neurotransmitter systems responsible for the development of dopaminergic agent treatment side effects, such as dyskinesias, in parkinsonian animals or individuals with Parkinson's disease is the dopaminergic system itself. For instance, D1, D2 and D3 receptor agonists all induce dyskinesias, indicating that multiple receptor subtypes are involved. There appears to be an imbalance in activity of the two striatal output pathways with dyskinesias, possibly through activation of D1 and inhibition of D2 receptors on the direct and indirect pathway, respectively, with D3 receptors possibly exerting a modulatory influence. Despite a clear requirement for dopamine receptor stimulation, there are no consistent changes in the D1, D2 or D3 receptors themselves with dyskinesias. Without being limited to any theory, such findings most likely indicate that levodopa-induced changes may not occur at the receptor level, but involve downstream signaling events. Recent data suggest that D1 receptors, possibly through enhanced G-protein coupling, may play a role in dopaminergic agent-induced dyskinesias, while D2 receptors may be more relevant in mediating the antiparkinsonian action of dopaminergic agents. G-proteins are membrane-associated molecules that couple ligand-activated neurotransmitter receptors to intracellular second messenger systems. D1 dopamine receptor-stimulated striatal G-protein coupling was enhanced in striatal tissue from monkeys with dopaminergic agent-induced dyskinesias compared to controls. In addition, recent data show that there is also enhanced μ-opioid receptor coupling with dopaminergic agent-induced dyskinesias, another measure linked to activation of the D1 direct dopaminergic pathway. Increases have also been identified in cyclin-dependent kinase 5 (Cdk5) and dopamine cAMP-regulated phosphoprotein (DARPP-32), an important site for signal transduction integration in striatum. A down-regulation of striatal D1 receptor/NMDA receptor complexes has also been observed with the development of dyskinesias. Without being limited to any theory, the ability of nicotine to reduce dopaminergic agent-induced dyskinesias is likely related to normalization of the imbalance between striatal output pathways and modulation of signaling mechanisms.

In addition to changes in molecular markers linked to activation of the D1 direct dopaminergic pathway, the development of dopaminergic agent-induced dyskinesias is also associated with alterations in cellular function. In vivo and in vitro electrophysiological studies have been used to investigate basal ganglia function under normal conditions and in animals with nigrostriatal damage. This approach offers the advantage that it allows for a determination of changes in synaptic function and neuronal excitability not readily detectable using biochemical techniques. One in vitro preparation that has proved particularly useful to study the cellular mechanisms altered with dopaminergic agent-induced dyskinesias, are corticostriatal slices from rat brain. Brain slices at the level of the globus pallidus have generally been used as they incorporate many of the structures present in basal ganglia motor circuits. This includes glutamatergic inputs from the cortex that densely innervate striatal medium spiny GABAergic neurons and are a determinant of neuronal activity in striatal projection neurons. Synaptic plasticity, defined as long-lasting changes in the efficacy of synaptic transmission, has been identified in corticostriatal slices in vitro in the form of long-term potentiation (LTP), long-term depression (LTD) and depotentiation. In slices from unlesioned rats, high-frequency stimulation (HFS) of glutamatergic corticostriatal afferent fibers can induce both LTD and LTP in striatal medium spiny neurons, most likely due to a release of striatal glutamate which triggers dopamine release. Stimulation of both D1 and D2 receptors is required for the induction of LTD, whereas these two receptor subtypes play opposing roles in LTP. This plasticity at corticostriatal synapses is sensitive to both dopamine exposure and nigrostriatal damage with a loss of plasticity with lesioning. Moreover, it has been shown that chronic L-dopa treatment modulates plasticity. It was found that L-dopa treatment restores LTP in rats both without and with dyskinesias, but that low frequency stimulation (LFS)-induced responses (depotentiation) were specifically lost in dyskinetic rats. In addition, it was found that exogenous dopamine induced a slow-onset LTP in corticostriatal slices from L-dopa-treated dyskinetic animals but LTD in slices from nondyskinetic animals. Without being limited to any theory, these data suggest that dopamine-mediated activity-dependent synaptic potentiation may be altered in dyskinetic compared to nondyskinetic animals. Accumulating evidence thus suggests that abnormal plasticity at corticostriatal synapses may be involved in the development of dopaminergic agent-induced dyskinesias.

Interestingly, these inventors have recently found that nicotine treatment modulates synaptic plasticity in corticostriatal slices from nonhuman primates. In particular, it restores long-term depression (LTD) that is lost as a result of nigrostriatal damage. Without being limited to any theory it is possible that that nicotine modulates synaptic plasticity and promotes functional restoration also in animals with dopaminergic agent-induced dyskinesias and that this mechanism underlies its antidyskinetic effect.

Nicotinic Receptor Modulators

In one aspect, the invention provides compositions and methods utilizing a nicotinic receptor modulator, e.g., to reduce or eliminate a side effect associated with dopaminergic agent treatment. Modulators may be any suitable modulator.

In some embodiments, the nicotinic receptor modulator modulates a nicotinic receptor in the brain. In some embodiments, the nicotinic receptor modulator modulates a nicotinic receptor in the striatum or substantia niagra. In some embodiments, the nicotinic receptor modulator modulates a nicotinic receptor comprising at least one α subunit or a nicotinic receptor containing at least one subunit and at least one β subunit. In some embodiments, the α subunit is selected from the group consisting of α2, α3, α4, α5, α6, α7, α8, α9, and α10 and the β subunit is selected from the group consisting of β2, β3 and β4. In some embodiments, the nicotinic receptor modulator modulates a nicotinic receptor comprising subunits selected from the group consisting of α4β2, α6β2, α4α6β2, α4α5β, α4α6β2β3, α6β2β3 and α4α2β2. In some embodiments, the nicotinic receptor modulator modulates a nicotinic receptor comprising at least one α subunit selected from the group consisting of α4, α6, and α7.

In some embodiments, modulators useful in the invention are nicotinic receptor antagonist. The term "antagonist" as used herein refers to a molecule having the ability to inhibit a biological function of a target polypeptide. Accordingly, the term "antagonist" is defined in the context of the biological role of the target polypeptide. While preferred antagonists herein specifically interact with (e.g. bind to) the target, molecules that inhibit a biological activity of the target polypeptide by interacting with other members of the signal transduction pathway of which the target polypeptide is a member are also specifically included within this definition. Antagonists, as defined herein, without limitation, include antibodies, antibody derivatives, antibody fragments and immunoglobulin variants, peptides, peptidomimetics, simple or complex organic or inorganic molecule, antisense molecules, oligonucleotide decoys, proteins, oligonucleotide, vitamin derivatives, carbohydrates, and toxins.

In some embodiments, modulators useful in the invention are nicotinic receptor agonist. The term "agonist" as used herein refers to a molecule having the ability to initiate or enhance a biological function of a target polypeptide. Accordingly, the term "agonist" is defined in the context of the biological role of the target polypeptide. While preferred agonists herein specifically interact with (e.g. bind to) the target, molecules that enhance a biological activity of the target polypeptide by interacting with other members of the signal transduction pathway of which the target polypeptide is a member are also specifically included within this definition. Agonists, as defined herein, without limitation, include antibodies, antibody derivatives, antibody fragments and immunoglobulin variants, peptides, peptidomimetics, simple or complex organic or inorganic molecule, antisense molecules, oligonucleotide decoys, proteins, oligonucleotide, vitamin derivatives, carbohydrates, and toxins.

The nicotinic receptor agonist of the invention may be any ligand that binds to and activates the nicotinic receptor, thereby resulting in a biological response. The potential of a given substance to act as a nicotinic receptor agonist may be determined using standard in vitro binding assays and/or standard in vivo functionality tests.

Nicotinic receptor agonist for use according to the invention include those substances described in e.g. WO 92/21339 (Abbott), WO 94/08992 (Abbott), WO 96/40682 (Abbott), WO 9746554 (Abbott), WO 99/03859 (AstraZeneca), WO 96/15123 (Salk Institute) WO 97/19059 (Sibia), WO 00/10997 (Ortho-McNeil), WO 00/44755 (Abbott), WO 00/34284 (Synthelabo), WO 98/42713 (Synthelabo), WO 99/02517 (Synthelabo), WO 00/34279 (Synthelabo), WO 00/34279 (Synthelabo), WO 00/34284 (Synthelabo), EP 955301 (Pfizer), EP 857725 (Pfizer), EP 870768 (Pfizer), EP 311313 (Yamanouchi Pharmaceutical), WO 97/11072 (Novo Nordisk), WO 97/11073 (Novo Nordisk), WO 98/54182 (NeuroSearch), WO 98/54181 (NeuroSearch), WO 98/54152 (NeuroSearch), WO 98/54189 (NeuroSearch), WO 99/21834 (NeuroSearch), WO 99/24422 (NeuroSearch), WO 00/32600 (NeuroSearch), WO PCT/DK00/00211 (NeuroSearch), WO PCT/DK00/00202 (NeuroSearch), or their foreign equivalents.

Examples of nicotinic receptor agonist according to the invention include nicotine, ethyl nicotine, 3-ethynyl-5-(1-methyl-2-p-pyrrolidinyl)pyridine (SIB-1765F), 4-[[2-(1-methyl-2-pyrrolidinyl)ethyl]thi-o]phenol (SIB-1553), (S)-3-ethynyl-5-(1-methyl-2-pyrrolidinyl)-pyridine (SIB-1508Y), 4'-methylnicotine or (2S-trans)-3-(1,4-dimethyl-2-pyrrolidin-yl)pyridine (Abbott), 2-methyl-3-[(2S)-2-pyrrolidinyl-methoxy]-pyridine (ABT-089), 3-methyl-5-[(2S)-1-methyl-2-pyrrolidinyl]-isoxazole (ABT-418), 5-[(2R)-2-azetidinylmethoxy]-2-chloro-Pyridine (ABT-594), 3-PMP or 3-(1-pyrrolidinyl-methyl)pyridine (RJ Reynold), (3E)-N-methyl-4-(3-pyridi-nyl)-3-buten-1amine (RJR-2403), ana-basine or 3,4,5,6-tetrahydro-2,3'-bipyr-idine (RJ Reynold), 5-fluoronicotine or (S)-5-fluoro-3-(1-methyl-2-pyrroli-dinyl)pyridine (RJ Reynold), MCC or 2-(dimethylamino)ethyl methylcarbamate (Lundbeck), ethyl arecolone or 1-(1,2,5,6-tetrahydro-1-methyl-3-pyridinyl-)-1-propanone (Lilly), or isoarecolone or 1-(1,2,3,6-tetrahydro-1-methyl-4-1-pyridi-nyl)ethanone (Lilly), AR-R 17779 (AstraZeneca), epibati-dine, GTS-21, 1-(6-chloro-3-pyridyl)-homopiperazine, 1-(3-pyridyl)15 homopiperazine, 1-(5-ethynyl-3-pyridyl)-homopiperazine, conotoxinMII, epibatidine, A-85380, cytisine, lobeline or salts, free bases, racemates or enantiomers thereof.

Other nicotinic receptor agonists include choline esterase inhibitors (e.g., that increase local concentration of acetylcholine), derivatives of epibatidine that specifically bind the neuronal type of nicotinic receptors (with reduced binding to the muscarinic receptor) and having reduced deleterious side-effects (e.g., Epidoxidine, ABT-154, ABT418, ABT-594; Abbott Laboratories (Damaj et al. (1998) J. Pharmacol Exp. Ther. 284:1058 65, describing several analogs of epibatidine of equal potency but with high specificity to the neuronal type of nicotinic receptors). Further nicotinic receptor agonists of interest include, but are not necessarily limited to, N-methyl-carbamyl and N-methylthi-O-carbamyl esters of choline (e.g., trimethylaminoethanol) (Abood et al. (1988) Pharmacol. Biochem. Behav. 30:403 8); acetylcholine (an endogenous ligand for the nicotinic receptor); and the like.

In one embodiment, the nicotinic receptor agonist is nicotine (which is understood from to include nicotine derivatives and like compounds). Nicotine's chemical name is S-3-(1-methyl-2-pyrrolidinyl)pyridine. Its empirical formula is $C_{10}H_{14}N_2$, and its structural formula is

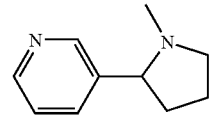

Nicotine may be isolated and purified from nature or synthetically produced in any manner. This term "nicotine" is also intended to encompass the commonly occurring salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate, ethanesulfonate, benzenesulfonate, p-toluene sulfonate, camphorate and pamoate salts. Nicotine is a colorless to pale yellow, strongly alkaline, oily, volatile, hygroscopic liquid having a molecular weight of 162.23

Unless specifically indicated otherwise, the term "nicotine" further includes any pharmacologically acceptable derivative or metabolite of nicotine which exhibits pharmacotherapeutic properties similar to nicotine. Such derivatives, metabolites, and derivatives of metabolites are known in the art, and include, but are not necessarily limited to, cotinine, norcotinine, nornicotine, nicotine N-oxide, cotinine N-oxide, 3-hydroxycotinine and 5-hydroxycotinine or pharmaceutically acceptable salts thereof. A number of useful derivatives of nicotine are disclosed within the Physician's Desk Reference (most recent edition) as well as Harrison's Principles of Internal Medicine. Methods for production of nicotine derivatives and analogues are well known in the art. See, e.g., U.S. Pat. Nos. 4,590,278; 4,321,387; 4,452,984; 4,442,292; and 4,332,945.

The compounds of the present invention may have asymmetric carbon atoms. All isomers, including diastereomeric mixtures such as racemic mixtures and pure enantiomers are considered as part of the invention.

Without being limited to any one theory, one mechanism of action can be that after a prolong exposure to nicotinic receptor agonist nicotinic receptors become desensitized and the nicotinic receptor agonists start working as nicotinic receptor antagonists. In some embodiments, the nicotinic receptor agonists work as antagonists to reduce or eliminate a side effect induced by a dopaminergic agent.

In some embodiments, the invention provides a composition for administration of nicotine to an animal. In some embodiments, the invention provides a composition for administration of nicotine to an animal to reduce a side effect of a dopaminergic agent, e.g., for the oral delivery of nicotine, that contain at least about 1, 5, 10, 20, 30, 40, 50, 60, 70, 80, 90, 95, 99, 99.5, 99.9, or 99.99% nicotine. In some embodiments, the invention provides a composition for the oral delivery of nicotine that contains no more than about 2, 5, 10, 20, 30, 40, 50, 60, 70, 80, 90, 95, 99, 99.5, 99.9, 99.99, or 100% nicotine. In some embodiments, the invention provides a composition that contains about 1-100% nicotine, or about 10-100% nicotine, or about 20-100% nicotine, or about 50-100% nicotine, or about 80-100% nicotine, or about 90-100% nicotine, or about 95-100% nicotine, or about 99-100% nicotine. In some embodiments, the invention provides a composition that contains about 1-90% nicotine, or about 10-90% nicotine, or about 20-90% nicotine, or about 50-90% nicotine, or about 80-90% nicotine. In some embodiments, the invention provides a composition that contains about 1-75% nicotine, or about 10-75% nicotine, or about 20-75% nicotine, or about 50-75% nicotine. In some embodiments, the invention provides a composition that contains about 1-50% nicotine, or about 10-50% nicotine, or about 20-50% nicotine, or about 30-50% nicotine, or about 40-50% nicotine. In some embodiments, the invention provides a composition that contains about 1-40% nicotine, or about 10-40% nicotine, or about 20-40% nicotine, or about 30-40% nicotine. In some embodiments, the invention provides a composition that contains about 1-30% nicotine, or about 10-30% nicotine, or about 20-30% nicotine. In some embodiments, the invention provides a composition that contains about 1-20% nicotine, or about 10-20% nicotine. In some embodiments, the invention provides a composition that contains about 1-10% nicotine. In some embodiments, the invention provides a composition that contains about 1, 2, 5, 10, 20, 30, 40, 50, 60, 70, 80, 90, 95, 96, 97, 98, or 99% nicotine.

In some of these embodiments, a pharmaceutically acceptable excipient is also included.

Dopaminergic Agents

In one aspect, the invention provides compositions and methods to reduce or eliminate the effects of a dopaminergic agent. In some embodiments, the compositions and methods retain or enhance a desired effect of the dopaminergic agent, e.g., antiparkinsonian effect. The methods and compositions of the invention apply to any dopaminergic agent for which it is desired to reduce one or more side effects. In some embodiments, the compositions and methods of the invention utilize a dopamine precursor. In some embodiments, the compositions and methods of the invention utilize a dopamine agonist. In some embodiments, the dopaminergic agent is levodopa, bromocriptine, pergolide, pramipexole, cabergoline, ropinorole, apomorphine or a combination thereof. In some embodiments, the dopaminergic agent is levodopa. In some embodiments, the compositions and methods of the invention utilize one or more agents used in the art in combination with a dopamine agent treatment to achieve a therapeutic effect. For instance, in one exemplary embodiment the compositions and methods of the invention utilize levodopa in combination with an agent such as carbidopa, which blocks the conversion of levodopa to dopamine in the blood. In another exemplary embodiment, the compositions and methods of the invention utilize levodopa in combination with a COMT Inhibitor, such as entacapone. In another exemplary embodiment, the compositions and methods of the invention utilize levodopa in combination with a monoamine oxidase type B (MAO-B) inhibitor such as selegiline. In yet another exemplary embodiment, the compositions and methods of the invention utilize levodopa in combination with amantadine.

Levodopa

Levodopa, an aromatic amino acid, is a white, crystalline compound, slightly soluble in water, with a molecular weight of 197.2. It is designated chemically as (−)-L-a-amino-b-(3,4-dihydroxybenzene) propanoic acid. Its empirical formula is $C_9H_{11}NO_4$, and its structural formula is

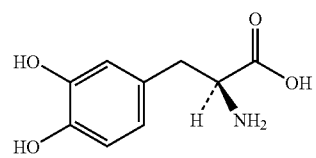

Levodopa is used for the treatment of Parkinson's disease. Parkinson's disease is a progressive, neurodegenerative disorder of the extrapyramidal nervous system affecting the mobility and control of the skeletal muscular system. Its characteristic features include resting tremor, rigidity, and bradykinetic movements Current evidence indicates that symptoms of Parkinson's disease are related to depletion of dopamine in the corpus striatum. Administration of dopamine is ineffective in the treatment of Parkinson's disease apparently because it does not cross the blood-brain barrier. However, levodopa, the metabolic precursor of dopamine, does cross the blood-brain barrier, and presumably is converted to dopamine in the brain. This is thought to be the mechanism whereby levodopa relieves symptoms of Parkinson's disease.

However, although initially very effective, long-term treatment with levodopa gives rise to multiple complications. Levodopa treatment may cause nausea, vomiting, involuntary movements (e.g. dyskinesias), mental disturbances, depression, syncope, and hallucinations. The precise pathophysiological mechanisms of levodopa side effects are still enigmatic, but are thought to be due to increased brain dopamine following administration of levodopa.

Previous work has shown that levodopa induced-dyskinesias (LIDs) arise due to enhanced intermittent stimulation of D1, D2 and/or other dopamine receptor subtypes. This results in an imbalance in activity of the two major striatal output pathways, possibly through activation of D1 and inhibition of D2 receptors on the direct and indirect dopaminergic pathways, respectively, although there is some overlap between striatal efferents. Recent data suggest that D1 receptors, through enhanced G-protein coupling, may play a more prominent role in functional hypersensitivity associated with levodopa-induced dyskinesias, while D2 receptor activation may be more closely linked to the antiparkinsonian action of dopaminergic drugs Side Effects The principal adverse reactions of dopaminergic agent include headache, diarrhea, hypertension, nausea, vomiting, involuntary movements (e.g. dyskinesias), mental disturbances, depression, syncope, hallucinations, and abnormal renal function.

The invention provides compositions and methods utilizing a nicotinic receptor modulator that reduces or eliminates a side effect associated with dopaminergic agent treatment. In some embodiments, the invention provides compositions and methods utilizing a nicotinic receptor modulator that reduces or eliminates dyskinesias associated with dopaminergic agent treatment. Without being limited to any theory, one possibility is that nicotinic receptor modulator exerts its effect by acting at nicotinic acetylcholine receptors (nAChR), which are expressed in the striatum. There is a dense cholinergic innervation in striatum that closely coincides with dopaminergic neurons. Under physiological conditions, these cholinergic interneurons tonically release acetylcholine, which stimulates nicotinic receptors on dopaminergic nerve terminals to release dopamine. Similarly, exogenously applied agents such as nicotine result in a release of dopamine from striatal terminals.

In some embodiments, the invention provides compositions and methods utilizing a combination of a dopaminergic agent and a nicotinic receptor modulator that reduces or eliminates a side effect associated with dopaminergic agent treatment. Typically, the nicotinic receptor modulator is an agonist. In some embodiments, the nicotinic receptor agonist modulates a nicotinic receptor comprising at least one $\alpha$ subunit or a nicotinic receptor containing at least one $\alpha$ subunit and at least one $\beta$ subunit. In some embodiments, the $\alpha$ subunit is selected from the group consisting of $\alpha 2$, $\alpha 3$, $\alpha 4$, $\alpha 5$, $\alpha 6$, $\alpha 7$, $\alpha 8$, $\alpha 9$, and $\alpha 10$ and the $\beta$ subunit is selected from the group consisting of $\beta 2$, $\beta 3$ and $\beta 4$. In some embodiments, the nicotinic receptor agonist modulates a nicotinic receptor composed of subunits selected from the group consisting of $\alpha 4\beta 2$, $\alpha 6\beta 2$, $\alpha 4\alpha 6\beta 2$, $\alpha 4\alpha 5\beta 2$, $\alpha 4\alpha 6\beta 2\beta 3$, $\alpha 6\beta 2\beta 3$ and $\alpha 4\alpha 2\beta 2$. In some embodiments, the nicotinic receptor modulator modulates a nicotinic receptor comprising at least one $\alpha$ subunit selected from the group consisting of $\alpha 4$, $\alpha 6$, and $\alpha 7$.

In some embodiments, the dopaminergic agents include a dopamine precursor or a dopamine receptor agonist Examples of dopaminergic agents include, but are not limited to, levodopa, bromocriptine, pergolide, pramipexole, cabergoline, ropinorole, apomorphine or a combination thereof.

The nicotinic receptor modulator causing a decrease in the side effects of the dopaminergic agent may be an agonist or an antagonist of a protein. The modulatory effect may be dose-dependent, e.g., some modulators act as agonists in one dosage range and antagonists in another. In some embodiments, a modulator of a nicotinic receptor is used in a dosage wherein it acts primarily as an agonist.

Typically, the use of the nicotinic receptor modulator, e.g., agonist, results in a decrease in one or more side effects of the dopaminergic agent. The therapeutic effect(s) of the dopaminergic agent may be decreased, remain the same, or increase; however, in preferred embodiments, if the therapeutic effect is decreased, it is not decreased to the same degree as the side effects. It will be appreciated that a given dopaminergic agent may have more than one therapeutic effects and or one or more side effects, and it is possible that the therapeutic ratio (in this case, the ratio of change in desired effect to change in undesired effect) may vary depending on which effect is measured. However, at least one therapeutic effect of the dopaminergic agent is decreased to a lesser degree than at least one side effect of the dopaminergic agent.

In addition, in some embodiments, one or more therapeutic effects of the dopaminergic agent are enhanced by use in combination with a nicotinic receptor modulator, while one or more side effects of the dopaminergic agent is reduced or substantially eliminated. For example, in some embodiments, the antiparkinsonian effect of the dopaminergic agent is enhanced while one or more side effects of the dopaminergic agent is reduced or substantially eliminated.

Hence, in some embodiments the invention provides compositions that include a dopaminergic agent and a nicotinic receptor modulator, where the dopaminergic agent is present in an amount sufficient to exert a therapeutic effect and the nicotinic receptor modulator is present in an amount sufficient to decrease side effect of the dopaminergic agent when compared to the side effect without the nicotinic receptor modulator, when the composition is administered to an animal.

In some embodiments, compositions of the invention include one or more dopaminergic agent with one or more nicotinic receptor modulators. One or more of the dopaminergic agent may have one or more side effects which are desired to be decreased. In some embodiments, compositions of the invention include one or more agents, one or more dopaminergic agent with one or more nicotinic receptor modulators. The one or more agents are agents used in the art in combination with a dopamine agent treatment to achieve a therapeutic effect and/or reduce a side effect. In some embodiments, the compositions of the invention include an agent such as carbidopa, which blocks the conversion of levodopa to dopamine in the blood. In some embodiments, the compositions of the invention include a COMT Inhibitor, such as entacapone. In some embodiments, the compositions of the invention include a monoamine oxidase type B (MAO-B) inhibitor such as selegiline. In some embodiments, the compositions of the invention include amantadine.

Compositions of the invention may be prepared in any suitable form for administration to an animal. In some embodiments, the invention provides pharmaceutical compositions.

In some embodiments, the invention provides compositions suitable for oral administration. In some embodiments, compositions are suitable for transdermal administration. In some embodiments, compositions are suitable for injection by any standard route of injection, e.g., intravenous, subcutaneous, intramuscular, or intraperitoneal. Compositions suitable for other routes of administration, such and inhalation, are also encompassed by the invention, as described herein.

In some embodiments the invention provides methods of decreasing a side effect of a dopaminergic agent in an animal, e.g. a human, that has received an amount of the dopaminergic agent sufficient to produce a side effect by administering to the animal, e.g., human, an amount of a nicotinic receptor modulator sufficient to reduce or eliminate the side effect.

The side effect may be acute or chronic. The effect may be biochemical, cellular, at the tissue level, at the organ level, at the multi-organ level, or at the level of the entire organism. The effect may manifest in one or more objective or subjective manners, any of which may be used to measure the effect. If an effect is measured objectively or subjectively (e.g., dyskinesias and the like), any suitable method for evaluation of objective or subjective effect may be used. Examples include visual and numeric scales and the like for evaluation by an individual. A further example includes sleep latency for measurement of drowsiness, or standard tests for measurement of concentration, mentation, memory, and the like. These and other methods of objective and subjective evaluation of side effects by an objective observer, the individual, or both, are well-known in the art.

A "therapeutic effect," as that term is used herein, encompasses a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. A prophylactic effect includes delaying or eliminating the appearance of a disease or condition, delaying or eliminating the onset of symptoms of a disease or condition, slowing, halting, or reversing the progression of a disease or condition, or any combination thereof.

Compositions

In one aspect the invention provides compositions that include a nicotinic receptor modulator, e.g., that reduces or eliminates a side effect of one or more dopaminergic agent. In some embodiments, a dopaminergic agent is co-administered with the nicotinic receptor modulator. "Co-administration," "administered in combination with," and their grammatical equivalents, as used herein, encompasses administration of two or more agents to an animal so that both agents and/or their metabolites are present in the animal at the same time. Co-administration includes simultaneous administration in separate compositions, administration at different times in separate compositions, or administration in a composition in which both agents are present.

In some embodiments, the invention provides compositions containing a nicotinic receptor modulator. In further embodiments the invention provides pharmaceutical compositions that further include a pharmaceutically acceptable excipient.

In some embodiments, the invention includes pharmaceutical compositions wherein the nicotinic receptor modulator is present in an amount sufficient to decrease a side effect of a dopaminergic agent when the composition is administered to an animal. In some embodiments, the invention includes pharmaceutical compositions where the nicotinic receptor modulator is present in an amount sufficient to decrease a side effect of a dopaminergic agent and to prevent addiction to the nicotinic receptor modulator when the composition is administered to an animal. For example, the pharmaceutical compositions including a nicotinic receptor modulator are administered through various routes of delivery further described herein.

In one embodiment, the pharmaceutical compositions including a nicotinic receptor modulator are administered orally to an animal. In various embodiments, the invention provides a solid pharmaceutical composition for oral administration containing an effective amount of a nicotinic receptor modulator and a pharmaceutical excipient suitable for oral administration; or a liquid pharmaceutical composition for oral administration containing an effective amount of a nicotinic receptor modulator and a pharmaceutical excipient suitable for oral administration.

In some embodiments, the pharmaceutical compositions are suitable for transdermal administration.

In some embodiments, the invention provides a composition containing a nicotinic receptor modulator, where nicotinic receptor modulator is present in an amount sufficient to decrease a side effect of a dopaminergic agent by a measurable amount, compared to the side effect without the nicotinic receptor modulator, when the composition is administered to an animal. In some embodiments, a side effect of the dopaminergic agent is decreased by an average of at least about 5, 10, 15, 20, 25, 30, 35, 40, 45, 50, 55, 60, 65, 70, 75, 80, 85, 90, 95, or more than 95%, compared to the side effect without the nicotinic receptor modulator. In some embodiments, a side effect of the dopaminergic agent is decreased by an average of at least about 5%, compared to the side effect without the nicotinic receptor modulator. In some embodiments, a side effect of the dopaminergic agent is decreased by an average of at least about 10%, compared to the side effect without the nicotinic receptor modulator. In some embodiments, a side effect of the dopaminergic agent is decreased by an average of at least about 15%, compared to the side effect without the nicotinic receptor modulator. In some embodiments, a side effect of the dopaminergic agent is decreased by an average of at least about 20%, compared to the side effect without the nicotinic receptor modulator. In some embodiments, a side effect of the dopaminergic agent is decreased by an average of at least about 30%, compared to the side effect without the nicotinic receptor modulator. In some embodiments, a side effect is substantially eliminated compared to the side effect without the nicotinic receptor modulator. "Substantially eliminated" as used herein encompasses no measurable or no statistically significant side effect (one or more side effects) of the dopaminergic agent, when a nicotinic receptor modulator is administered.

In some embodiments, the invention provides compositions that contain a nicotinic receptor agonist, e.g., nicotine, where the nicotinic receptor agonist, e.g., nicotine is present in an amount sufficient to decrease a side effect of the dopaminergic agent by a measurable amount, compared to the side effect without the nicotinic receptor agonist, e.g., nicotine when the composition is administered to an animal. The measurable amount may be an average of at least about 5%, 10%, 15%, 20%, 30% or more than 30% as described herein. The side effect may be any side effect as described herein. In some embodiments, the side effect is dyskinesias.

In exemplary embodiments, the invention provides a composition that contains nicotine, where nicotine is present in an amount effective to decrease a side effect of a dopaminergic agent by a measurable amount (e.g., an average of at least about 5, 10, 15, 20, 30 or more than 30%, as described herein). In some exemplary embodiments, the invention provides a composition that contains nicotine, where nicotine is present in an amount effective to decrease a side effect of a dopaminergic agent by a measurable amount (e.g., an average of at least about 5, 10, 15, 20, or more than 20%, as described herein) and to increase the therapeutic effect of the dopaminergic agent by a measurable amount (e.g., an average of at least about 5, 10, 15, 20, 30 or more than 30%, as described herein). In some embodiments, the invention provides a composition that contains nicotine, where nicotine is present in amount effective to decrease a side effect of a dopaminergic agent by a measurable amount (e.g., an average of at least about 5, 10, 15, 20, 30 or more than 30%, as described herein) and to prevent addition to nicotine. In some exemplary embodiments, the invention provides a composition that contains nicotine, where nicotine is present in an amount effective to decrease a side effect of a dopaminergic agent by a measurable amount (e.g., an average of at least about 5, 10, 15, 20, 30 or more than 30%, as described herein), and to increase the therapeutic effect of the dopaminergic agent by a measurable amount (e.g., an average of at least about 5, 10, 15, 20, 30 or more than 30%, as described herein), and to prevent addiction to nicotine. The side effect may be any side effect as described herein. In some embodiments, the side effect is dyskinesias.

In some embodiments, the invention provides compositions containing a combination of a dopaminergic agent and a nicotinic receptor modulator that reduces or eliminates a side effect of the dopaminergic agent. In some embodiments, the invention provides compositions containing a combination of a dopaminergic agent and a nicotinic receptor modulator that reduces or eliminates a side effect of the dopaminergic agent, where the nicotinic receptor modulator is present in an amount that prevents addiction to the nicotine receptor modulator. In some embodiments, the invention provides pharmaceutical compositions that further include a pharmaceutically acceptable excipient. In some embodiments, the pharmaceutical compositions are suitable for oral administration. In some embodiments, the pharmaceutical compositions are suitable for transdermal administration. In some embodiments, the pharmaceutical compositions are suitable for injection. Other forms of administration are also compatible with embodiments of the pharmaceutical compositions of the invention, as described herein.

In some embodiments, the nicotinic receptor modulator comprises an agonist or antagonist as described herein. In some embodiments, after prolong exposure to an agonist the nicotinic receptors become desensitized and the nicotinic receptor agonists described herein work as antagonists.

In some embodiments, the side effect of the dopaminergic agent that is reduced is selected from the group consisting of involuntary movements (e.g. dyskinesias), mental disturbances, depression, syncope, hallucinations, or combinations thereof. In some embodiments, the side effect of the dopaminergic agent that is reduced is dyskinesias.

In some embodiments the dopaminergic agent is a dopamine precursor or a dopamine agonist. Examples of dopaminergic agents include, but are not limited to, levodopa, bromocriptine, pergolide, pramipexole, cabergoline, ropinorole, apomorphine or a combination thereof.

In some embodiments, compositions of the invention include one or more agents, one or more dopaminergic agent with one or more nicotinic receptor modulators. The one or more agents are agents used in the art in combination with a dopamine agent treatment to achieve a therapeutic effect and/or reduce a side effect. In some embodiments, the compositions of the invention include an agent such as carbidopa, which blocks the conversion of levodopa to dopamine in the blood. In some embodiments, the compositions of the invention include a COMT Inhibitor, such as entacapone. In some embodiments, the compositions of the invention include a monoamine oxidase type B (MAO-B) inhibitor such as selegiline. In some embodiments, the compositions of the invention include amantadine.

In some embodiments, the invention provides a composition containing a dopaminergic agent and a nicotinic receptor modulator, where the dopaminergic agent is present in an amount sufficient to exert a therapeutic effect and the nicotinic receptor modulator is present in an amount sufficient to decrease side effect of the dopaminergic agent by a measurable amount, compared to the side effect without the nicotinic receptor modulator, when the composition is administered to an animal. In some embodiments, a side effect of the dopaminergic agent is decreased by an average of at least about 5, 10, 15, 20, 25, 30, 35, 40, 45, 50, 55, 60, 65, 70, 75, 80, 85, 90, 95, or more than 95%, compared to the side effect without the nicotinic receptor modulator. In some embodiments, a side effect of the dopaminergic agent is decreased by an average of at least about 5%, compared to the side effect without the nicotinic receptor modulator. In some embodiments, a side effect of the dopaminergic agent is decreased by an average of at least about 10%, compared to the side effect without the nicotinic receptor modulator. In some embodiments, a side effect of the dopaminergic agent is decreased by an average of at least about 15%, compared to the side effect without the nicotinic receptor modulator. In some embodiments, a side effect of the dopaminergic agent is decreased by an average of at least about 20%, compared to the side effect without the nicotinic receptor modulator. In some embodiments, a side effect of the dopaminergic agent is decreased by an average of at least about 30%, compared to the side effect without the nicotinic receptor modulator. In some embodiments, a side effect is substantially eliminated compared to the side effect without the nicotinic receptor modulator. "Substantially eliminated" as used herein encompasses no measurable or no statistically significant side effect (one or more side effects) of the dopaminergic agent, when administered in combination with the nicotinic receptor modulator.

Thus, in some embodiments, the invention provides compositions that contain a nicotinic receptor agonist, e.g., nicotine, and a dopaminergic agent, where the dopaminergic agent is present in an amount sufficient to exert an therapeutic effect and the nicotinic receptor agonist, e.g., nicotine is present in an amount sufficient to decrease a side effect of the dopaminergic agent by a measurable amount, compared to the side effect without the nicotinic receptor agonist, e.g., nicotine when the composition is administered to an animal. The measurable amount may be an average of at least about 5%, 10%, 15%, 20%, 30% or more than 30% as described herein. The side effect may be any side effect as described herein. In some embodiments, the side effect is dyskinesias.

In some embodiments, the invention provides compositions that contain a nicotinic receptor agonist that is nicotine, and a dopaminergic agent that is levodopa, where the levodopa is present in an amount sufficient to exert a therapeutic effect and nicotine is present in an amount sufficient to decrease side effect of levodopa by a measurable amount, compared to the side effect without nicotine when the composition is administered to an animal. The measurable amount may be an average of at least about 5%, 10%, 15%, 20%, 30% or more than 30% as described herein. The side effect may be any side effect as described herein. In some embodiments, the side effect is dyskinesias.

In some embodiments, the nicotinic receptor modulator is present in an amount sufficient to decrease a side effect of the dopaminergic agent by a measurable amount and to increase a therapeutic effect of the dopaminergic agent by a measurable amount, compared to the side effect and therapeutic effect without the nicotinic receptor modulator, when the composition is administered to an animal. In some embodiments, a therapeutic effect of the dopaminergic agent is increased by an average of at least about 5, 10, 15, 20, 25, 30, 35, 40, 45, 50, 55, 60, 65, 70, 75, 80, 85, 90, 95, or more than 95%, compared to the therapeutic effect without the nicotinic receptor modulator. In some embodiments, a therapeutic effect of the dopaminergic agent is increased by an average of at least about 5%, compared to the therapeutic effect without the nicotinic receptor modulator. In some embodiments, a therapeutic effect of the dopaminergic agent is increased by an average of at least about 10%, compared to the therapeutic effect without the nicotinic receptor modulator. In some embodiments, a therapeutic effect of the dopaminergic agent is increased by an average of at least about 15%, compared to the therapeutic effect without the nicotinic receptor modulator. In some embodiments, a therapeutic effect of the dopaminergic agent is increased by an average of at least about 20%, compared to the therapeutic effect without the nicotinic receptor modulator. In some embodiments, a therapeutic effect of the dopaminergic agent is increased by an average of at least about 30%, compared to the therapeutic effect without the nicotinic receptor modulator. In some embodiments, a therapeutic effect of the dopaminergic agent is increased by an average of at least about 40%, compared to the therapeutic effect without the nicotinic receptor modulator. In some embodiments, a therapeutic effect of the dopaminergic agent is increased by an average of at least about 50%, compared to the therapeutic effect without the nicotinic receptor modulator.

Thus, in some embodiments, the invention provides compositions containing a nicotinic receptor modulator present in an amount sufficient to decrease a side effect of a dopaminergic agent by an average of at least about 5% and to increase a therapeutic effect of the dopaminergic agent by an average of at least about 5%, compared to the side effect and therapeutic effect without the nicotinic receptor modulator, when the composition is administered to an animal in combination with the dopaminergic agent. In some embodiments, the invention provides compositions containing a nicotinic receptor modulator present in an amount sufficient to decrease a side effect of a dopaminergic agent by an average of at least about 10% and to increase a therapeutic effect of the dopaminergic agent by an average of at least about 10%, compared to the side effect and therapeutic effect without the nicotinic receptor modulator, when the composition is administered to an animal in combination with the dopaminergic agent. In some embodiments, the invention provides compositions containing a nicotinic receptor modulator present in an amount sufficient to decrease a side effect of a dopaminergic agent by an average of at least about 20% and to increase a therapeutic effect of the dopaminergic agent by an average of at least about 20%, compared to the side effect and therapeutic effect without the nicotinic receptor modulator, when the composition is administered to an animal in combination with the dopaminergic agent. In some embodiments, the invention provides compositions containing a nicotinic receptor modulator present in an amount sufficient to decrease a side effect of a dopaminergic agent by an average of at least about 10% and to increase a therapeutic effect of the dopaminergic agent by an average of at least about 20%, compared to the side effect and therapeutic effect without the nicotinic receptor modulator, when the composition is administered to an animal in combination with the dopaminergic agent. In some embodiments, the invention provides compositions containing a nicotinic receptor modulator present in an amount sufficient to decrease a side effect of a dopaminergic agent by an average of at least about 10% and to increase a therapeutic effect of the dopaminergic agent by an average of at least about 30%, compared to the side effect and therapeutic effect without the nicotinic receptor modulator, when the composition is administered to an animal in combination with the dopaminergic agent. In some embodiments, the invention provides compositions containing a nicotinic receptor modulator present in an amount sufficient to decrease a side effect of a dopaminergic agent by an average of at least about 10% and to increase a therapeutic effect of the dopaminergic agent by an average of at least about 40%, compared to the side effect and therapeutic effect without the nicotinic receptor modulator, when the composition is administered to an animal in combination with the dopaminergic agent. In some embodiments, the invention provides compositions containing a nicotinic receptor modulator present in an amount sufficient to decrease a side effect of a dopaminergic agent by an average of at least about 10% and to increase a therapeutic effect of the dopaminergic agent by an average of at least about 50%, compared to the side effect and therapeutic effect without the nicotinic receptor modulator, when the composition is administered to an animal in combination with the dopaminergic agent.

In some embodiments, the invention provides compositions containing a nicotinic receptor agonist, e.g., nicotine, present in an amount sufficient to decrease a side effect of a dopaminergic agent by an average of at least about 5% and to increase a therapeutic effect of the dopaminergic agent by an average of at least about 5%, when the composition is administered to an animal in combination with the dopaminergic agent, compared to the side effect and therapeutic effect without the nicotinic receptor agonist, e.g., nicotine. In some embodiments, the invention provides compositions containing a nicotinic receptor agonist, e.g., nicotine present in an amount sufficient to decrease a side effect of a dopaminergic agent by an average of at least about 10% and to increase a therapeutic effect of the dopaminergic agent by an average of at least about 10%, when the composition is administered to an animal in combination with the dopaminergic agent, compared to the side effect and therapeutic effect when the dopaminergic agent is administered without the a nicotinic receptor agonist, e.g., nicotine. In some embodiments, the invention provides compositions containing a nicotinic receptor agonist, e.g., nicotine present in an amount sufficient to decrease a side effect of a dopaminergic agent by an average of at least about 20% and to increase a therapeutic effect of the dopaminergic agent by an average of at least about 20%, when the composition is administered to an animal in combination with the dopaminergic agent, compared to the side effect and therapeutic effect when the dopaminergic agent is administered without the a nicotinic receptor agonist, e.g., nicotine. In some embodiments, the invention provides compositions containing a nicotinic receptor agonist, e.g., nicotine present in an amount sufficient to decrease a side effect of a dopaminergic agent by an average of at least about 10% and to increase a therapeutic effect of the dopaminergic agent by an average of at least about 20%, when the composition is administered to an animal in combination with the dopaminergic agent, compared to the side effect and therapeutic effect when the dopaminergic agent is administered without the a nicotinic receptor agonist, e.g., nicotine. In some embodiments, the invention provides compositions containing a nicotinic receptor agonist, e.g., nicotine present in an amount sufficient to decrease a side effect of a dopaminergic agent by an average of at least about 10% and to increase a therapeutic effect of the dopaminergic agent by an average of at least about 30%, when the composition is administered to an animal in combination with the dopaminergic agent, compared to the side effect and therapeutic effect when the dopaminergic agent is administered without the nicotinic receptor agonist, e.g., nicotine. In some embodiments, the invention provides compositions containing a nicotinic receptor agonist, e.g., nicotine present in an amount sufficient to decrease a side effect of a dopaminergic agent by an average of at least about 10% and to increase a therapeutic effect of the dopaminergic agent by an average of at least about 40%, when the composition is administered to an animal in combination with the dopaminergic agent, compared to the side effect and therapeutic effect when the dopaminergic agent is administered without the nicotinic receptor agonist, e.g., nicotine. In some embodiments, the invention provides compositions containing a nicotinic receptor agonist, e.g., nicotine present in an amount sufficient to decrease a side effect of a dopaminergic agent by an average of at least about 10% and to increase a therapeutic effect of the dopaminergic agent by an average of at least about 50%, when the composition is administered to an animal in combination with the dopaminergic agent, compared to the side effect and therapeutic effect when the dopaminergic agent is administered without the a nicotinic receptor agonist, e.g., nicotine.

In exemplary embodiments, the invention provides a composition that contains nicotine and a dopaminergic agent, such as levodopa or a dopamine agonist, where the dopaminergic agent is present in an amount sufficient to exert a therapeutic effect, and nicotine is present in an amount effective to decrease a side effect of the dopaminergic agent by a measurable amount (e.g., an average of at least about 5, 10, 15, 20, 30 or more than 30%, as described herein) and to increase the therapeutic effect of the dopaminergic agent by a measurable amount (e.g., an average of at least about 5, 10, 15, 20, 30 or more than 30%, as described herein). The side effect may be any side effect as described herein. In some embodiments, the side effect is dyskinesias.

An "average" as used herein is preferably calculated in a set of normal human subjects, this set being at least about 3 human subjects, preferably at least about 5 human subjects, preferably at least about 10 human subjects, even more preferably at least about 25 human subjects, and most preferably at least about 50 human subjects.

In some embodiments, the invention provides a composition that contains a dopaminergic agent and a nicotinic receptor modulator, e.g. an agonist such as nicotine. In some embodiments, the a concentration of one or more of the dopaminergic agents and/or nicotinic receptor modulator, e.g. an agonist such as a nicotine is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, a concentration of one or more of the dopaminergic agents and/or nicotinic receptor modulator, e.g. an agonist such as a nicotine is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, a concentration of one or more of the dopaminergic agents and/or nicotinic receptor modulator, e.g. an agonist such as a nicotine is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v. v/v.

In some embodiments, a concentration of one or more of the dopaminergic agents and/or nicotinic receptor modulator, e.g. a an agonist such as a nicotine is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more of the dopaminergic agents and/or nicotinic receptor modulator, e.g. an agonist such as a nicotine is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more of the dopaminergic agents and/or nicotinic receptor modulator, e.g. a an agonist such as a nicotine is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more of the dopaminergic agents and/or nicotinic receptor modulator, e.g. a an agonist such as a nicotine is in the range of 0.0001-10 g, 0.0005-9 g, 0.001-8 g, 0.005-7 g, 0.01-6 g, 0.05-5 g, 0.1-4 g, 0.5-4 g, or 1-3 g.

In exemplary embodiments, compositions of the invention include nicotine, where nicotine is present in an amount from about 0.1-1000 mg, or about 1-1000 mg, or about 5-1000 mg, or about 10-1000 mg, or about 1-500 mg, or about 5-500 mg, or about 50-500 mg, or about 100-500 mg, or about 200-1000 mg, or about 200-800 mg, or about 200-700 mg, or about 0.01 mg, or about 0.1 mg, or about 0.5 mg, or about 1 mg, or about 10 mg, or about 25 mg, or about 50 mg, or about 100 mg, or about 200 mg, or about 250 mg, or about 300 mg, or about 400 mg, or about 500 mg, or about 600 mg, or about 700 mg, or about 800 mg, or about 900 mg, or about 1000 mg. In some embodiments, compositions of the invention include nicotine, where nicotine is present in an amount from about 0.1-10 mg. In some embodiments, compositions of the invention include nicotine, where nicotine is present in an amount from about 0.1 to about 5 mg. In some embodiments, compositions of the invention include nicotine, where nicotine is present in an amount from about 0.1 to about 2.8 mg. In some embodiments, compositions of the invention include nicotine, where nicotine is present in an amount that is less than 3 mg. In some embodiments, compositions of the invention include nicotine, where nicotine is present in an amount from about 0.5 mg.

In exemplary embodiments, compositions of the invention include nicotine and levodopa, where nicotine is present in an amount from about 1-1000 mg, or about 10-1000 mg, or about 50-1000 mg, or about 100-1000 mg, or about 1-500 mg, or about 5-500 mg, or about 50-500 mg, or about 100-500 mg, or about 200-1000 mg, or about 200-800 mg, or about 200-700 mg, or about 1 mg, or about 10 mg, or about 25 mg, or about 50 mg, or about 100 mg, or about 200 mg, or about 250 mg, or about 300 mg, or about 400 mg, or about 500 mg, or about 600 mg, or about 700 mg, or about 800 mg, or about 900 mg, or about 1000 mg, and levodopa is present in an amount from 0.01 to 1000 mg, or about 0.1-800 mg, or about 0.1, 0.5, 1, 5, 10, 20, 50, 80, 100, 150, 200, 300, 400, or 500 mg.

In some embodiments, nicotine/levodopa is present at about 0.1/50 mg (nicotine/levodopa). In some embodiments, nicotine is present at about 0.5 mg and levodopa is present at about 50 mg. In some embodiments, nicotine is present at about 0.5 mg and levodopa is present at about 100 mg. In some embodiments, nicotine is present at about 0.5 mg and levodopa is present at about 150 mg. In some embodiments, nicotine is present at about 0.5 mg and levodopa is present at about 300 mg. In some embodiments, nicotine is present at about 0.5 mg and levodopa is present at about 1000 mg. In some embodiments, nicotine is present at about 1 mg and levodopa is present at about 50 mg. In some embodiments, nicotine is present at about 1 mg and levodopa is present at about 100 mg. In some embodiments, nicotine is present at about 1 mg and levodopa is present at about 150 mg. In some embodiments, nicotine is present at about 1 mg and levodopa is present at about 300 mg. In some embodiments, nicotine is present at about 1 mg and levodopa is present at about 1000 mg. In some embodiments, nicotine is present at about 5 mg and levodopa is present at about 50 mg. In some embodiments, nicotine is present at about 5 mg and levodopa is present at about 100 mg. In some embodiments, nicotine is present at about 5 mg and levodopa is present at about 150 mg. In some embodiments, nicotine is present at about 5 mg and levodopa is present at about 500 mg. In some embodiments, nicotine is present at about 1 mg and levodopa is present at about 50 mg.

In some embodiments, nicotine is present at about 0.5 mg and levodopa is present at about 100 mg. In some embodiments, nicotine is present at about 0.5 mg and levodopa is present at about 150 mg. In some embodiments, nicotine is present at about 0.5 mg and levodopa is present at about 500 mg. In some embodiments, nicotine is present at about 1 mg and levodopa is present at about 100 mg. In some embodiments, nicotine is present at about 1 mg and levodopa is present at about 150 mg. In some embodiments, nicotine is present at about 1 mg and levodopa is present at about 500 mg. In some embodiments, nicotine is present at about 7 mg and levodopa is present at about 50 mg. In some embodiments, nicotine is present at about 7 mg and levodopa is present at about 100 mg. In some embodiments, nicotine is present at about 7 mg and levodopa is present at about 150 mg. In some embodiments, nicotine is present at about 7 mg and levodopa is present at about 500 mg. In some embodiments, nicotine is present at about 10 mg and levodopa is present at about 100 mg. In some embodiments, nicotine is present at about 10 mg and levodopa is present at about 200 mg. In some embodiments, nicotine is present at about 10 mg and levodopa is present at about 300 mg. In some embodiments, levodopa is nicotine at about 10 mg and levodopa is present at about 1000 mg. In some embodiments, nicotine is present at about 14 mg and levodopa is present at about 50 mg. In some embodiments, nicotine is present at about 14 mg and levodopa is present at about 100 mg. In some embodiments, nicotine is present at about 14 mg and levodopa is present at about 150 mg. In some embodiments, nicotine is present at about 14 mg and levodopa is present at about 500 mg. In some embodiments, nicotine is present at about 21 mg and levodopa is present at about 50 mg. In some embodiments, nicotine is present at about 21 mg and levodopa is present at about 100 mg. In some embodiments, nicotine is present at about 21 mg and levodopa is present at about 150 mg. In some embodiments, nicotine is present at about 21 mg and levodopa is present at about 500 mg. In some embodiments, levodopa is present at an amount that is 100 percent to about 75% of the effective amount when levodopa is administered alone.

In another exemplary embodiment, compositions of the invention include nicotine, levodopa and carbidopa. In some embodiments, nicotine is present at about 0.5 mg, levodopa is present at about 25 mg, and carbidopa is present at about 100 mg. In some embodiments, nicotine is present at about 0.5 mg, levodopa is present at about 25 mg, and carbidopa is present at about 250 mg. In some embodiments, nicotine is present at about 0.5 mg, levodopa is present at about 12.5 mg, and carbidopa is present at about 50 mg. In some embodiments, nicotine is present at about 0.5 mg, levodopa is present at about 6.5 mg, and carbidopa is present at about 25 mg. In some embodiments, nicotine is present at about 0.5 mg, levodopa is present at about 12.5 mg, and carbidopa is present at about 125 mg. In some embodiments, nicotine is present at about 0.5 mg, levodopa is present at about 6.25 mg, and carbidopa is present at about 62.5 mg. In some embodiments, nicotine is present at about 0.5 mg, levodopa is present at about 12.5 mg, and carbidopa is present at about 125 mg. In some embodiments, nicotine is present at about 0.5 mg, levodopa is present at about 100 mg, and carbidopa is present at about 10 mg. In some embodiments, nicotine is present at about 0.5 mg, levodopa is present at about 100 mg, and carbidopa is present at about 25 mg. In some embodiments, nicotine is present at about 0.5 mg, levodopa is present at about 250 mg, and carbidopa is present at about 25 mg. In some embodiments, nicotine is present at about 1 mg, levodopa is present at about 25 mg, and carbidopa is present at about 100 mg. In some embodiments, nicotine is present at about 1 mg, levodopa is present at about 25 mg, and carbidopa is present at about 250 mg. In some embodiments, nicotine is present at about 1 mg, levodopa is present at about 12.5 mg, and carbidopa is present at about 50 mg. In some embodiments, nicotine is present at about 1 mg, levodopa is present at about 6.5 mg, and carbidopa is present at about 25 mg. In some embodiments, nicotine is present at about 1 mg, levodopa is present at about 12.5 mg, and carbidopa is present at about 125 mg. In some embodiments, nicotine is present at about 1 mg, levodopa is present at about 6.25 mg, and carbidopa is present at about 62.5 mg. In some embodiments, nicotine is present at about 1 mg, levodopa is present at about 100 mg, and carbidopa is present at about 10 mg. In some embodiments, nicotine is present at about 1 mg, levodopa is present at about 100 mg, and carbidopa is present at about 25 mg. In some embodiments, nicotine is present at about 1 mg, levodopa is present at about 250 mg, and carbidopa is present at about 25 mg. In some embodiments, nicotine is present at about 4 mg, levodopa is present at about 25 mg, and carbidopa is present at about 100 mg. In some embodiments, nicotine is present at about 7 mg, levodopa is present at about 25 mg, and carbidopa is present at about 250 mg. In some embodiments, nicotine is present at about 7 mg, levodopa is present at about 12.5 mg, and carbidopa is present at about 50 mg. In some embodiments, nicotine is present at about 7 mg, levodopa is present at about 6.5 mg, and carbidopa is present at about 25 mg. In some embodiments, nicotine is present at about 7 mg, levodopa is present at about 12.5 mg, and carbidopa is present at about 125 mg. In some embodiments, nicotine is present at about 7 mg, levodopa is present at about 6.25 mg, and carbidopa is present at about 62.5 mg. In some embodiments, nicotine is present at about 7 mg, levodopa is present at about 100 mg, and carbidopa is present at about 10 mg. In some embodiments, nicotine is present at about 7 mg, levodopa is present at about 100 mg, and carbidopa is present at about 25 mg. In some embodiments, nicotine is present at about 7 mg, levodopa is present at about 250 mg, and carbidopa is present at about 25 mg.

In liquid preparations, levodopa can be present at about 1-1000 mg/ml, or 1-500 mg/ml, or 1-200 mg/ml, or about 1, 5, 10, 20, 50, 50 or 100 mg/ml and nicotine at about 0.001-1000 mg/ml, or about 0.010-1000 mg/ml, or about 0.050-1000 mg/ml, or about 0.1-1000 mg/ml, or about 0.1-500 mg/ml, or about 0.05-500 mg/ml, or about 0.010-500 mg/ml, or about 0.001-500 mg/ml, or about 1-1000 mg/ml, or about 1-500 mg/ml, or about 1-200 mg/ml, or about 0.001 mg/ml, or about 0.025 mg/ml, or about 0.050 mg/ml, or about 0.1 mg/ml, or about 0.2 mg/ml, or about 0.25 mg/ml, or about 0.3 mg/ml, or about 0.4 mg/ml, or about 0.5 mg/ml, or about 0.6 mg/ml, or about 0.7 mg/ml, or about 0.8 mg/ml, or about 0.9 mg/ml, or about 1 mg/ml. At higher levels of nicotine, solubility can be enhanced by adjusting the type of diluent. In some embodiments, levodopa is present at an amount that is 100 percent to about 75% of the effective amount when levodopa is administered alone.

In some embodiments, a molar ratio of one or more of the dopaminergic agents to the nicotinic receptor modulator, e.g. an agonist such as nicotine can be 0.0001:1 to 1:1. Without limiting the scope of the invention, the molar ratio of one or more of the dopaminergic agents to the nicotinic receptor modulator, e.g. an agonist such as nicotine can be about 0.0001:1 to about 10:1, or about 0.001:1 to about 5:1, or about 0.01:1 to about 5:1, or about 0.1:1 to about 2:1, or about 0.2:1 to about 2:1, or about 0.5:1 to about 2:1, or about 0.1:1 to about 1:1. In some embodiments, levodopa is present at an amount that is 100 percent to about 75% of the effective amount when levodopa is administered alone.

Without limiting the scope of the present invention, the molar ratio of one or more of the dopaminergic agents to the nicotinic receptor agonist can be about $0.03 \times 10-5:1$, $0.1 \times 10-5:1$, $0.04 \times 10-3:1$, $0.03 \times 10-5:1$, $0.02 \times 10-5:1$, $0.01 \times 10-3:1$, $0.1 \times 10-3:1$, $0.15 \times 10-3:1$, $0.2 \times 10-3:1$, $0.3 \times 10-3:1$, $0.4 \times 10-3:1$, $0.5 \times 10-3:1$, $0.15 \times 10-2:1$, $0.1 \times 10-2:1$, $0.2 \times 10-2:1$, $0.3 \times 10-2:1$, $0.4 \times 10-2:1$, $0.5 \times 10-2:1$, $0.6 \times 10-2:1$, $0.8 \times 10-2:1$, 0.01:1, 0.1:1; or 0.2:1 per dose. In one embodiment, the dopaminergic agent is levodopa. In one embodiment, the nicotinic receptor agonist is nicotine.

Without limiting the scope of the present invention, the molar ratio of one or more of the dopaminergic agents to the nicotinic receptor modulator, e.g. an agonist such as nicotine can be about 0.001:1, 0.002:1, 0.003:1, 0.004:1, 0.005:1, 0.006:1, 0.007:1, 0.008:1, 0.009:1, 0.01:1, 0.02:1, 0.03:1, 0.04:1, 0.05:1, 0.06:1, 0.07:1, 0.08:1, 0.09:1, 0.1:1, 0.2:1, 0.3:1, 0.4:1, 0.5:1, 0.6:1, 0.7:1, 0.8:1, 0.9:1, 1:1, 2:1, 3:1, 4:1, or 5:1 per dose. In one embodiment, the dopaminergic agent is levodopa. In one embodiment, the nicotinic receptor agonist is nicotine.

A. Pharmaceutical Compositions

The nicotinic receptor modulators of the invention are usually administered in the form of pharmaceutical compositions. The drugs described above are also administered in the form of pharmaceutical compositions. When the nicotinic receptor modulators and the drugs are used in combination, both components may be mixed into a preparation or both components may be formulated into separate preparations to use them in combination separately or at the same time.

This invention therefore provides pharmaceutical compositions that contain, as the active ingredient, a nicotinic receptor modulator or a pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

This invention further provides pharmaceutical compositions that contain, as the active ingredient, a nicotinic receptor modulator or a pharmaceutically acceptable salt and/or coordination complex thereof, a dopaminergic agent or a pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The dopaminergic agent and/or the nicotinic receptor modulator may be prepared into pharmaceutical compositions in dosages as described herein (see, e.g., Compositions). Such compositions are prepared in a manner well known in the pharmaceutical art.

Pharmaceutical compositions for oral administration. In some embodiments, the invention provides a pharmaceutical composition for oral administration containing a nicotinic receptor modulator that reduces or eliminates a side effect of a dopaminergic agent, and a pharmaceutical excipient for oral administration. In some embodiments, the invention provides a pharmaceutical composition for oral administration containing a combination of a dopaminergic agent and a nicotinic receptor modulator that reduces or eliminates a side effect of the dopaminergic agent, and a pharmaceutical excipient suitable for oral administration. In some embodiments, the nicotinic receptor modulator that reduces or eliminates the side effect of the dopaminergic agent is a nicotinic receptor agonist, e.g. nicotine, as described elsewhere herein. In some embodiments, the nicotinic receptor modulator is present in amount to prevent addiction to the nicotinic receptor modulator.

In some embodiments, the invention provides a solid pharmaceutical composition for oral administration containing: (i) an effective amount of a nicotinic receptor modulator capable of reducing or eliminating one or more side effects of the dopaminergic agent; and (ii) a pharmaceutical excipient suitable for oral administration. In some embodiments, the nicotinic receptor modulator is present in amount to prevent addiction to the nicotinic receptor modulator.

In some embodiments, the invention provides a solid pharmaceutical composition for oral administration containing: (i) an effective amount of a dopaminergic agent; (ii) an effective amount of a nicotinic receptor modulator capable of reducing or eliminating one or more side effects of the dopaminergic agent; and (iii) a pharmaceutical excipient suitable for oral administration. In some embodiments, the nicotinic receptor modulator is present in amount to prevent addiction to the nicotinic receptor modulator.

In some embodiments, the composition further contains: (iv) an effective amount of a second dopaminergic agent. In some embodiments, the composition further contains: (iv) an effective amount of an agent such as carbidopa, which blocks the conversion of levodopa to dopamine in the blood. In some embodiments, the composition further contains: (iv) an effective amount of a COMT Inhibitor, such as entacapone. In some embodiments, the composition further contains: (iv) an effective amount of a monoamine oxidase type B (MAO-B) inhibitor such as selegiline. In some embodiments, the composition further contains: (iv) an effective amount of amantadine.

In some embodiments, the pharmaceutical composition may be a liquid pharmaceutical composition suitable for oral consumption.

In some embodiments, the dopaminergic agent is levodopa. In some embodiments, the dopaminergic agent is a dopamine agonist. In some embodiments, the nicotinic receptor modulator capable of reducing or eliminating one or more side effects of the dopaminergic agent is a nicotinic receptor agonist, e.g., nicotine.

In some embodiments, the invention provides a solid pharmaceutical composition for oral administration containing: (i) an effective amount of a nicotinic receptor agonist that is nicotine; and (ii) a pharmaceutical excipient suitable for oral administration. In some embodiments, the nicotinic receptor modulator is present in amount to prevent or reduce addiction to the nicotinic receptor modulator.

In some embodiments, the invention provides a solid pharmaceutical composition for oral administration containing: (i) an effective amount of a dopaminergic agent that is levodopa or a dopamine agonist; (ii) an effective amount of a nicotinic receptor agonist that is nicotine; and (iii) a pharmaceutical excipient suitable for oral administration. In some embodiments, the nicotinic receptor modulator is present in amount to prevent or reduce addiction to the nicotinic receptor modulator.

In some embodiments, the composition further contains (iv) an effective amount of a second dopaminergic agent. In some embodiments, the composition further contains: (iv) an effective amount of an agent such as carbidopa, which blocks the conversion of levodopa to dopamine in the blood. In some embodiments, the composition further contains: (iv) an effective amount of a COMT Inhibitor, such as entacapone. In some embodiments, the composition further contains: (iv) an effective amount of a monoamine oxidase type B (MAO-B) inhibitor such as selegiline. In some embodiments, the composition further contains: (iv) an effective amount of amantadine.

In some embodiments, the invention provides a solid pharmaceutical composition for oral administration containing an effective amount of levodopa, an amount of nicotine that is effective in reducing or eliminating a side effect of levodopa, and a pharmaceutically acceptable excipient. In some embodiments, the invention provides a liquid pharmaceutical composition for oral administration containing an effective amount of levodopa, an amount of nicotine that is effective in reducing or eliminating a side effect of levodopa, and a pharmaceutically acceptable excipient. In some embodiments, nicotine is present in amount to prevent or reduce addiction to nicotine.

In some embodiments, the invention provides a solid pharmaceutical composition for oral administration containing levodopa at about 40-800 mg, nicotine at about 0.01-200 mg and a pharmaceutically acceptable excipient. In some embodiments, the invention provides a solid pharmaceutical composition for oral administration containing levodopa at about 40-800 mg, nicotine at about 0.1-10 mg and a pharmaceutically acceptable excipient. In some embodiments, the invention provides a liquid pharmaceutical composition for oral administration containing levodopa at about 0.1-800 mg/ml, nicotine at about 0.005-100 mg/ml and a pharmaceutically acceptable excipient.

In some embodiments, the invention provides a solid pharmaceutical composition for oral administration containing an effective amount of levodopa, an effective amount of nicotine, and a pharmaceutically acceptable excipient, wherein the release of nicotine from said pharmaceutical composition reduces or eliminates a side effect of levodopa. In some embodiments, the invention provides a liquid pharmaceutical composition for oral administration containing an effective amount of levodopa, an effective amount of nicotine, and a pharmaceutically acceptable excipient, wherein the release of nicotine from said pharmaceutical composition reduces or eliminates a side effect of levodopa.

Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, microcrystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil. The tablets can be disintegrating tablets for fast release of the therapeutic agent.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10.

However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, preferred ionic surfactants include, by way of example: lecithins, lysolecithin, phospholipids, lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the dopaminergic agent and/or nicotinic receptor modulator and to minimize precipitation of the dopaminergic agent and/or nicotinic receptor modulator. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, $\epsilon$-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, $\epsilon$-caprolactone and isomers thereof, 6-valerolactone and isomers thereof, $\beta$-butyrolactone and isomers thereof; and other solubilizers known in the art, such as dimethyl acetamide, dimethyl isosorbide, N-methylpyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, antifoaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, disopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical compositions for injection In some embodiments, the invention provides a pharmaceutical composition for injection containing an agent that reduces or eliminate a side effect of a dopaminergic agent. In some embodiments, the invention provides a pharmaceutical composition for injection containing a combination of a dopaminergic agent and an agent that reduces or eliminates a side effect of the dopaminergic agent, and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the nicotinic receptor modulator and/or the dopaminergic agent in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Pharmaceutical compositions for topical (e.g. transdermal) delivery In some embodiments, the invention provides a pharmaceutical composition for transdermal delivery containing a nicotinic receptor modulator that reduces or eliminates a side effect of a dopaminergic agent, and a pharmaceutical excipient suitable for transdermal delivery. In some embodiments, the invention provides a pharmaceutical composition for transdermal delivery containing a combination of a dopaminergic agent and a nicotinic receptor modulator that reduces or eliminates a side effect of the dopaminergic agent, and a pharmaceutical excipient suitable for transdermal delivery. In some embodiments, the nicotinic receptor modulator that reduces or eliminates the side effect of the dopaminergic agent is a nicotinic receptor agonist, e.g. nicotine, as described elsewhere herein. Components and amounts of nicotinic receptor modulators in the compositions are as described herein.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another formulation for use in the methods of the present invention employs transdermal delivery devices (e.g. patches or minipumps). Such transdermal devices may be used to provide continuous or discontinuous infusion of the nicotinic receptor modulator in controlled amounts, either with or without dopaminergic agent. Thus, in some embodiments the invention provides a transdermal device incorporating a nicotinic receptor modulator, e.g., an agonist such as nicotine. In some embodiments the invention provides a transdermal device incorporating a nicotinic receptor modulator, e.g., an agonist such as nicotine in combination with a dopaminergic agent, e.g. levodopa.

The construction and use of transdermal devices for the delivery of pharmaceutical agents is well known in the art. See, e.g., U.S. Pat. Nos. 5,023,252, 4,992,445 and 5,001,139. Such devices may be constructed for continuous, pulsatile, or on demand delivery of pharmaceutical agents.

Pharmaceutical compositions for inhalation. Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other pharmaceutical compositions Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference herein in their entirety.

B. Kits

The invention also provides kits. The kits include a nicotinic receptor modulator that reduces or eliminates a side effect of a dopaminergic agent, in suitable packaging, and written material that can include instructions for use, discussion of clinical studies, listing of side effects, and the like. The kit may further contain a dopaminergic agent that has a side effect. In some embodiments, the dopaminergic agent and the nicotinic receptor modulator that reduces or eliminates a side effect of the dopaminergic agent are provided as separate compositions in separate containers within the kit. In some embodiments, the dopaminergic agent and the nicotinic receptor modulator that reduces or eliminates a side effect of the dopaminergic agent are provided as a single composition within a container in the kit. Suitable packaging and additional articles for use (e.g., measuring cup for liquid preparations, foil wrapping to minimize exposure to air, and the like) are known in the art and may be included in the kit.

Methods

In another aspect, the invention provides methods, including methods of treatment and methods of enhancing a therapeutic effect of a substance.

The term "animal" or "animal subject" as used herein includes humans as well as other mammals. The methods generally involve the administration of one or more drugs for the treatment of one or more diseases. Combinations of agents can be used to treat one disease or multiple diseases or to modulate the side-effects of one or more agents in the combination.

The term "treating" and its grammatical equivalents as used herein includes achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

In some embodiments, the invention provides a method of treating a condition by administering to an animal suffering from the condition an effective amount of a nicotinic receptor modulator sufficient to reduce or eliminate a side effect associated with a dopaminergic agent. In some embodiments, the nicotinic receptor modulator reduces or eliminates a plurality of side effects associated with the dopaminergic agent. In some embodiments the animal is a mammal, e.g., a human.

In some embodiments, the invention provides a method of treating a condition by administering to an animal suffering from the condition an effective amount of a dopaminergic agent and an amount of a nicotinic receptor modulator sufficient to reduce or eliminate a side effect of the dopaminergic agent. In some embodiments, the modulator reduces or eliminates a plurality of side effects of the dopaminergic agent. In some embodiments the animal is a mammal, e.g., a human.

The dopaminergic agent and the nicotinic receptor modulator are co-administered. "Co-administration," "administered in combination with," and their grammatical equivalents, as used herein, encompasses administration of two or more agents to an animal so that both agents and/or their metabolites are present in the animal at the same time. Co-administration includes simultaneous administration in separate compositions, administration at different times in separate compositions, or administration in a composition in which both agents are present. Thus, in some embodiments, the nicotinic receptor modulator and the dopaminergic agent are administered in a single composition. In some embodiments, the dopaminergic agent and the nicotinic receptor modulator are admixed in the composition. Typically, the dopaminergic agent is present in the composition in an amount sufficient to produce a therapeutic effect, and the nicotinic receptor modulator is present in the composition in an amount sufficient to reduce a side effect of the dopaminergic agent. In some embodiments, the dopaminergic agent is present in an amount sufficient to exert a therapeutic effect and the nicotinic receptor modulator is present in an amount sufficient to decrease a side effect of the dopaminergic agent by an average of at least about 5, 10, 15, 20, 25, 30, 40, 50, 60, 70, 80, 90, more than 90%, or substantially eliminate a side effect, compared to the effect without nicotinic receptor modulator. In some embodiments the dopaminergic agent and the nicotinic receptor modulator are co-administered to an individual every time than a therapeutic effect from said dopaminergic agent is desired in said individual. In some embodiment, co-administration comprises simultaneous administration of said dopaminergic agent and nicotine in the same dosage form or simultaneous administration in separate dosage forms. In some embodiments, the dopaminergic agent is present at an amount that is 100 percent to about 75% of the effective amount when the dopaminergic agent is administered alone.

In some embodiments, the dopaminergic agent is present in an amount sufficient to exert a therapeutic effect and the nicotinic receptor modulator is present in an amount sufficient to reduce or eliminate a side effect of the dopaminergic agent within at least about 1, 5, 10, 15, 20, 25, 30, 40, 50, 60, 70, 80, or 90 minutes after administration of the dopaminergic agent.

In some embodiments, the dopaminergic agent and/or the nicotinic receptor modulator are co-administered with an effective amount of an agent such as carbidopa, which blocks the conversion of levodopa to dopamine in the blood. In some embodiments, the dopaminergic agent and/or the nicotinic receptor modulator are co-administered with an effective amount of a COMT Inhibitor, such as entacapone. In some embodiments, the dopaminergic agent and/or the nicotinic receptor modulator are co-administered with an effective amount of a monoamine oxidase type B (MAO-B) inhibitor such as selegiline. In some embodiments, the dopaminergic agent and the nicotinic receptor modulator are co-administered with an effective amount of amantadine.

Administration of the dopaminergic agent and the nicotinic receptor modulator that reduces or eliminates at least one side effect of the dopaminergic agent may be any suitable means. If the agents are administered as separate compositions, they may be administered by the same route or by different routes. If the agents are administered in a single composition, they may be administered by any suitable route. In some embodiments, the agents are administered as a single composition by oral administration. In some embodiments, the agents are administered as a single composition by transdermal administration. In some embodiments, the agents are administered as a single composition by injection. In some embodiments the dopaminergic agent and the nicotinic receptor modulator are administered as a single composition to an individual every time than a therapeutic effect from said dopaminergic agent is desired in said individual. In some embodiments, the dopaminergic agent is present at an amount that is 100 percent to about 75% of the effective amount when the dopaminergic agent is administered alone. In some embodiments, the dopaminergic agent is administered in an amount sufficient to exert a therapeutic effect and the nicotinic receptor modulator is administered in an amount sufficient to reduce or eliminate a side effect of the dopaminergic agent within at least about 1, 5, 10, 15, 20, 25, 30, 40, 50, 60, 70, 80, or 90 minutes after administration of the dopaminergic agent.

In some embodiments, the nicotinic receptor modulator that reduces or eliminates a side effect of a dopaminergic agent is a nicotinic receptor agonist, nicotinic receptor agonists are as described herein. In some embodiments, nicotine is used. Dosages are as provided for compositions. Typically, the daily dosage of the nicotinic receptor modulator will be about 0.05 to about 100 mg/kg. In some embodiments, the daily dosage of the nicotinic receptor modulator is less than 93 mg per day.

The dopaminergic agent may be any dopaminergic agent described herein. In some embodiments, the dopaminergic agent is levodopa or a dopamine agonist, as described herein.

The methods of the invention may be used for treatments of any suitable condition where one or more dopaminergic agents are used that have side effects. Examples of conditions include, but are not limited to, Parkinson's disease, Alzheimer, dopa-responsive dystonia, cerebral palsy, postischemic contractile dysfunction, severe ovarian hyperstimulation syndrome, pediatric movement disorders and non-oliguric renal failure.

For example, in some embodiments, the methods of the invention include the treatment of Parkinson's disease patient to prevent dyskinesias by administering to an animal in need of treatment an effective amount of a dopaminergic agent, such as levodopa, and an effective amount of an agent that reduces or eliminates a dyskinesias induced by the dopaminergic agent.

In other embodiments, the methods of the invention include the treatment of postischemic contractile dysfunction by administering to an animal in need of treatment an effective amount of a dopaminergic agent, such as levodopa, and an effective amount of nicotinic receptor modulator that reduces or eliminates a side effect of the dopaminergic agent.

In yet other embodiments, the methods of the invention include the treatment of severe ovarian hyperstimulation syndrome by administering to an animal in need of treatment an effective amount of a dopaminergic agent, such as levodopa, and an effective amount of an agent that reduces or eliminates a side effect of the dopaminergic agent.

In other embodiments, the methods of the invention include the treatment of pediatric movement disorders by administering to an animal in need of treatment an effective amount of a dopaminergic agent, such as levodopa, and an effective amount of an agent that reduces or eliminates a side effect of the dopaminergic agent.

In some embodiments, the methods of the invention include the treatment of non-oliguric renal failure by administering to an animal in need of treatment an effective amount of a dopaminergic agent, such as levodopa, and an effective amount of an agent that reduces or eliminates a side effect of the dopaminergic agent.

When a dopaminergic agent and a nicotinic receptor modulator that reduces or eliminates a side effect of the dopaminergic agent are used in combination, any suitable ratio of the two agents, e.g., molar ratio, w/w ratio, w/v ratio, or v/v ratio, as described herein, may be used. In some embodiments, the dopaminergic agent is present at an amount that is 100 percent to about 75% of the effective amount when the dopaminergic agent is administered alone.

The invention further provides methods of reversing one or more side effects of a dopaminergic agent by administering nicotinic receptor modulator to an animal that has received an amount of the dopaminergic agent sufficient to produce one or more side effects. The methods are especially useful in a situation where it is desired to rapidly reverse one or more side effects of a dopaminergic agent. Any suitable nicotinic receptor modulator described herein may be used.

In some embodiments, the invention provides a method for reversing a side effect of a dopaminergic agent in a human by administering to the human an amount of a nicotinic receptor modulator sufficient to partially or completely reverse a side effect of the dopaminergic agent, where the human has received an amount of said dopaminergic agent sufficient to produce a side effect. In some embodiments, the human has received an overdose of the dopaminergic agent producing the side effect. In some embodiments, the nicotinic receptor modulator is an agonist, such as nicotine. Typically, the agonist will be administered by oral administration or transdermal delivery, in a dose sufficient to partially or completely reverse a side effect of the dopaminergic agent. In some embodiments, the agonist will be delivered by pulsatile delivery. In some embodiments, the agonist is administered in an amount sufficient to reduce or eliminate a side effect of the dopaminergic agent within at least about 1, 5, 10, 15, 20, 25, 30, 40, 50, 60, 70, 80, or 90 minutes after administration of the dopaminergic agent.

In another aspect, the invention includes method for the reducing dyskinesias comprising administering an animal suffering from dyskinesias an amount of a nicotinic receptor modulator sufficient to reduce the dyskinesias.

In some embodiments, the nicotinic receptor modulator is an agonist or an antagonist as described herein. In some embodiments, the nicotinic receptor agonist modulates a nicotinic receptor comprising at least one α subunit or a nicotinic receptor containing at least one α subunit and at least one β subunit. In some embodiments, the α subunit is selected from the group consisting of α2, α3, α4, α5, α6, α7, α8, α9, and α10 and the β subunit is selected from the group consisting of β2, β3 and β4. In some embodiments, the nicotinic receptor agonist modulates a nicotinic receptor composed of subunits selected from the group consisting of α4β2, α6β2, α4α6β2, α4α5β α4α6β2β3, α6β2β3 and α4α2β2. In some embodiments, the nicotinic receptor modulator modulates a nicotinic receptor comprising at least one αsubunit selected from the group consisting of α4, α6, and α7.

Administration

The methods involve the administration of a nicotinic receptor modulator, e.g., to reduce or eliminate a side effect of a dopaminergic agent. In some embodiments, a dopaminergic agent that produces a side effect is administered in combination with a nicotinic receptor modulator that reduces the effects of a side effect of the dopaminergic agent. In some embodiments, other agents are also administered, e.g., other dopaminergic agents or other therapeutic agent. When two or more agents are co-administered, they may be co-administered in any suitable manner, e.g., as separate compositions, in the same composition, by the same or by different routes of administration. In some embodiments, the nicotine receptor modulator and/or the dopaminergic agent are administered to the upper gastrointestinal tract of a subject.

In some embodiments, the nicotinic receptor modulator that reduces or eliminates a side effect of a dopaminergic agent is administered in a single dose. This may be the case where the agent is introduced into an animal to quickly lower the side effect of a dopaminergic agent already present in the body. Typically, such administration will be by injection, e.g., intravenous injection, in order to introduce the nicotinic receptor modulator quickly. However, other routes may be used as appropriate. A single dose of an agent that reduces or eliminates a side effect of a dopaminergic agent may also be used when it is administered with the dopaminergic agent (e.g., a dopaminergic agent that produces a side effect) for treatment of an acute condition.

In some embodiments, the nicotinic receptor modulator that reduces or eliminates a side effect of a dopaminergic agent is administered in multiple doses. Dosing may be about once, twice, three times, four times, five times, six times, or more than six times per day. Dosing may be about once a month, once every two weeks, once a week, or once every other day. In one embodiment the dopaminergic agent is levodopa. In another embodiment the dopaminergic agent and the nicotinic receptor modulator are administered together about once per day to about 6 times per day. In some embodiments, the nicotinic receptor modulator and the dopaminergic agent are administered to an individual every time than a therapeutic effect from said dopaminergic agent is desired in said individual. In another embodiment the administration of the dopaminergic agent and the nicotinic receptor modulator continues for less than about 7 days. In yet another embodiment the administration continues for more than about 6, 10, 14, 28 days, two months, six months, or one year. In some cases, continuous dosing is achieved and maintained as long as necessary. In some embodiments, the nicotinic receptor modulator that reduces or eliminates a side effect of a substance and/or dopaminergic agent is administered continually or in a pulsatile manner, e.g. with a minipump, patch or stent.

Administration of the nicotinic receptor modulator of the invention may continue as long as necessary. In some embodiments, an agent of the invention is administered for more than 1, 2, 3, 4, 5, 6, 7, 14, 28 days or 1 year. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic effects.

In some embodiments, a composition comprising a nicotinic receptor modulator is administered to an individual to reduce or eliminate a side effect of a dopaminergic agent in said individual, wherein the release of the nicotinic receptor modulator from a composition reduces or eliminates the side effect the dopaminergic agent. In some embodiments, in order to eliminate or reduce the side effects of a dopaminergic agent the nicotinic receptor modulator or a metabolite of the nicotinic receptor modulator can be present in the bloodstream prior to the dopaminergic agent. For example, this may be accomplished by administering the nicotinic receptor modulator separately from the dopaminergic agent or by administering the nicotinic receptor modulator and the dopaminergic agent in the same composition that is formulated so that the nicotinic receptor modulator reaches the bloodstream before the dopaminergic agent. For example, as desired a dosage form can be used wherein one active agent is immediate release and the other agent is slow/delayed release (e.g., bilayered tablet comprising both agents). Examples of multidrug dosage forms for differential release are known, such as disclosed in U.S. Pat. Nos. 7,011,849; 6,221,394; 5,073,380; 20070104787; 20060204578; 20060057202; 20050276852 and 20050266032.

In some embodiments, the nicotinic receptor modulator and/or the dopaminergic agent are formulated into orally disintegrating tablets that dissolve rapidly. These tablets can be swallowed with or without water. Examples of orally disintegrating tablets are known, such as disclosed in U.S. Pat. Nos. 7,282,217; 7,229,641; 6,368,625; 6,365,182; 6,221,392; and 6,024,981.

In some embodiments, the nicotinic receptor modulator or a metabolite of the nicotinic receptor modulator is in the blood 48, 36, 24, 12, 10, 8, 6, 5, 4, 3, 2, 1 hours before the dopaminergic agent. In other embodiments, the nicotinic receptor modulator or a metabolite of the nicotinic receptor modulator is in the blood stream 59, 50, 40, 35, 30, 25 20, 10, 5, 4, 3, 2, 1 minutes before the dopaminergic agent.

In another aspect of the invention, in order to eliminate or reduces the side effects of a dopaminergic agent the nicotinic receptor modulator or a metabolite of the nicotinic receptor modulator may be in the bloodstream after the dopaminergic agent. This may be accomplished by administering the nicotinic receptor modulator separately from the dopaminergic agent or by administering the nicotinic receptor modulator and the dopaminergic agent in the same composition that is formulated so that the nicotinic receptor modulator reaches the bloodstream after the dopaminergic agent.

In some embodiments, the nicotinic receptor modulator or a metabolite of the nicotinic receptor modulator is present in the blood 48, 36, 24, 12, 10, 8, 6, 5, 4, 3, 2, 1 hours after the dopaminergic agent. In some embodiments, the nicotinic receptor modulator or a metabolite of the nicotinic receptor modulator is in the blood stream 59, 50, 40, 35, 30, 25 20, 10, 5, 4, 3, 2, 1 minutes after the dopaminergic agent.

In one embodiment, nicotinic receptor modulator or a metabolite has a second plasma half-life that differs from the first plasma half-life by at least about 3 hours, wherein a dosage form administered provides a plasma concentration within a therapeutic range of the dopaminergic agent over a period which is coextensive with at least about 70% of a period over which the dosage form provides a plasma concentration within a therapeutic range of nicotinic receptor modulator or a metabolite. In some embodiments the nicotinic receptor modulator or a metabolite and the dopaminergic agent have a similar half-life. In some embodiments, the half life of the nicotinic receptor modulator or a metabolite of the nicotinic receptor modulator is 48, 36, 24, 12, 10, 8, 6, 5, 4, 3, 2, 1.5, 1 hours.

In some embodiments, a dosage form of the invention comprises a multi-layered tablet. In one embodiment, a dosage form of the invention comprises a bi-layered tablet which comprises a first layer and a second layer, the first layer comprising nicotinic receptor modulator or a metabolite and has a first plasma half-life, and the second layer comprising the dopaminergic agent which has a second plasma half-life that differs from the first plasma half-life by at least about 3 hours, wherein the bi-layered tablet provides a plasma concentration within a therapeutic range of the dopaminergic agent over a period which is coextensive with at least about 70% of a period over which the bi-layered tablet provides a plasma concentration within a therapeutic range of the nicotinic receptor modulator or a metabolite.

In yet other embodiments, the second and first plasma half-life differ by at least 48, 36, 24, 12, 10, 8, 6, 5, 4, 3, 2, or 1 hour. In some embodiments the second and first plasma half-life are similar.

In some embodiments, the invention includes a multilayer tablet comprising an immediate release layer and a sustained release layer. In some embodiments, the immediate release layer comprises a nicotinic receptor modulator or a metabolite and the sustained release layer comprises a dopaminergic agent. In some embodiments, the immediate release layer comprises one or more therapeutic agents independently selected from the group consisting of nicotinic receptor agonist and dopaminergic agent, and the sustained release layer comprises one or more therapeutic agents independently selected from the group consisting of nicotinic receptor agonist and dopaminergic agents. In some embodiments, the immediate release layer comprises a dopaminergic agent and the sustain release layer comprises a nicotinic receptor modulator or a metabolite. In some embodiments, the immediate release layer or the sustained release layer comprises a third therapeutic agent such as the ones described herein. Examples of agents include, but are not limited to, amantadine, carbidopa and entacapone.

An effective amount of a nicotinic receptor modulator and/or an effective amount of a dopaminergic agent may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent.

In some embodiments, an effective amount of a nicotinic receptor modulator is administered such that the nicotinic receptor modulator reaches a critical concentration in the bloodstream, plasma, or the tissue where the side effect need to be eliminated, wherein the critical concentration is the concentration necessary to reduce or eliminate the dopaminergic agent induced-side effect. Examples of different forms of administration include, but are not limited to, administration in a single dose, multiple doses or through pulsatile administration. In some embodiments, after the nicotinic receptor modulator or a metabolite of the nicotinic receptor modulator has reduced or eliminated the dopaminergic agent induced-side effect, the concentration of the nicotine receptor modulator or a metabolite of the nicotine receptor modulator will decrease at the site of side effects occur (e.g., systemically, such as in the bloodstream; or the tissue where the side effect occurs).

In some embodiments, the nicotinic receptor modulator is administered such that the nicotinic receptor modulator or a metabolite of a receptor modulator reaches a critical concentration in the bloodstream, plasma or tissue where the side effect needs to be eliminated 48, 36, 24, 12, 10, 8, 6, 5, 4, 3, 2, 1 hours before the dopaminergic agent reaches the bloodstreams or the tissue where the side effects are generated. In some embodiments, the nicotinic receptor modulator is administered such that the nicotinic receptor modulator or a metabolite of the nicotinic receptor modulator reaches a critical concentration in the bloodstream, plasma or tissue where the side effect needs to be eliminated 59, 50, 40, 35, 30, 25 20, 10, 5, 4, 3, 2, 1 minutes before the dopaminergic agent reaches the bloodstreams or the tissue where the side effects are generated.

In some embodiments, the nicotinic receptor modulator is administered such that the nicotinic receptor modulator or a metabolite of a receptor modulator reaches a critical concentration in the bloodstream, plasma or tissue where the side effect needs to be eliminated 48, 36, 24, 12, 10, 8, 6, 5, 4, 3, 2, 1 hours after the dopaminergic agent reaches the bloodstreams or the tissue where the side effects are generated. In some embodiments, the nicotinic receptor modulator is administered such that the nicotinic receptor modulator or a metabolite of the nicotinic receptor modulator reaches a critical concentration in the bloodstream, plasma or tissue where the side effect needs to be eliminated 59, 50, 40, 35, 30, 25 20, 10, 5, 4, 3, 2, 1 minutes after the dopaminergic agent reaches the bloodstream, plasma or the tissue where the side effects are generated.

In some embodiments, the nicotinic receptor modulator is administered such that a critical concentration of the nicotinic receptor modulator and or a metabolite of the nicotinic receptor modulator is reached in the bloodstream, plasma or a tissue where the side effect needs to be eliminated when the side effect reaches a peak. In some embodiments, is administered such that a critical concentration of the nicotinic receptor modulator and or a metabolite of the nicotinic receptor modulator is reached in the bloodstream, plasma or a tissue where the side effect needs to be eliminated 48, 36, 24, 12, 10, 8, 6, 5, 4, 3, 2, 1 hours before the side effect eliminated reaches a peak. In some embodiments, is administered such that a critical concentration of the nicotinic receptor modulator and or a metabolite of the nicotinic receptor modulator is reached in the bloodstream, plasma or a tissue where the side effect needs to be eliminated 59, 50, 40, 35, 30, 25 20, 10, 5, 4, 3, 2, 1 minutes before the side effect eliminated reaches a peak.

In some embodiment, the critical concentration of the nicotinic receptor modulator or a nicotinic receptor modulator metabolite is about 1 pg/ml to about 1 mg/ml. In some embodiments the critical concentration nicotinic receptor modulator or nicotinic receptor modulator metabolite is about 1 pg/ml to about 1 ng/ml, or about 50 pg/ml to about 1 ng/ml, or about 100 pg/ml to about 1 ng/ml, or about 500 pg/ml to about 1 ng/ml, or about 1 ng/ml to about 500 ng/ml, or about 10 ng/ml to about 500 ng/ml, or about 100 ng/ml to about 500 ng/ml, or about 200 ng/ml to about 500 ng/ml, or about 300 ng/ml to about 500 ng/ml, or about 400 ng/ml to about 500 ng/ml, or about 500 ng/ml to about 1 ug/ml, or about 600 ng/ml to about 1 ug/ml, or about 700 ng/ml to about 1 ug/ml, or about 800 ng/ml to about 1 ug/ml, or about 900 ng/ml to about 1 ug/ml, or about 1 ug/ml to about 1 mg/ml, or about 10 ug/ml to about 1 mg/ml, or about 100 ug/ml to about 1 mg/ml, or about 500 ug/ml to about 1 mg/ml, or about 600 ug/ml to about 1 mg/ml, or about 700 ug/ml to about 1 mg/ml, or about 800 ug/ml to about 1 mg/ml, or about 900 ug/ml to about 1 mg/ml. In some embodiment, the critical concentration of the nicotinic receptor modulator or a nicotinic receptor modulator metabolite is about 200 ng/ml to about 420 ng/ml. In some embodiment, the critical concentration of the nicotinic receptor modulator or a nicotinic receptor modulator metabolite is about 1 ng/ml to about 20 ng/ml. In some embodiment, the critical concentration of the nicotinic receptor modulator or a nicotinic receptor modulator metabolite is about 1 ng/ml to about 5 ng/ml. In some embodiment, the critical concentration of the nicotinic receptor modulator or a nicotinic receptor modulator metabolite is about 20 ng/ml to about 100 ng/ml.

In some embodiments, the nicotinic receptor modulator is administered such that the nicotinic receptor modulator or a metabolite reduce or eliminate a side effect of a dopaminergic agent within at least about 1, 5, 10, 15, 20, 25, 30, 40, 50, 60, 70, 80, or 90 minutes after administration of the dopaminergic agent.

The nicotinic receptor modulator and the dopaminergic agent may be administered in dosages as described herein (see, e.g., Compositions). Dosing ranges for dopaminergic agents are known in the art. It is also known in the art that due to intersubject variability in dopaminergic agents, such as levodopa, pharmacokinetics, individualization of dosing regimen is necessary for optimal therapy. Dosing for the nicotinic receptor modulator may be found by routine experimentation. For an nicotinic receptor agonist, e.g., nicotine, typical daily dose ranges are, e.g. about 1-5000 mg, or about 1-3000 mg, or about 1-2000 mg, or about 1-1000 mg, or about 1-500 mg, or about 1-100 mg, or about 10-5000 mg, or about 10-3000 mg, or about 10-2000 mg, or about 10-1000 mg, or about 10-500 mg, or about 10-200 mg, or about 10-100 mg, or about 20-2000 mg or about 20-1500 mg or about 20-1000 mg or about 20-500 mg, or about 20-100 mg, or about 50-5000 mg, or about 50-4000 mg, or about 50-3000 mg, or about 50-2000 mg, or about 50-1000 mg, or about 50-500 mg, or about 50-100 mg, about 100-5000 mg, or about 100-4000 mg, or about 100-3000 mg, or about 100-2000 mg, or about 100-1000 mg, or about 100-500 mg. In some embodiments, the daily dose of nicotine is about 1, 5, 10, 15, 20, 25, 30, 35, 40, 45, 50, 100, 200, 300, 400, 500, 600, 700, 800, 900, or 1000 mg. In some embodiments, the daily dose of nicotine is 0.9 mg. In some embodiments, the daily dose of nicotine is 1.8 mg. In some embodiments, the daily dose of nicotine is 2.4 mg. In some embodiments, the daily dose of nicotine is 3 mg. In some embodiments, the daily dose of nicotine is 6 mg. In some embodiments, the daily dose of nicotine is 7 mg. In some embodiments, the daily dose of nicotine is 8 mg. In some embodiments, the daily dose of nicotine is 9 mg. In some embodiments, the daily dose of nicotine is 12 mg. In some embodiments, the daily dose of nicotine is 14 mg. In some embodiments, the daily dose of nicotine is 18 mg. In some embodiments, the daily dose of nicotine is 21 mg. In some embodiments, the daily dose of nicotine is 24 mg. In some embodiments, the daily dose of nicotine is 32 mg. In some embodiments, the daily dose of nicotine is 50 mg. In some embodiments, the daily dose of nicotine is less than 93 mg. Daily dose range may depend on the form of nicotinic receptor agonist and/or factors with which the nicotinic receptor agonist is administered, as described herein.

In some embodiment the daily dose of nicotine is such that the plasma level of nicotine or a nicotine metabolite is about 1 pg/ml to about 1 mg/ml. In some embodiments the daily dose of nicotine is such that the plasma level or nicotine or nicotine metabolite is about 1 pg/ml to about 1 ng/ml, or about 50 pg/ml to about 1 ng/ml, or about 100 pg/ml to about 1 ng/ml, or about 500 pg/ml to about 1 ng/ml, or about 1 ng/ml to about 500 ng/ml, or about 10 ng/ml to about 500 ng/ml, or about 100 ng/ml to about 500 ng/ml, or about 200 ng/ml to about 500 ng/ml, or about 300 ng/ml to about 500 ng/ml, or about 400 ng/ml to about 500 ng/ml, or about 500 ng/ml to about 1 ug/ml, or about 600 ng/ml to about 1 ug/ml, or about 700 ng/ml to about 1 ug/ml, or about 800 ng/ml to about 1 ug/ml, or about 900 ng/ml to about 1 ug/ml, or about 1 ug/ml to about 1 mg/ml, or about 10 ug/ml to about 1 mg/ml, or about 100 ug/ml to about 1 mg/ml, or about 500 ug/ml to about 1 mg/ml, or about 600 ug/ml to about 1 mg/ml, or about 700 ug/ml to about 1 mg/ml, or about 800 ug/ml to about 1 mg/ml, or about 900 ug/ml to about 1 mg/ml. In some embodiment, the daily dose of nicotine is such that the plasma level of nicotine or a nicotine metabolite is about 200 ng/ml to about 420 ng/ml. In some embodiment, the daily dose of nicotine is such that the plasma level of nicotine or a nicotine metabolite is about 1 ng/ml to about 20 ng/ml. In some embodiment, the daily dose of nicotine is such that the plasma level of nicotine or a nicotine metabolite is about 1 ng/ml to about 5 ng/ml. In some embodiment, the daily dose of nicotine is such that the plasma level of nicotine or a nicotine metabolite is about 20 ng/ml to about 100 ng/ml.

When a nicotinic receptor modulator, e.g., an agonist such as nicotine, is administered in a composition that comprises one or more dopaminergic agents and the dopaminergic agent has a shorter half-life than nicotinic receptor modulator, unit dose forms of the dopaminergic agent and the nicotinic receptor modulator may be adjusted accordingly.

EXAMPLES

Example 1

Nicotine Reduced Levodopa-Induced Dyskinesias in Monkeys with Nigrostriatal Damage Materials and Methods Animals: Squirrel (*Saimiri sciureus*) monkeys (n=7) were purchased from World Wide Primates (Miami, Fla.). The animals weighed between 0.6-0.9 kg and were in mid to late adulthood as determined from their general appearance (dentition, fur, other). Female monkeys were used since older animals were available that may better model Parkinson's disease. The animals were placed in quarantine upon arrival, and maintained in a temperature-controlled room (27±3° C.) with a relative humidity>30%, under a 13/11-hour light/dark cycle. Monkey food chow and fruits/vegetables were provided once daily, with water provided ad libitum. The monkeys were housed in separate cages to allow for clear behavioral assessments. The animals were released from quarantine after 1 month and treatments initiated. All procedures conformed to the National Institutes of Health Guide for the Care and Use of Laboratory Animals and were approved by the Institutional Animal Care and Use Committee at the Parkinson's Institute.

1-Methyl-4-phenyl-1,2,3,6-tetrahydropyridine (MPTP) administration: Prior to lesioning, the animals were allowed to acclimate to the colony and rated for parkinsonism as described (Langston et al. Ann Neurol. 2000; 47:S79-89). All values were within the normal range. The monkeys were then injected subcutaneously with 2.0 mg/kg MPTP (Sigma, St-Louis, Mo.) dissolved in saline. The animals were rated for parkinsonism 3-4 weeks after MPTP administration. The disability scores ranged from 0 (normal) to 28 for a severely parkinsonian animal. Animals were assessed for 1) spatial hypokinesia (reduction in use of the available cage space), 2) body bradykinesia (increased slowness in body movement), 3) left and 4) right manual dexterity, 5) balance, 6) freezing and 7) action tremor. If they were not parkinsonian, MPTP injection (1.0-2.0 mg/kg) was repeated from 2-5 times for total doses of 3.5 to 13.5 mg/kg. Despite multiple MPTP dosing, two of the animals were not stably parkinsonian. These two monkeys did exhibit reliable dyskinesias in response to levodopa treatment.

Nicotine treatment: All monkeys (n=7) were then given a drinking solution for 3 weeks consisting of commercially available orange Gatorade® to mask nicotine's bitter taste (FIG. 1). The control group (n=4) was continued on Gatorade® only, while nicotine (free base) was added to the Gatorade of the treated group (n=3). Nicotine dosing was started at 50 μg/ml for 1 week, 150 μg/ml for 1 week, with the concentration increased by 150 μg increments/week over the next few weeks, up to 650 μg/ml (FIG. 1). Since the animals were relatively old and exhibited poor dentition, the dried food pellets were softened with ~25 ml of either Gatorade® or the nicotine-Gatorade® (for the treated animals) to ensure adequate nicotine intake. There were no significant effects of nicotine treatment on body weight or fluid intake, and the monkeys appeared in good health.

Levodopa administration: Monkeys were administered levodopa/carbidopa (5 mg/kg and 1.25 mg/kg, respectively), prepared by crushing a tablet of Sinemet® CR 100/25 (Du-Pont Pharma) and dissolving it in water. This dose of levodopa is within the range of that prescribed to Parkinson's disease patients. The monkeys were gavaged twice daily at 3.5-hour intervals for 8 weeks at a time using a 5-day-on/2-day-off schedule (Hsu et al., J Pharmacol Exp Ther. 2004; 311:770-777). During levodopa treatment, the monkeys were given fruits in the morning and food pellets 3.5 hours after the afternoon levodopa dose to optimize gastrointestinal absorption.

Dyskinesias were rated from videotapes, as described (Hsu et al., J Pharmacol Exp Ther. 2004; 311:770-777). This included a one hour baseline period (no drugs) from ~8:00-9:00 AM, followed by two 3.5-hour treatment periods with levodopa starting at ~9:00 AM and ~12:30 PM. Dyskinesias were rated for 2-minute periods at 30-minute intervals by two independent raters blinded to treatment. They were rated on a scale of 0 (no dyskinesias) to 4; a score of 1 was indicative of subtle dyskinesias that were not sustained; 2, mild dyskinesias that were sustained; 3, moderate dyskinesias that impaired the ability to remain stationary; 4, severe dyskinesias that were generalized and incapacitating.

Data analyses: The levodopa treatment protocol used in the present study involved a 5-day-on/2-day-off schedule. Parkinsonian ratings were done on Monday and Friday of each week, with the score averaged over the two days. Dyskinesias ratings were determined by averaging the scores on Wednesday and Thursday of each week. All values are expressed as the mean±SE of the indicated number of animals. Results were compared using paired t-tests or analysis of variance (ANOVA) followed by Bonferroni multiple comparison post hoc test, using Prism® program (GraphPad Software, Inc, San Diego, Calif.). A level of 0.05 was considered significant.

Measurement of plasma cotinine levels: Plasma cotinine, a major (75%) nicotine metabolite, was measured as an index of nicotine intake (Hukkanen et al., Pharmacol Rev. 2005; 57:79-115 and Matta et al., Psychopharmacology (Berl). 2007; 190:269-319). Blood (1-2 ml) was drawn from the femoral vein under ketamine sedation (15-20 mg/kg intramuscularly) at ~3 PM. The blood samples were centrifuged at 1,000×g for 12 minutes, and the plasma stored at −80° C. Plasma cotinine levels were measured using an ELISA kit (OraSure Technologies Inc, Bethleham, Pa.). Plasma cotinine levels were 303+25 (n=7), and fell within the range observed in cigarette smokers (Hukkanen et al., Pharmacol Rev. 2005; 57:79-115 and Matta et al., Psychopharmacology (Berl). 2007; 190:269-319).

Results

Figure 2:
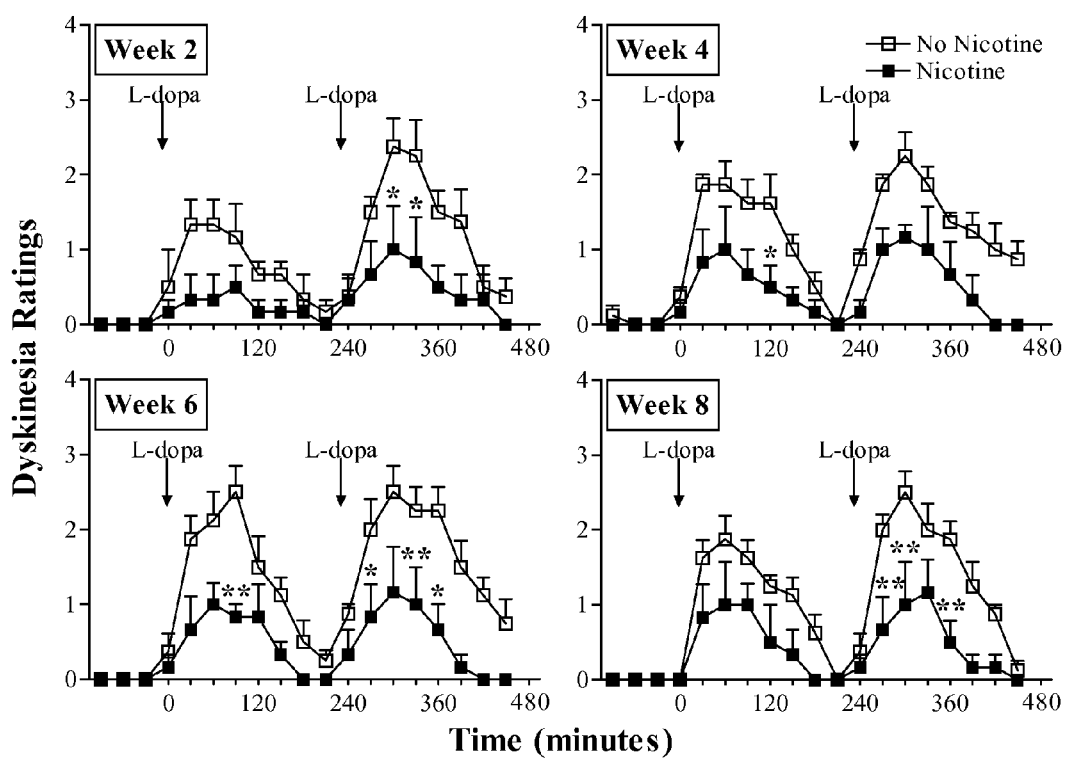
FIG. 2 depicts a time course of the nicotine-induced decline in L-dopa-induced dyskinesias.

Time course of the nicotine-induced decline in levodopa-induced dyskinesias in monkeys with nigrostriatal damage: Nicotine treatment (n=3) resulted in a reduction in levodopa-induced dyskinesias over the course of the day as compared to non-nicotine-treated animals (n=4). This decline was observed over the entire 8-week period investigated, with the data for weeks 2, 4, 6 and 8 depicted in FIG. 2. In monkeys not receiving nicotine, dyskinesias developed rapidly following levodopa administration, were maximal after 30-90 minutes, and declined over the remaining two hours (FIG. 2). Dyskinesias were significantly reduced in nicotine-treated animals compared to monkeys not receiving nicotine. For instance at 8 weeks, ANOVA yielded a significant main effect of nicotine treatment (F[1, 80]=54.24, p<0.0001). There also was a significant main effect of time (F[15, 80]=8.95, p<0.0001).

Figure 3:
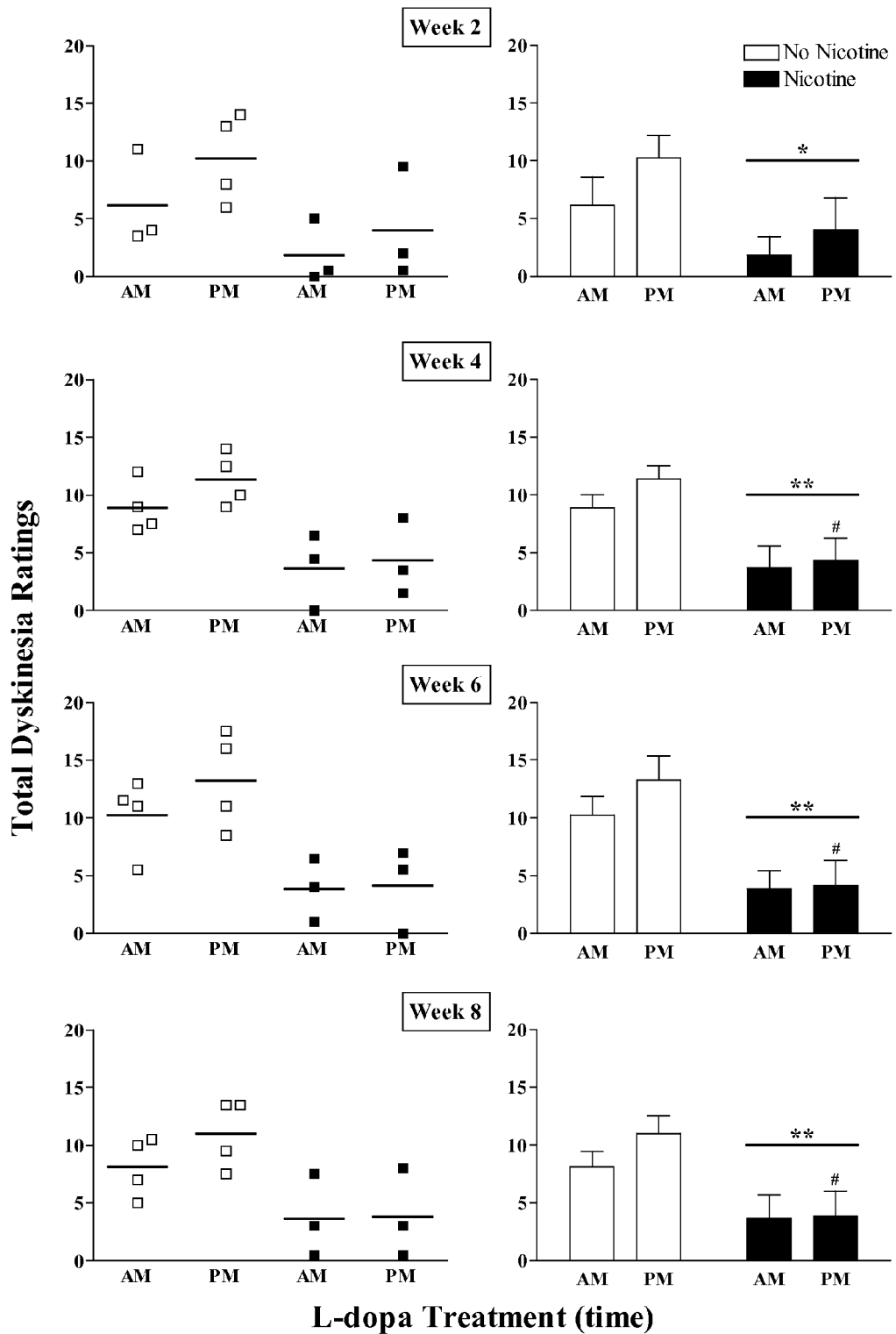
FIG. 3 depicts that overall dyskinesias were decreased by nicotine treatment.

Decline in total dyskinesias in monkeys receiving nicotine treatment: It was next examined the effect of nicotine treatment on the total dyskinetic response by evaluating the area under the curve of the time course. A significant decrease was observed in nicotine-treated animals at all time points compared to monkeys not receiving nicotine (FIG. 3). For instance at the 8 week time point, there was a significant main effect of nicotine by ANOVA (F[1, 10]=11.41, p=0.007), with no effect of time.

Figure 4:
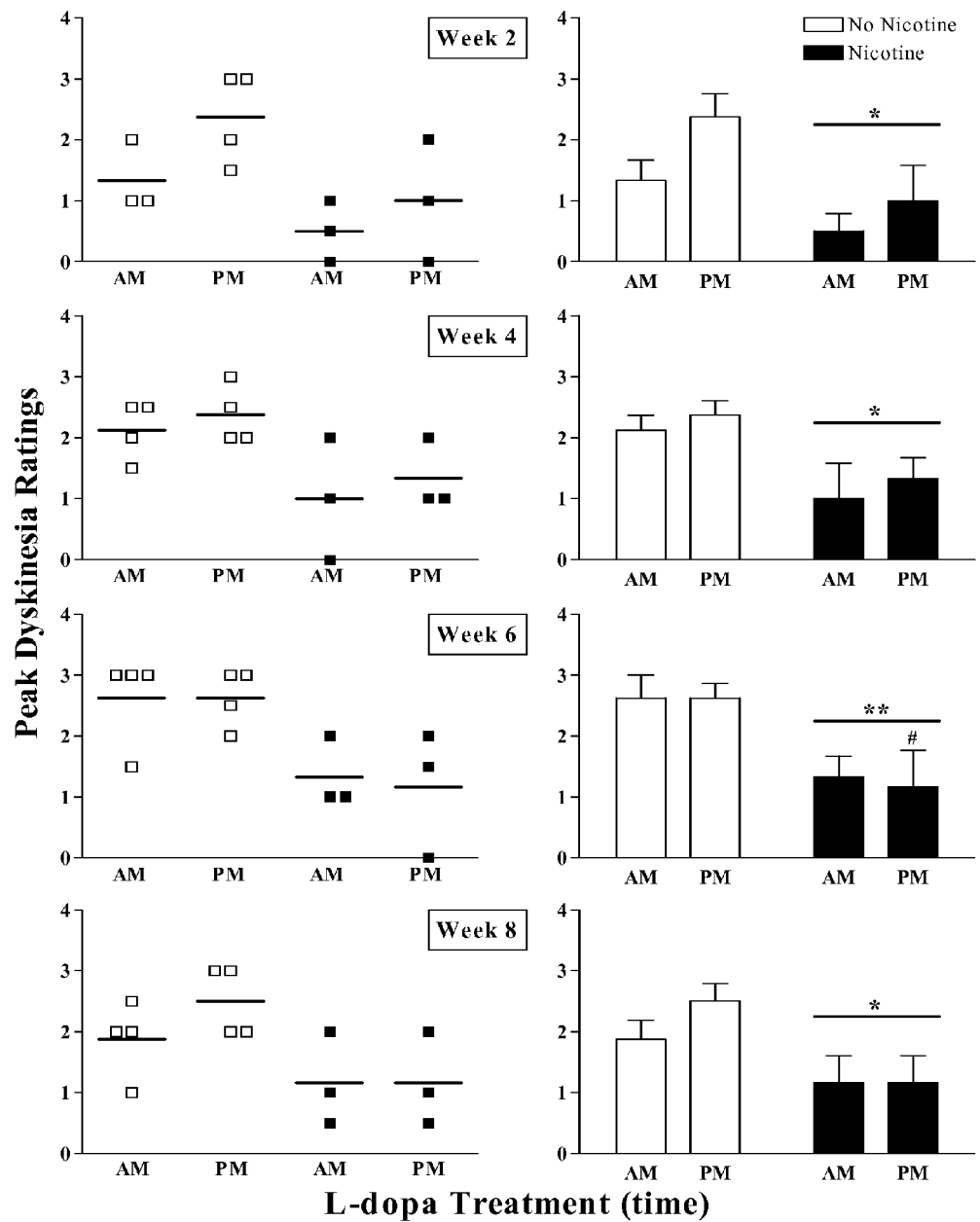
FIG. 4 depicts a graph showing that nicotine treatment decreased peak dyskinesias.

Nicotine treatment decreases peak dose dyskinesias: Peak dyskinesias, defined as the maximal dyskinetic score during the morning or afternoon, were decreased throughout the 8-week levodopa treatment period in nicotine-treated animals compared to control (FIG. 4). For instance at 8 weeks, there was a significant main effect of nicotine by ANOVA (F[1, 10]=7.90, p=0.0184), with no main effect of time.

Nicotine shortened the duration of dyskinesias: Dyskinesias were still evident in the non-nicotine-treated monkeys 3 hours after the second daily levodopa administration, but not in animals treated with nicotine (FIG. 2, Table 1). ANOVA showed there was a main effect of nicotine treatment (F [1, 20]=18.33, p=0.0004), but not time indicating no difference across the 8-week rating period (Table 1).

TABLE 1

Nicotine administration shortens the duration of levodopa-induced dyskinesias

| Nicotine Treatment | N | Week of levodopa treatment | | | |
|---|---|---|---|---|---|
| | | 2/3 | 4 | 6 | 8 |
| No | 4 | 0.5 ± 0.3 | 1.0 ± 0.4 | 1.1 ± 0.2 | 0.9 ± 0.1 |
| Yes | 3 | 0.3 ± 0.3 | 0* | 0* | 0.2 ± 0.2 |

Each value is the mean ± SE of dyskinetic ratings 3 hours after the afternoon levodopa treatment.
*p < 0.05 as compared to no nicotine treatment using ANOVA followed by a Bonferroni post-hoc test.

Example 2

Nicotine Reduced Dyskinesias in Levodopa-Primed Monkeys

Materials and Methods

Materials and methods were the same as in example 1.

Results

Crossover study: The data depicted in FIG. 2-4 and Table 1 clearly showed that nicotine administration attenuated levodopa-induced dyskinesias. A crossover study, was then conducted, in which the animals originally receiving nicotine were given vehicle (n=3), while the vehicle-treated animals were now administered nicotine (n=4). Levodopa treatment was stopped. The concentration of nicotine was gradually increased in the drinking water (see FIG. 1) to 650 µg/ml, at which the animals were maintained for 4 weeks. Monkeys that had previously received nicotine were placed on vehicle drinking water for the same time period. All monkeys were then treated with levodopa (5 mg/kg, twice daily 3.5 hours apart) for a subsequent 8-week period. Since both groups of monkeys had previously received levodopa, they were termed levodopa-primed.

Figure 5:
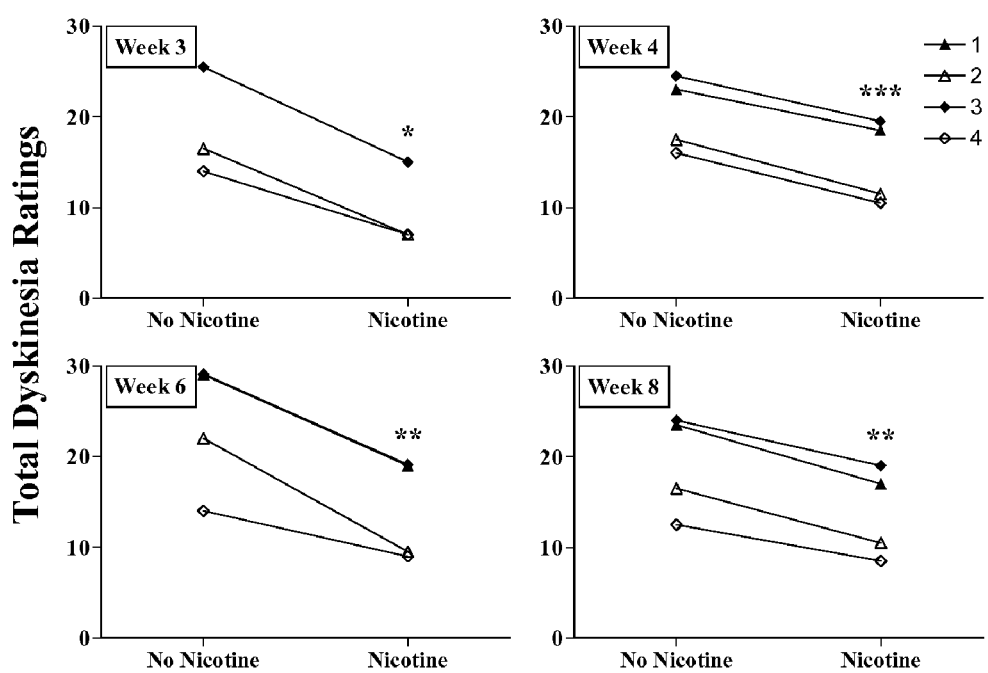
FIG. 5 depicts graphs showing that nicotine administration decreased total levodopa-induced dyskinesias in levodopa-primed monkeys.

Nicotine administration decreased levodopa-induced dyskinesias in levodopa-primed monkeys: For these analyses, the ratings obtained for each animal on the new treatment were compared to the score of the same animal in the previous treatment period, that is, prior to crossover. The results in FIG. 5 show that nicotine administration significantly reduced total dyskinesias at all time points using paired t-tests. Analyses of the dyskinetic time course also showed a main effect of nicotine throughout levodopa treatment by ANOVA (for example, week 8, F[1, 114]=15.89, p=0.0001). Peak dyskinesias were significantly reduced during the last 4 weeks of levodopa treatment (week 6, p=0.0354; and week 8, p=0.0138 by paired t-tests). There was also a decrease in the duration of dyskinesias with nicotine treatment, with a significant main effect of nicotine by ANOVA (F [1, 24]=18.00, p=0.0003). Thus, nicotine administration reduced levodopa-induced dyskinesias in animals previously exposed to levodopa.

Figure 6:
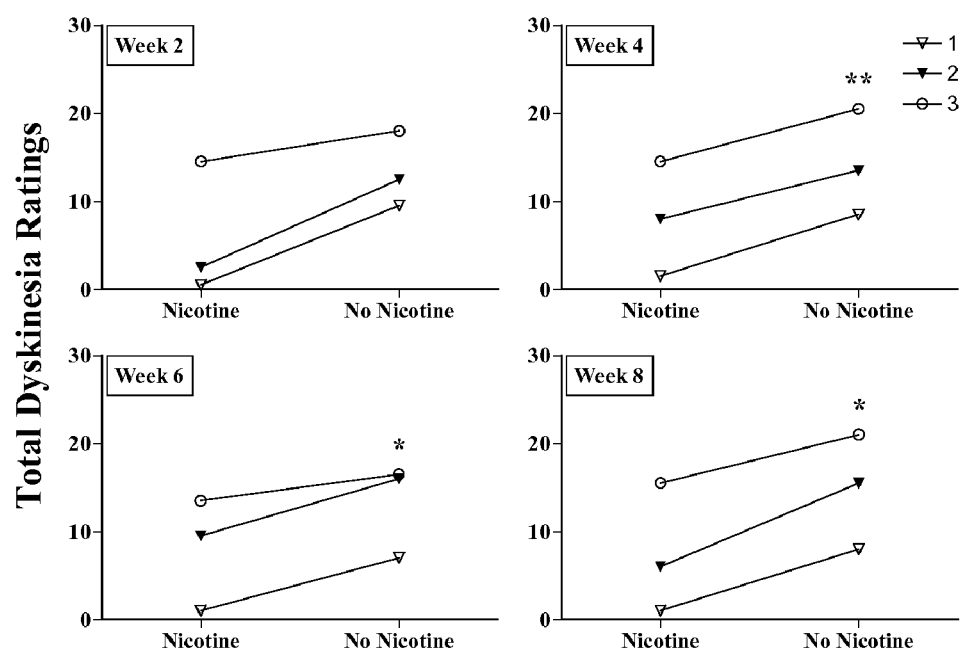
FIG. 6 depicts graphs showing that removal of nicotine increased levodopa-induced dyskinesias in levodopa-primed monkeys.

Removal of nicotine increases levodopa-induced dyskinesias in levodopa-primed monkeys: By contrast, in animals removed from nicotine treatment, total dyskinetic scores were significantly enhanced at week 4, 6 and 8 of levodopa treatment (FIG. 6). Analyses of the time course of dyskinesias also showed an increase in dyskinesias over the 8-week levodopa treatment, with ANOVA yielding a significant main effect of nicotine (for example, week 8, F [1, 76]=15.94, p=0.0001). In addition, there was a significant increase in the duration of dyskinesia assessed 3 hours after the afternoon levodopa dose, with a significant main effect of nicotine by two-way ANOVA (F [1, 16]=5.33, p=0.0346). Thus, removal of nicotine enhanced levodopa-induced dyskinesias.

Figure 7:
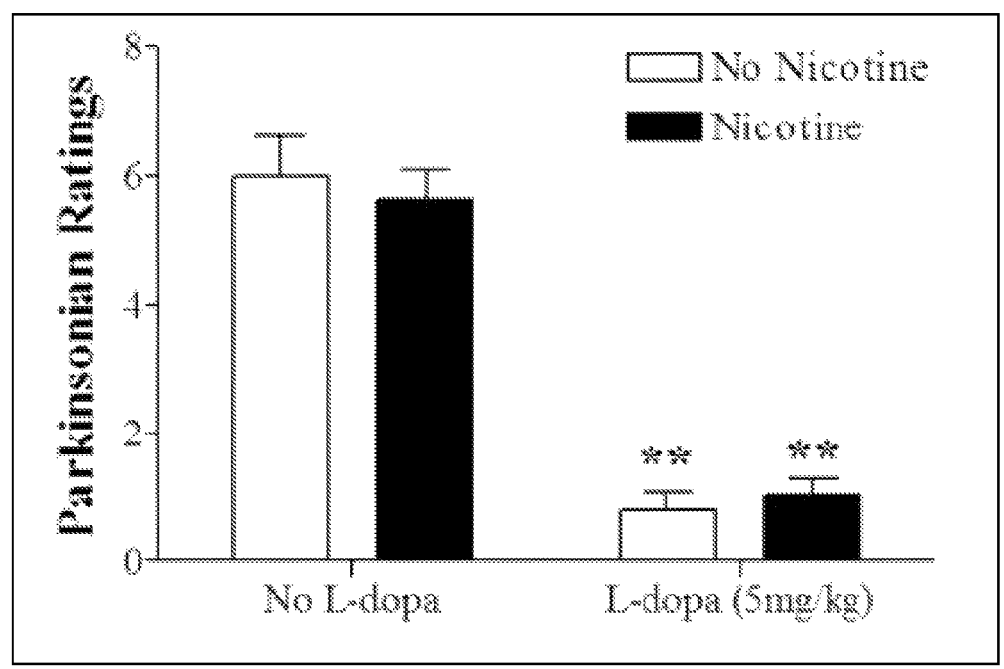
FIG. 7 depicts a graph showing that nicotine administration does not affect Parkinsonism on or off L-dopa treatment.

Nicotine administration does not affect parkinsonism on or off levodopa treatment: Levodopa administration reduced parkinsonism ratings, which were measured 1.5-2 hours after levodopa dosing when its effects are maximal (FIG. 7 and Table 2). Nicotine treatment did not affect parkinsonism either on of off levodopa treatment (F [1, 16]=0.03, p=0.8718).

TABLE 2

Nicotine administration does not affect parkinsonism on or off levodopa treatment

| levodopa Treatment | Nicotine Treatment | Parkinson Ratings | | |
|---|---|---|---|---|
| | | Expt 1 | Expt 2 (crossover) | Mean ± SE (n) |
| No | No | 3.7, 6.1, 6.0 | 6.8, 7.4 | 6.0 ± 0.6 (5) |
| No | Yes | 5.2, 6.6 | 4.1, 6.4, 5.9 | 5.6 ± 0.5 (5) |
| Yes | No | 0.4, 0.4, 0.6 | 1.8, 0.9 | 0.8 ± 0.3 (5) |
| Yes | Yes | 1.7, 1.5 | 0.8, 0.4, 0.8 | 1.0 ± 0.2 (5) |

FIG. 7 shows the effect of nicotine administration on parkinsonism. White bars indicate no nicotine treatment and black bars indicate nicotine treatment. Parkinsonism was evaluated immediately before the afternoon L-dopa dose and 1.5 to 2 hours after L-dopa treatment, when a maximal antiparkinsonian effect is anticipated. Two of the seven animals in the study were not parkinsonian, and therefore were not included in this analysis. Error bars are the means±standard error of five animals before and after crossover of nicotine treatment. **p<0.01, as compared with the same group with no L-dopa treatment by a Mann-Withney test. These results suggest that nicotine treatment influenced only dyskinetic behavior and not parkinsonism.

The results from example 1 and 2 are the first to show that nicotine treatment attenuates levodopa-induced dyskinesias in nonhuman primates. Nicotine treatment significantly reduced both the peak and duration of the dyskinetic response. Importantly, this was not accompanied by a worsening of parkinsonism either on or off levodopa. In animals pretreated with nicotine, that is, levodopa naïve monkeys, there was ~60% decline in levodopa-induced dyskinesias. In addition, nicotine treatment reduced dyskinesias by ~35% in monkeys that had received previously been treated with levodopa, that is, in levodopa-primed monkeys.

Example 3

Effect of Continuous Delivery of Nicotine on its Antidyskinetic Effect

Animals: Two groups of experimental animals (see Table 3) are required for these experiments to determine the effectiveness of minipump administration in reducing dyskinesias in lesioned monkeys

TABLE 3

Groups for experiments in example 3

| Groups | n | Nicotine | L-dopa treatment (5 mg/kg orally) |
|---|---|---|---|
| (1) MPTP-lesioned | 8 | No | Yes |
| (2) MPTP-lesioned | 8 | Yes | Yes |

MPTP treatment. All animals are lesioned with an injection of MPTP (1.5-2.0 mg/kg, sc). The animals are rated for parkinsonism 3-4 weeks after lesioning according to methods described in example 1. If an animal is not parkinsonian, MPTP injection will be repeated up to 4 times. The lesioning process may therefore require up to 4 months to generate animals with parkinsonism. Eight animals are required per group as our objective is to obtain stably parkinsonian animals. In general ~80% of the animals develop stable parkinsonism. The animals are then allowed to recover from the last MPTP injection for 1 month to ensure they are stably parkinsonian before the minipumps are surgically implanted.

Minipump delivery: Nicotine is delivered via a minipump according to standard procedure, using the 0.2 ml pump (ALZET) to release nicotine over a 4-week period. Nicotine is administered at a dose of 0.5 mg/kg/day (free base). This dose is chosen based on previous data in nonhuman primates known in the art. Surgically implanted minipumps containing nicotine and the treatment appears to be well tolerated, with no appreciable weight loss or adverse effects. The non-nicotine treated group will receive vehicle in the pump. Plasma nicotine and cotinine levels will be measured 1-2 weeks after minipump implantation to ensure adequate nicotine dosing as described in example 1. The objective is to achieve levels similar to those in our current study involving nicotine administration in the drinking water (~500 ng/ml). The pumps are replaced monthly to ensure that the supply of nicotine remains constant. The animals receive nicotine for 2 months prior to the initiation of L-dopa treatment.

L-Dopa: After 2 months of nicotine infusion, both groups of monkeys (either vehicle or nicotine) are gavaged with L-dopa/carbidopa (5 mg/kg/1.25 mg/kg) twice daily at 9:00 AM and 1:00 PM. Treatment is performed on a 5-day-on 2-day-off schedule and is done for at least 4 weeks. If nicotine treatment reduces dyskinesias, L-dopa treatment is continued (up to 2 months) to allow us to determine how long the decrease in dyskinesias is maintained.

Parkinsonism will be rated using a modified nonhuman primate parkinsonian rating scale as described in example 1. Dyskinesias are monitored from videotapes, using the rating system detailed in example 1. Parkinsonian ratings are done throughout the entire treatment period (~9 months) 3 times weekly. Dyskinesia ratings are done when the animals are being treated with L-dopa.

These studies will test the effect of constant nicotine administration which may enhance the antidyskinetic effect of nicotine. Without being limited to any theory, continuous nicotine application results in an initial receptor activation that is followed by receptor desensitization or inactivation that remains until the nicotine dissipates. Receptor desensitization or blockade is then thought to result in compensatory changes in striatal nAChRs, with the receptor changes possibly being more pronounced depending on the period of desensitization. Thus, one might expect a more sustained-desensitization and receptor changes with continuous nicotine treatment.

Example 4

Nicotine Treatment Reduces L-Dopa-Induced Dyskinetic-Like Movements in Rats

Materials and Methods

Animal model—6-Hydroxydopamine lesioning. We used the 6-hydroxydopamine lesioned rat model of nigrostriatal damage described by Cenci and colleagues (Cenci et al., 1998 Eur J Neurosci 10:2694-2706; Cenci et al., 2002 Nat Rev Neurosci 3:574-579). Adult male Sprague-Dawley rats were anesthetized with isofluorane, and then placed in a Kopf stereotaxic instrument. Burr holes were drilled through the skull and an intracranial injection of 6 µg 6-hydroxydopamine (2 µg/µl) stereotaxically injected at two separate sites into the right ascending dopamine fiber bundle, for a total of 12 µg 6-hydroxydopamine. The coordinates for the position of these two lesion sites were as follows relative to the Bregma and dural surface: (1) anteroposterior, −4.4; lateral, 1.2; ventral, 7.8; tooth bar at −2.4; (2) anteroposterior, −4.0; lateral, 0.75; ventral, 8.0; tooth bar at +3.4 (Cenci et al., 1998 Eur J Neurosci 10:2694-2706; Cenci et al., 2002 Nat Rev Neurosci 3:574-579). All procedures conformed to the NIH Guide for the Care and Use of Laboratory Animals and were approved by the Institutional Animal Care and Use Committee.

Behavioral assessment of the lesion. As an index of nigrostriatal damage, the rats were tested for rotational behavior 3 and 4 weeks after lesioning. This was done using an automated behavioral measurement apparatus that has four cylindrical chambers (50 cm height×34 cm diameter) (ROTOMAX, AccuScan Instruments Inc. Columbus, Ohio, USA). A rat was placed in one of the chambers for 30 min for acclimatization, after which time amphetamine (4 mg/kg ip) was administered as previously described (Visanji et al., 2006, Neuropharmacology 51:506-516). The rats were observed for circling behavior for 90 min after injection. The rats were tested a second time one week later and the data from the two testing periods pooled.

Figure 8:
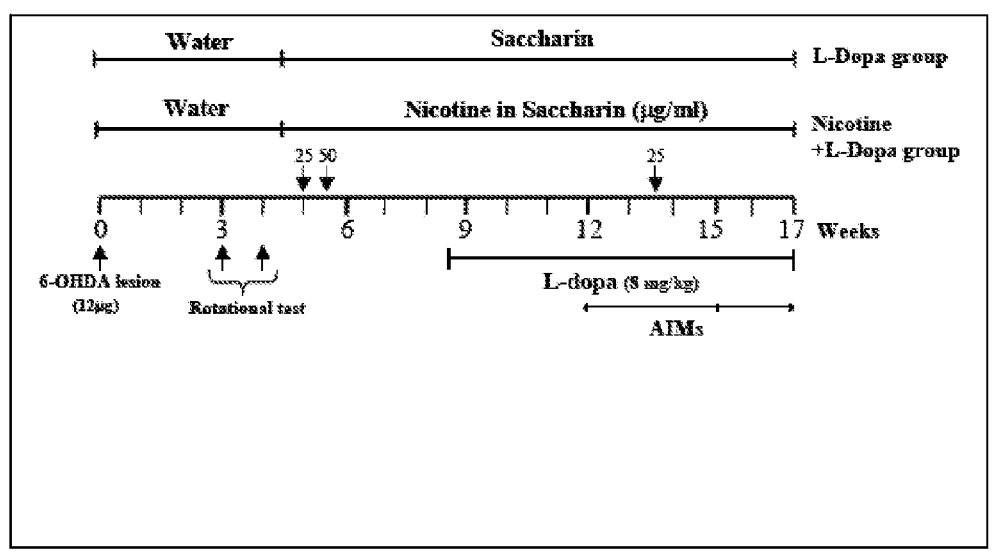
FIG. 8 depicts schedule for treatment paradigms and behavioral testing in rats.

Nicotine treatment regimen. The rats were first given a drinking solution containing 1% saccharin for 3-4 days (FIG. 8). Nicotine was then added at a concentration of 25 µg/ml, and increased to 50 µg/ml 3-4 days later. Animals were maintained on this dose for 3 weeks. L-dopa treatment was then initiated, as below, with the nicotine dosing continued.

L-dopa treatment and behavioral testing for AIMs. Rats received single daily intraperitoneal injections of 8 mg/kg L-dopa methyl ester plus 15 mg/kg benserazide for 3 weeks (FIG. 8), as described (Cenci et al., 1998 Eur J Neurosci 10:2694-2706; Cenci et al., 2002 Nat Rev Neurosci 3:574-579). Abnormal involuntary movements (AIMs) after daily LDOPA injection were then quantified using the scale developed by Cenci and colleagues (Cenci et al., 1998 Eur J Neurosci 10:2694-2706; Cenci et al., 2002 Nat Rev Neurosci 3:574-579), as previously done in our laboratory (Cox et al., 2007, Exp. Neurol.). Rats were placed in a Rotomax test chamber. They were then scored on a scale from 0 to 4: 1=occasional; 2=frequent; 3=continuous but interrupted by sensory distraction; 4=continuous, severe, not interrupted by sensory distraction. The rating categories were as follows; (1) axial dystonia, consisting of twisting posturing of the head and neck; (2) orolingual dyskinesia, with stereotyped jaw movements and contralateral tongue protrusion and (3) forelimb movements, with dystonic movements of the contralateral forelimb. They were also assessed for locomotive dyskinesia, or increased locomotion with contralateral side bias; however, these scores were not included because the interpretation of this motor response is not clear (Papa et al., 1994 Brain Res 662; 69-74; Cenci et al., 1998 Eur J Neurosci 10:2694-2706).

Locomotive dyskinesias are distinct from turning behavior described above. Rats were observed individually every 20 min for 3 h following L-dopa treatment. The maximum possible score in each session was thus 108 (maximum score per observation=12; number of observations per session=9). Rats were evaluated by two raters, one blinded to treatment.

Data analyses. Statistical significance was determined using Student's t-tests or ANOVA followed by Bonferroni post hoc tests, as appropriate. Data are mean±SEM. A p level of 0.05 was considered significant.

Results

Figure 9:
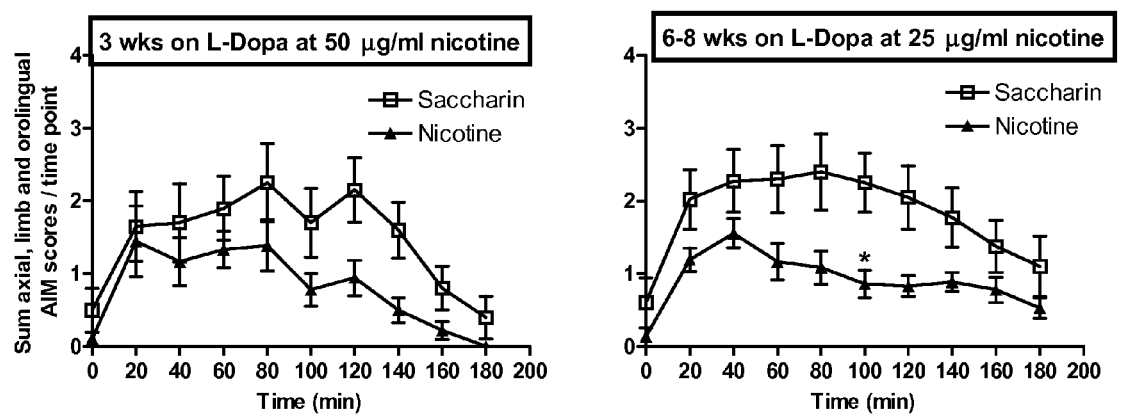
FIG. 9 depicts graphs showing time courses of nicotine treatment on total L-dopa-induced AIMs in 6-hydroxy-dopamine-lesioned rats.

Nicotine treatment reduces total AIM scores. The time course of the effect of 50 µg/ml nicotine on the total number of AIMs after 3 weeks of L-dopa treatment is shown in FIG. 9 (left panel). Each value in FIG. 9 represents the mean±SEM of 9-10 rats. *p<0.05 using a Bonferroni post hoc test. A reduction in AIMs scores was observed throughout the entire 3-hour period, with a significant main effect of nicotine treatment (F(1, 153)=15.83, p=0.0001) and time (F(8, 153)=4.12, p=0.0002), with no significant interaction (F(8, 153)=0.388, p=0.93). Experiments were next done to determine whether a lower dose of nicotine also decreased AIMs. The nicotine concentration in the drinking water was therefore reduced from 50 to 25 µg/ml with continued L-dopa administration (see FIG. 8). The rats were tested for AIMs two and four weeks after initiation of the lower dose of nicotine (25 µg/ml). Since results at two and four weeks were similar, the data were pooled. FIG. 9 (right panel) shows that the nicotine-induced reduction in AIMs was sustained using 25 µg/ml nicotine in the drinking water. Two-way ANOVA demonstrated a significant main effect of nicotine treatment (F (1, 153)=35.32, p<0.0001) and time (F (8, 153)=2.06, p=0.0428), with no significant interaction (F (8, 153)=0.41, p=0.92).

Figure 10:
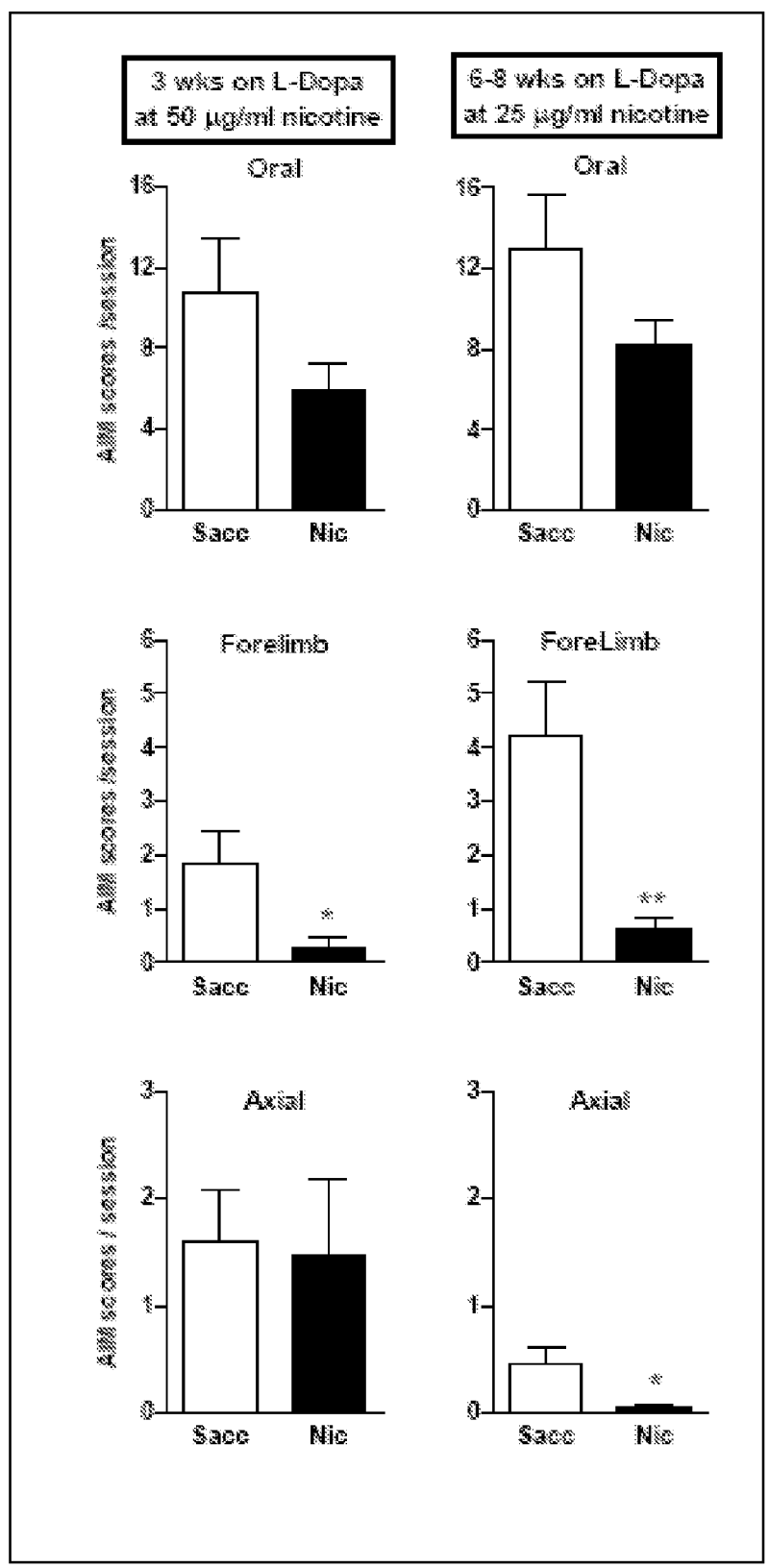
FIG. 10 depicts graphs showing that nicotine treatment differentially reduces L-dopa-induced AIM components.

Nicotine treatment reduces different AIM components. As indicated earlier, AIMs consist of several different components including (1) axial dystonia; (2) orolingual dyskinesia; and (3) limb dyskinesia. Results shown are for the 3 and 6-8 week time points (FIG. 10). Each value of FIG. 10 represents the mean±SEM of 9-10 rats, *p<0.05 and **p<0.01 using a t-test. There were significant decreases in forelimb dyskinesias at both time points with both doses of nicotine, and in axial dyskinesias at the 6-8 week time point. There was a trend for a decrease in oral dyskinesias, although this was not significant. Thus, nicotine treatment reduces some AIMs, but not others. These results may imply that nicotine differentially affects molecular mechanisms linked to AIMs. To evaluate this possibility, correlation analyses can be done between nicotine-mediated reduction in AIMs components and molecular mechanisms.

Effect of nicotine on behavior related to parkinsonism. Our studies in monkeys showed that nicotine treatment reduced L-dopa-induced dyskinesias without affecting parkinsonism. In our preliminary studies in rats, we found that nicotine treatment did not affect turning behavior, which is used as an index of nigrostriatal damage (Mabandla et al., 2004 Metab Brain Dis 19; 43-50; Howells et al., 2005 Behav Brain Res 165:210-220; Steiner et al., 2006 Exp Neurol 199:291-300). The extent of turning was quantified using the ROTOMAX, AccuScan System, with no difference between rats receiving saccharin (8.2+3.7, n=10) compared to nicotine (8.4+6.7, n=9). The effect on nicotine on rotarod performance can also be tested. This is another approach used to evaluate effects of drugs on motor performance in parkinsonian rats (Lundblad et al., 2003 J Neurochem 84:1398-1410; Dekundy et al., 2007 Behav Brain Res 179:76-89).

The present data show that nicotine treatment significantly reduces L-dopa-induced AIMs in a 6-hydroxydopamine-lesioned rat model. They demonstrate a decline in AIMs at nicotine doses of 25 and 50 µg/ml in the drinking water. This effect of nicotine persists with at least 2 months of L-dopa treatment. These results are important as they further support the idea that nicotine may be useful for the treatment of L-dopa-induced dyskinesias in Parkinson's disease.

Example 5

Effects of Nicotinic Receptor Agonist on L-Dopa-Induced Dyskinetic Movements

The effect of nicotinic receptor agonist such as conotoxin-MII, epibatidine, A-85380, cytisine, lobeline, anabasine, SIB-1508Y, SIB-1553A, ABT-418, ABT-594, ABT-894, TC-2403, TC-2559, RJR-2403, SSR180711, GTS-21 and varenicline can be tested using the models described in the previous examples. The effect of nicotinic receptor agonist in L-dopa-induced dyskinesias can be tested in the rodent model described in Example 4. The compounds can in addition be tested in a nonhuman primate model, which exhibits parkinsonian symptoms and dyskinesias that closely resemble those in Parkinson's disease such as the model described in Examples 1-3. Nicotinic receptor agonist can be tested using both models. Alternatively, nicotinic receptor agonist can be tested using either one of the models described herein as well as any model known in the art.

Rodent Model

6-Hydroxydopamine lesion. Rats (30) can be first be lesioned with 6-hydroxydopamine as described in Example 4.

Behavioral assessment of the lesion. As an index of nigrostriatal damage, the rats will be tested for rotational behavior two (2) weeks after the lesion. This will be done using an automated behavioral measurement apparatus. Baseline activity will be monitored for thirty (30) minutes, after which time amphetamine (4 mg/kg i.p.) will be administered. Because amphetamine induces a greater dopamine release from the unlesioned as compared to the lesioned striatum, the animals turn to the ipsilateral side. Rotation will be monitored for ninety (90) minutes. The rats will be retested one (1) week later, and the results from the two (2) testing periods pooled. Rats with scores over 100 rotations will be retained for further study (generally 20-25 animals out of 30).

L-dopa treatment. Rats (20) can be injected i.p. with 8-12 mg/kg L-dopa methyl ester plus 15 mg/kg benserazide once daily for three (3) weeks and longer (Cenci et al., 1998 Eur J Neurosci 10:2694-2706.; Cenci et al., 2002 Nat Rev Neurosci 3:574-579). Three (3) weeks of L-dopa treatment results in the development of AIMs in the majority of rats. L-dopa dosing will be started after the nicotinic agonist treatment.

Evaluation of L-dopa-induced AIMs. L-dopa-induced AIMs can be quantified as described in Example 4 (Cenci et al., 1998 Eur J Neurosci 10:2694-2706.; Cenci et al., 2002 Nat Rev Neurosci 3:574-579; Cox et al., 2007 Exp Neurol). This includes axial dystonia, orolingual dyskinesia and forelimb movements with rats scored on a scale from 0 to 4 for each AIM component. Rats will be observed individually every twenty (20) minutes for three (3) hours following L-dopa treatment. The maximum possible score in each session is thus 108 (maximum score per observation=12; number of observations per session=9). Two raters, one blinded to treatment, will evaluate the rats.

Nicotinic agonist regimen. The agonists can be administered 2-3 weeks prior to L-dopa treatment, preferably in the drinking water. The optimal dose and route of agonist administration will need to be determined prior to initiation of the experiments with lesioned animals. If this information is not available, pilot studies can be done to determine optimal dosing.

Evaluation of parkinsonism. Amphetamine and L-dopa-induced contralateral turning will be evaluated as described above to determine the effects on parkinsonism.

Treatment. All thirty (30) rats can be first lesioned with 6-hydroxydopamine over a one (1) week period. They can be tested 2 and 3 weeks later to determine the extent of nigrostriatal damage by evaluating ipsilateral turning in response to amphetamine (20-25 rats acceptable rotation). One (1) week is usually required to evaluate turning behavior in the animals; behavioral testing of 20-25 rats usually takes two (2) weeks. At week 4, Group 1 will be given vehicle (e.g. saccharin) only. Group 2 will be given vehicle (possibly saccharin) plus agonist. L-dopa plus benserazide will then be administered two (2) weeks after agonist is started. AIMs are determined three (3) weeks after the start of L-dopa administration. L-dopa treatment will be continued throughout.

Non Human Primate Model

Although rats are an excellent model for screening compounds, nonhuman primate studies ensure efficacy in a model that more closely resembles human Parkinson's disease. The experiments can be designed to further refine the understanding of the dosing and mode of the nicotinic receptor agonist administration that will be most effective. The non human primate model described in Examples 1 and 2 can be used to test the effect of nicotinic receptor agonist in L-dopa induced dyskinesias.

The effect of continuous delivery of the nicotinic receptor agonist on L-dopa induced dyskinesias can be tested via minipump as described in Example 3.

Example 6

Intermittent and Continuous Nicotine Treatment Reduce L-Dopa-Induced Dyskinesias in a Rat Model of Parkinson's Disease Methods Animals. Experiments were performed using male Sprague-Dawley rats (initial weight 250 g) purchased from Charles River Laboratories (Gilroy, Calif.). They were housed 2 per cage under a 12-12 h light-dark cycle in a temperature-controlled room with free access to food and water. Three to four days after arrival, the rats were unilaterally lesioned with 6-hydroxydopamine as previously described (Cenci et al., 1998 Eur J Neurosci 10:2694-2706.; Cenci et al., 2002 Nat Rev Neurosci 3:574-579). During the lesioning procedure the rats were maintained under isofluorane anesthesia (2%). They were placed in a Kopf stereotaxic instrument and burr holes drilled through the skull at the following coordinates relative to the Bregma and dural surface: (1) anteroposterior, −4.4; lateral, 1.2; ventral, 7.8; tooth bar at −2.4; (2) anteroposterior, −4.0; lateral, 0.75; ventral, 8.0; tooth bar at +3.4 (Cenci et al., 1998 Eur J Neurosci 10:2694-2706.; Cenci et al., 2002 Nat Rev Neurosci 3:574-579). 6-Hydroxydopamine was dissolved in 0.02% ascorbic acid/saline at a concentration of 3 ug/ul. Two µl was stereotaxically injected at each of these sites for a total of 12 mg into the right ascending dopamine fiber bundle. Infusion of 6-hydroxydopamine into the target area was over a 2-min period, with the cannula maintained at the site of injection for a further 2 min. All procedures conformed to the NIH Guide for the Care and Use of Laboratory Animals and were approved by the Institutional Animal Care and Use Committee.

Behavioral testing. Two and three weeks after lesioning, rats were tested for rotational behavior in an automated behavioral measurement apparatus (ROTOMAX, AccuScan Instruments Inc. Columbus, Ohio, USA). Each rat was placed in a cylindrical glass chamber for 30 min for acclimatization, after which amphetamine (4.0 mg/kg ip) was administered. The behavior was monitored for an additional 90 min, with rats making at least 100 ipsilateral turns used for further study.

Figure 11:
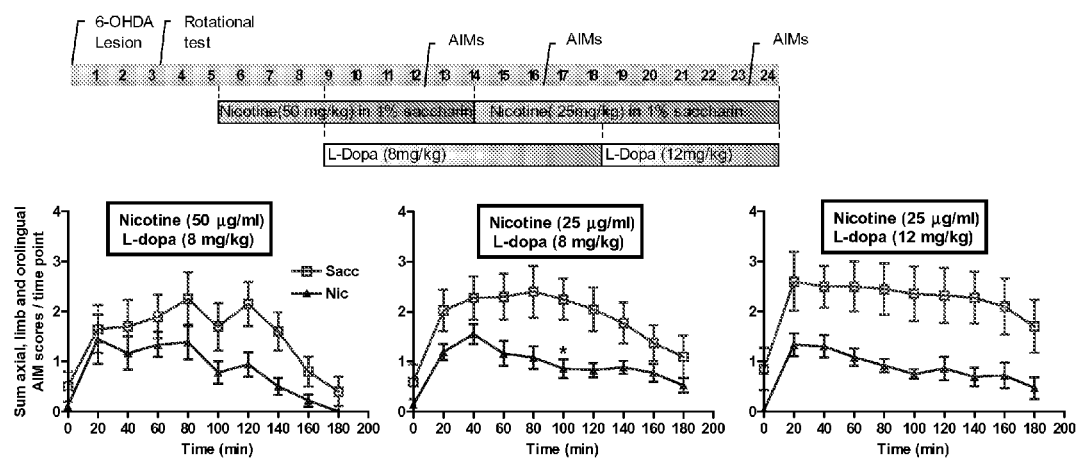
FIG. 11 depicts graphs showing that intermittent nicotine treatment reduces L-dopa-induced abnormal involuntary movements (AIMs) in rats.

Nicotine treatment. When the behavioral testing was completed, rats were treated with nicotine via the drinking water that yields an intermittent dosing regimen or via minipump that provides a constant level of nicotine. For administration via the drinking water, rats were first provided with a solution containing 1% saccharin (Sigma Chemical Co., St. Louis, Mo.) to mask the bitter taste of nicotine. After 2-3 days of acclimation, nicotine (free base, Sigma Chemical Co., St. Louis, Mo.) was added to the saccharin-containing drinking solution of the treated group (pH 7.0). Nicotine was initially given at a concentration of 25 µg/ml nicotine for 2 days. This was subsequently increased to 50 µg/ml nicotine, and animals maintained at this dose for several weeks (FIG. 11). Measurement of fluid intake showed that animals with nicotine in the solution drank less than their vehicle-treated counterparts, in agreement with previous studies in mice. The rats appeared healthy although there was a small difference in body weight with continued dosing.

In a separate series of experiments, rats were given nicotine continuously via Alzet minipumps (model 2004-200 µl), which secrete nicotine for 28 days. These were subcutaneously implanted according to the manufacturer's instruction. Pumps were filled with either sterilized water or nicotine base in water to deliver 2 mg/kg/d. Body weight was similar in the rats receiving minipumps containing either vehicle or nicotine (Table 4).

TABLE 4

Plasma cotinine levels in rats receiving chronic nicotine

| Regimen | Treatment | Nicotine | Number of rats | [Cotinine] ng/ml |
|---|---|---|---|---|
| Drinking water | Saccharin | 0 | 10 | 0 ± 0 |
|  | Nicotine | 50 µg/ml | 9 | 987 ± 81 |
|  | Nicotine | 25 µg/ml | 9 | 303 ± 23 |
| Minipump | Water | 0 | 12 | 0 ± 0 |
|  | Nicotine | 2 mg/kg/day | 12 | 336 ± 49 |

Values represent the mean ± SEM of the indicated number of animals.

L-dopa treatment. Three weeks after initiation of the 50 ug/ml nicotine dose, the rats received single daily intraperitoneal injections of 8 mg/kg L-dopa methyl ester plus 15 mg/kg benserazide (both from Sigma Chemical Co., St. Louis, Mo.) (Cenci et al., 1998 Eur J Neurosci 10:2694-2706.; Cenci et al., 2002 Nat Rev Neurosci 3:574-579). After 3 weeks of daily L-dopa dosing, abnormal involuntary movements (AIMs) were quantified. These included (1) axial dystonia, contralateral twisted posturing of the neck and upper body; (2) orolingual dyskinesia, stereotyped jaw movements and contralateral tongue protrusion; and (3) forelimb dyskinesia, repetitive rhythmic jerks or dystonic posturing of the contralateral forelimb and/or grabbing movements of the contralateral paw (Cenci et al., 1998 Eur J Neurosci 10:2694-2706.; Cenci et al., 2002 Nat Rev Neurosci 3:574-579; Carta et al., 2006 Neurochem 96:1718-1727). Rats were scored on a scale from 0 to 4 for each of these three AIMs as follows: 1=occasional; 2=frequent; 3=continuous but interrupted by sensory distraction; and 4=continuous, severe, not interrupted by sensory distraction. Animal behavior was evaluated over 20 min sessions by two raters, one blinded to treatment, for 3 h following injections. This yielded a total of 9 sessions of testing per animals. The maximum possible score for each animal was thus 108 (maximum score per session=9; number of sessions over 3 h=12).

Plasma cotinine measurement. The nicotine metabolite cotinine was determined as an indirect measure of plasma nicotine levels using an ELISA kit (Orasure Technologies, Bethlehem, Pa.). Blood samples were collected from the femoral vein after 1 to 2 wk after initiation of nicotine treatment via the drinking water or minipump. Plasma was prepared and a <1 µl aliquot used for assay according to the manufacturer's instructions. A standard curve ranging from 5 to 100 ng/ml cotinine was done with every assay.

Data analyses. All analyses were done using GraphPad Prism® (GraphPad Software, Inc, San Diego, Calif.). Differences in rating scores between groups were analyzed using nonparametric tests (Mann-Whitney-Mann test or Wilcoxon test for paired data). For the time course studies, analysis of variance (ANOVA) followed by Bonferroni multiple comparison test was used. A level of 0.05 was considered significant. Results are expressed as mean±SEM.

Results

FIG. 11 shows that intermittent nicotine treatment reduces L-dopa-induced abnormal involuntary movements (AIMs). Treatment schedule (top panel) depicting the time of administration of nicotine (in drinking water), L-dopa dosing and behavioral testing. Rats were provided with vehicle drinking water containing 1% saccharin for 1 week. Some of the rats (n=10) were continued on this solution, while nicotine was added to the vehicle drinking water of the remaining animals (n=9). Nicotine administration was initiated at a dose of 25 µg/ml, and then switched to a final maintenance dose of 50 µg/ml. Three weeks later, they were given L-dopa (8 mg/kg ip) once daily for 10 weeks, and then 12 mg/kg L-dopa for a further 5 weeks. AIMs were rated throughout the L-dopa treatment by two raters, one blinded to treatment. AIMs were rated as described in methods over a 3-hour period, including 30-min of baseline (no L-dopa). There was a significant effect (P<0.001) of nicotine treatment on L-dopa-induced AIMS using ANOVA. Each symbol is the mean±SEM of 9-10 rats.

Figure 12:
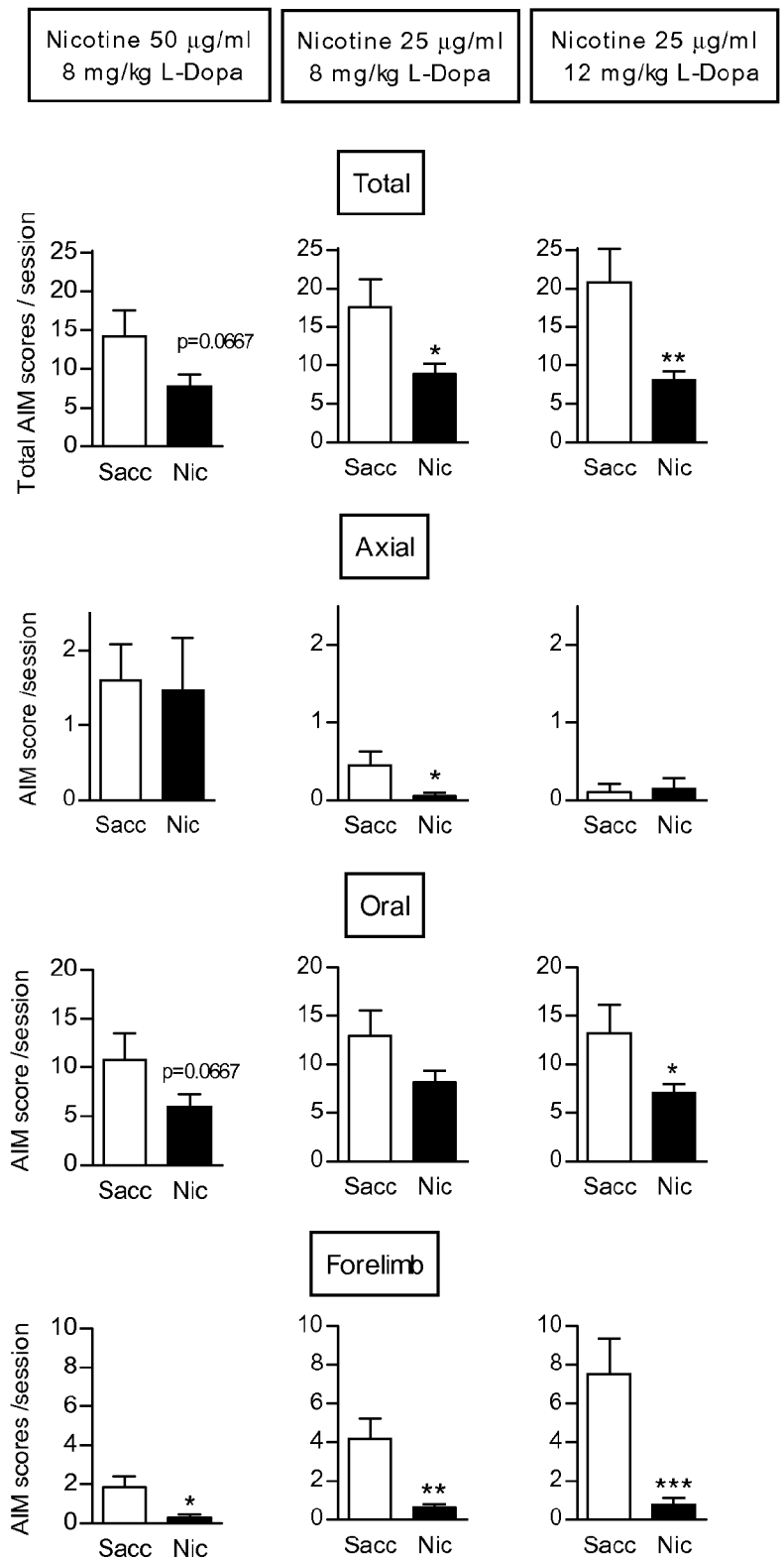
FIG. 12 depicts graphs showing that intermittent nicotine treatment reduced individual AIM components in rats after L-dopa treatment.

FIG. 12 shows that intermittent nicotine treatment reduced individual AIM components after L-dopa treatment. Rats were given nicotine in the drinking solution and subsequently administered L-dopa. The rats were evaluated for total, axial, oral and forelimb AIMs by two raters, one blinded to treatment status of the animals. Each value represents the mean+SEM of 9-10 rats. *P<0.05, P<0.01 and *P<0.001 compared to rats receiving only saccharin using a Mann-Whitney test.

Figure 13:
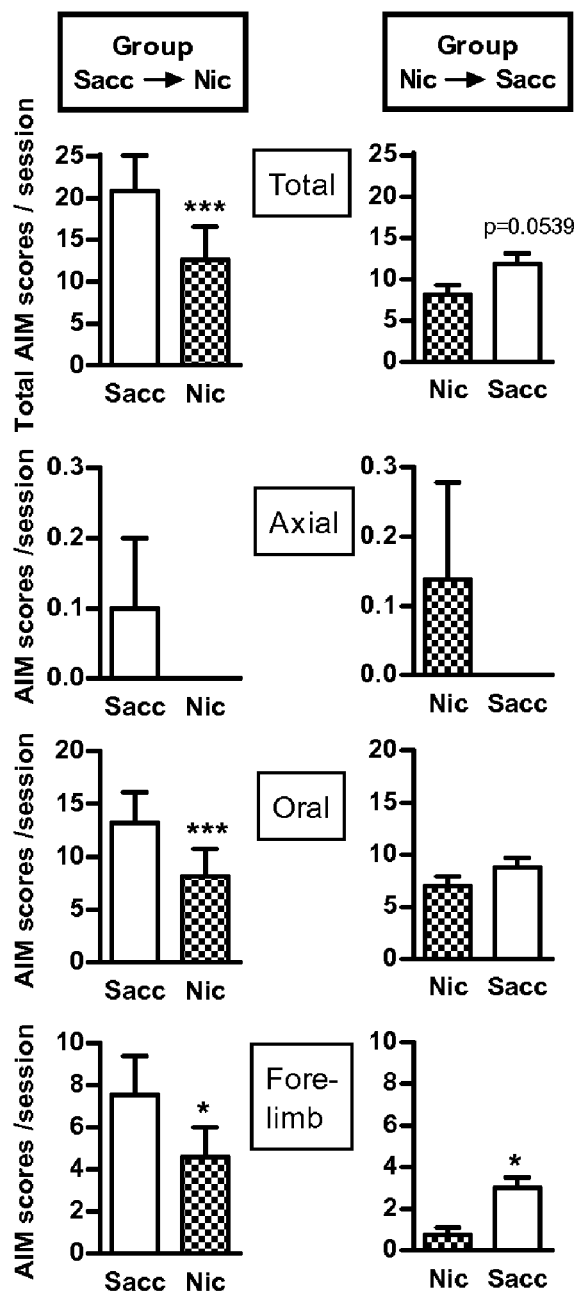
FIG. 13 shows a crossover study depicting the effect of intermittent nicotine treatment via the drinking water on L-dopa-induced AIMs in rats.

FIG. 13 shows a crossover study depicting the effect of intermittent nicotine treatment via the drinking water on L-dopa-induced AIMs. The left-hand panels depict results from rats that had initially received no nicotine prior to the first L-dopa treatment period, and were subsequently given nicotine in the drinking solution as outlined in FIG. 11. The right-hand panels depict results from rats that had initially received nicotine prior to the first L-dopa treatment period, and were subsequently given saccharin in the drinking solution. Nicotine administration reduced L-dopa-induced AIMS, while its removal resulted in an increase in AIMs development. Each value represents the mean+SEM of 9-10 rats. *P<0.05 and ***P<0.001 compared to the initial treatment using a Wilcoxon test.

Figure 14:
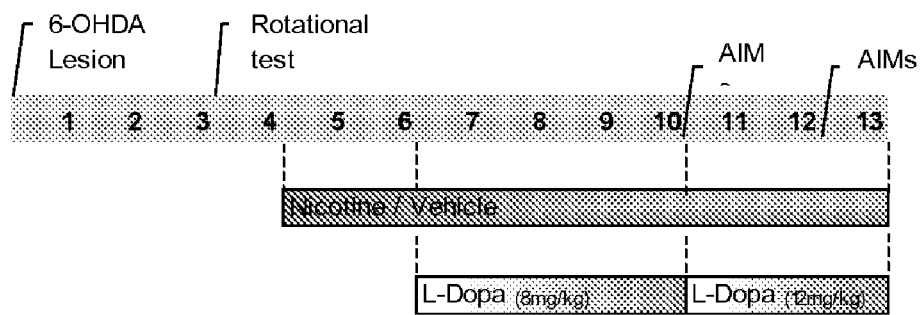
FIG. 14 shows that continuous nicotine exposure via minipump reduces L-dopa-induced AIMs.
Figure 14:
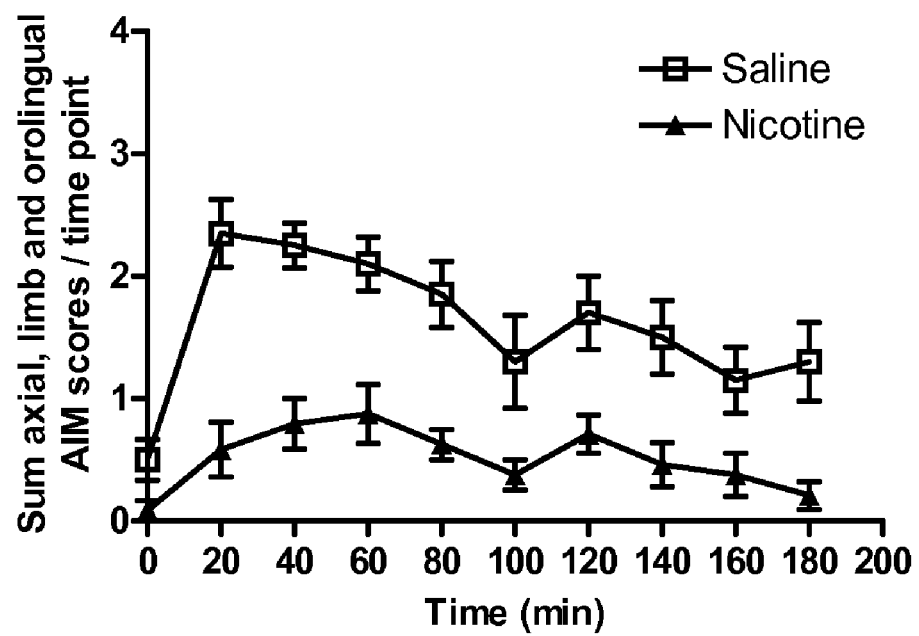

FIG. 14 shows continuous nicotine exposure via minipump reduces L-dopa-induced AIMs. Treatment schedule (top) depicting the time of administration of nicotine (via minipump), L-dopa dosing and behavioral testing. Half of the rats were implanted with minipumps containing nicotine (2 mg/kg/d) 4 weeks after 6-OHDA lesioning, and the other half with minipumps containing vehicle. Two weeks later, all the rats were given L-dopa (8 mg/kg ip) once daily for 4 weeks, and then 12 mg/kg L-dopa for a further 3 weeks. AIMs were rated throughout the L-dopa treatment by two raters, one blinded to treatment. The time course of the effect of nicotine on AIMs after L-dopa administration is depicted in the graph. AIMs were rated as described in methods over a 3-hour period, including 30-min of baseline (no L-dopa). There was a significant effect (P<0.001) of nicotine treatment on L-dopa-induced AIMs using ANOVA. Each symbol is the mean±SEM of 12 rats.

Figure 15:
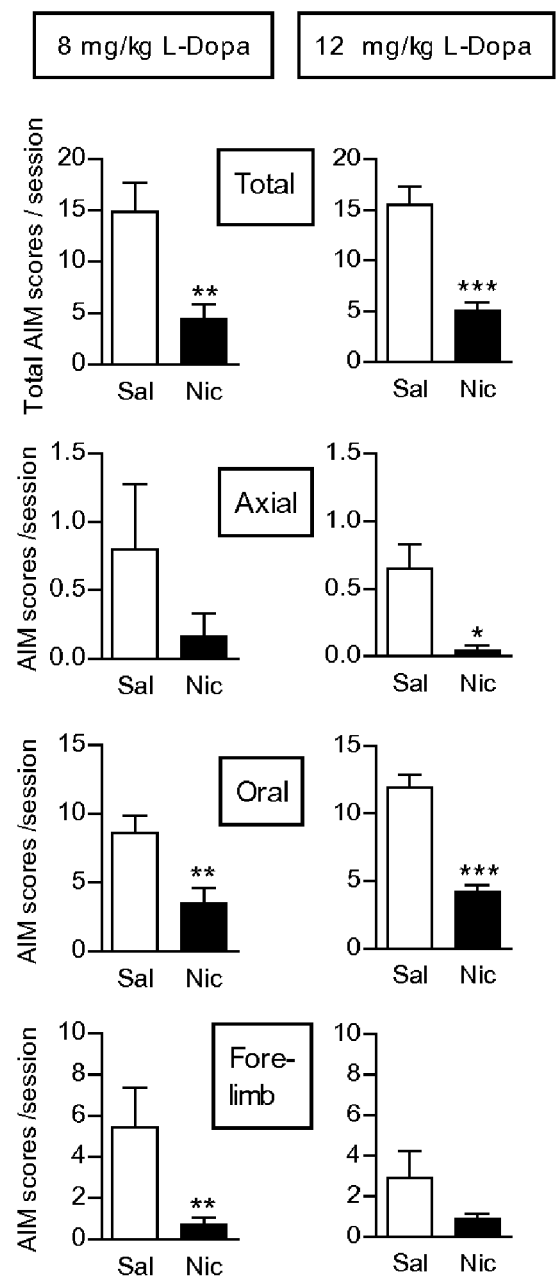
FIG. 15 shows that constant nicotine exposure via minipump reduced individual AIM components after L-dopa treatment.

FIG. 15 shows that constant nicotine exposure via minipump reduced individual AIM components after L-dopa treatment. Rats were given nicotine (2 mg/kg/d) via minipump and subsequently administered L-dopa. The rats were evaluated for total, axial, oral and forelimb AIMs by two raters, one blinded to treatment status of the animals. Each value represents the mean+SEM of 12 rats. *P<0.05, P<0.01 and *P<0.001 compared to rats receiving no nicotine using a Mann-Whitney test.

Figure 16:
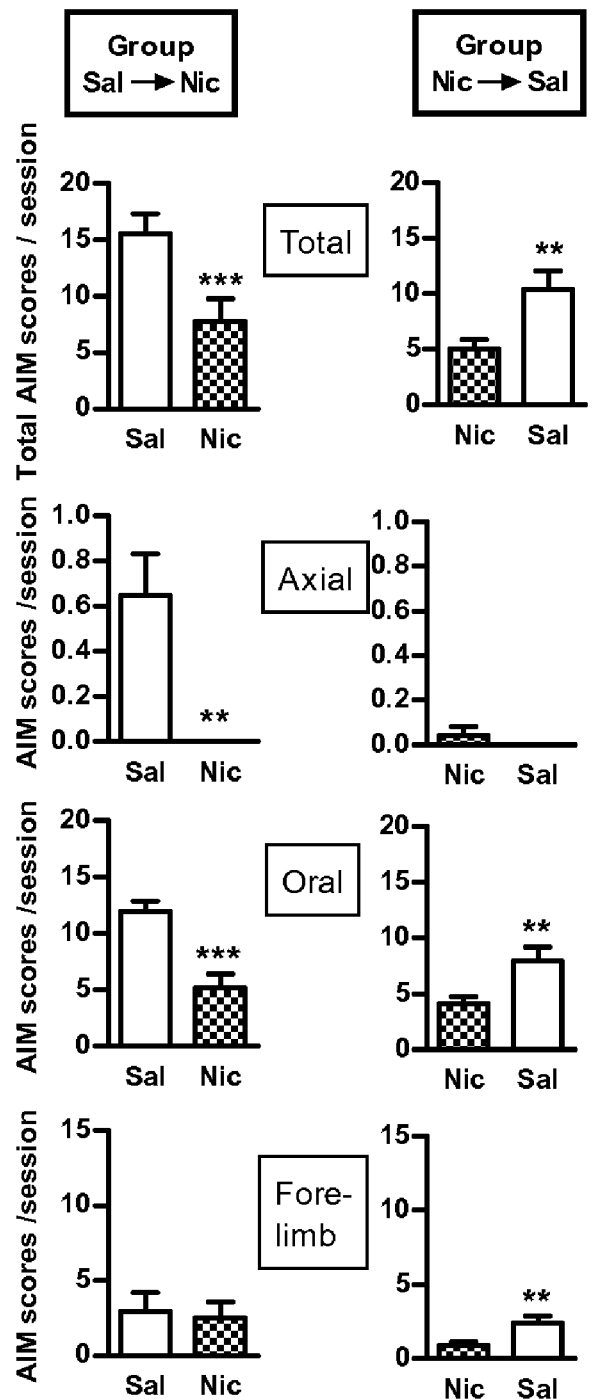
FIG. 16 shows a crossover study depicting the effect of constant nicotine exposure via minipump on L-dopa-induced AIMs.

FIG. 16 shows a crossover study depicting the effect of constant nicotine exposure via minipump on L-dopa-induced AIMs. The left-hand panels depict results from rats that had initially received no nicotine prior to the first L-dopa treatment period, and were subsequently given nicotine via minipump as depicted in FIG. 14. The right-hand panels depict results from rats that had initially received nicotine prior to the first L-dopa treatment period, and were subsequently given minipumps containing no nicotine. Nicotine administration reduced L-dopa-induced AIMs, while its removal resulted in an increase in AIMs development. Each value represents the mean+SEM of 12 rats. P<0.01 and *P<0.001 compared to the initial treatment using a Wilcoxon test.

Example 7

Effects of Nicotinic Receptor Agonist on L-Dopa-Induced Dyskinetic Movements in Humans An empiric trial on the effects of nicotine on levodopa-induced dyskinesias can be conducted. Inclusion criteria include patients, both male and female, who suffered from Parkinson's disease that are 30 years old and older. The main inclusion criteria are: (i) Levodopa associated peak-dose dyskinesia which is at least moderately disabling and present for ≧25% of the waking day (UPDRS part IV, items 32 and 33, each ≧2) (ii) Levodopa associated end of dose deterioration, with an average 'Off' time of 2.5 hours or more per day based on the pre-study patient diary recordings between Days −4 to 2 9 (iii) Stable Parkinson's medication for at least 1 month prior to randomization, with a minimum of 3 hours between the levodopa intakes (iv) Hoehn and Yahr Stages 1 to 4 during 'Off' period (v) Demonstrated ability to comprehend and give informed consent (vi) Ability to complete patient diary. The main exclusion criteria include: (i) Other clinically significant conditions apart from those typically associated with Parkinson's disease (ii) Intake of medication associated with exacerbation of dyskinesia or with extrapyramidal side effects and tardive dyskinesia or induction of liver enzymes; neuroleptics; drugs used in treatment of cognitive impairment; or specified drugs known to be substantially metabolized through the following cytochrome P450 isoenzymes: 1A2, 2B6, 2C19, 2C9, 2D6, and 2E1 (iii) Use of St. John's Wort or *Ginkgo Biloba* within 48 hrs prior to randomization and until the last treatment day with the study medication (iv) Intake of an investigational drug within 30 days prior to Initial Screening This study can be a multi-center, double-blind, placebo-controlled, multiple dose escalating, safety, tolerance, pharmacokinetics, and efficacy study of nicotine administered in Parkinson's disease patients who are concomitantly being treated with a combination product of levodopa and possible other antiparkinson medication. The patients will be randomized into one of five treatment groups to receive either fixed or ascending doses of Nicotine (from 0.3 to 4 mg per dose) or placebo. For efficacy assessments, the patient is assessed with levodopa challenge, following an overnight withdrawal of Parkinson's medication. Levodopa-induced dyskinesia is assessed using a standardized rating scale. Time spent in 'Off' state or in 'On' state without dyskinesia, with non-troublesome dyskinesia or with troublesome dyskinesia, is assessed using patient diaries (e.g. electronic patient diaries). Impact of dyskinesia on daily activities is quantified using a PDYS-26 questionnaire. To explore potential positive or negative impact of nicotine on cognitive functions, the study includes two cognitive tests. Finally, the study includes investigator assessments of CGI-I scales for dyskinesia, Parkinson's disease, and clinical condition in general.

Nicotine is compounded into capsules or tables and supplied to all subjects. The patients will be treated as described in Table below Subjects are instructed that concomitant medications should not be altered without speaking with the investigator. Subjects are advised that they will be contacted every day or every other day to assess progress in the trial and any side effects associated with the addition of nicotine. At the end of the trial, patients are interviewed. They are asked to rate their satisfaction with the study medication (−2-+2) and its ability to modulate the levodopa-induced dyskinesias. If the study has used placebo and is blinded, the blind is broken and statistical comparisons of nicotine versus placebo are performed.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method for reducing dopaminergic agent-induced dyskinesia comprising orally administering to a human being treated with said dopaminergic agent an amount of nicotine sufficient to reduce dyskinesia induced by said dopaminergic agent, wherein said amount of nicotine administered in a 24-hour period is about 24 milligrams or less and said amount is maintained for a period of more than two months.

2. A method for reducing dopaminergic agent-induced dyskinesia comprising orally administering to a human being treated with said dopaminergic agent an amount of nicotine sufficient to reduce dyskinesia induced by said dopaminergic agent, wherein said amount of nicotine administered in a 24-hour period is about 24 milligrams or less and said amount is maintained for the duration of treatment with said dopaminergic agent.

TABLE 5

Treatment Groups

| Group | Assigned Intervention |
|---|---|
| 1. Placebo<br>One placebo tablet administered from Day 1 to 35 | Drug: Nicotine<br>Nicotine in oral formulation every time levodopa is administered to the subjects (~3-8 times per day) for up to 35 days |
| 2. Active Comparator<br>One 0.3 mg tablet from Day 1 to 35 | Drug: Nicotine<br>Nicotine in oral formulation every time levodopa is administered to the subjects (~3-8 times per day) for up to 35 days |
| 3. Active Comparator<br>One 0.3 mg tablet from Day 1 to 7, One 1 mg tablet from Day 8 to 35 | Drug: Nicotine<br>Nicotine in oral formulation every time levodopa is administered to the subjects (~3-8 times per day) for up to 35 days |
| 4. Active Comparator<br>One 0.3 mg tablet from Day 1 to 7, One 1 mg tablet from Day 8 to 14, One 2 mg tablet from Day 15 to 21, One 1 mg and One 2 mg tablets from Day 21 to 35 | Drug: Nicotine<br>Nicotine in oral formulation every time levodopa is administered to the subjects (~3-8 times per day) for up to 35 days |
| 5. Active Comparator<br>One 0.3 mg tablet from Day 1 to 7, One 1 mg tablet from Day 8 to 14, One 2 mg tablet from Day 15 to 21, One 1 mg and One 2 mg tablets from Day 21 to 28, Two 2 mg tablets from Day 28 to day 35. | Drug: Nicotine<br>Nicotine in oral formulation every time levodopa is administered to the subjects (~3-8 times per day) for up to 35 days |

3. The method of claim 1 or 2 wherein the amount of nicotine is sufficient to reduce said dyskinesia at least about 30%.

4. The method of claim 1 or 2 wherein said dyskinesia is induced by a Parkinson's disease treatment.

5. The method of claim 1 or 2 wherein said dopaminergic agent comprises a dopamine precursor or a dopamine receptor agonist.

6. The method of claim 1 or 2 wherein said dopaminergic agent comprises levodopa, bromocriptine, pergolide, pramipexole, cabergoline, ropinirole, apomorphine or a combination thereof.

7. The method of claim 6 wherein said dopaminergic agent is levodopa.

8. The method of claim 1 or 2 wherein said subject suffers from Parkinson's disease.

9. The method of claim 1 or 2 wherein said administration comprises a single daily dose of nicotine.

10. The method of claim 1 or 2 wherein said administration comprises multiple daily doses of nicotine.

11. The method of claim 1 or 2 comprising administering at least one dose of nicotine in a 24-hour period, wherein said nicotine is present at about 6 milligrams or less per dose.

12. The method of claim 11 wherein said nicotine is present at about 4 milligrams or less per dose.

13. The method of claim 11 wherein said nicotine is present at about 2 milligrams or less per dose.

14. The method of claim 11 wherein said nicotine is present at about 1 milligrams or less per dose.

15. The method of claim 1 or 2 wherein said amount of nicotine administered in a 24-hour period is about 15 milligrams.

16. The method of claim 1 or 2 wherein said amount of nicotine administered in a 24-hour period is about 8 milligrams.

17. The method of claim 1 or 2 wherein said amount of nicotine administered in a 24-hour period is about 3 milligrams.

18. The method of claim 1 or 2 wherein the dopaminergic agent is being administered for the treatment of Parkinson's disease or Parkinsonism in the human and the effective amount of the dopaminergic agent is 100% to 75% of the effective amount when the dopaminergic agent is administered without the nicotine.

19. The method of claim 1 or 2 wherein said dopaminergic agent is being administered for the treatment of Parkinson's disease or Parkinsonism in the human and the amount of the dopaminergic agent administered is not reduced after nicotine administration.

20. The method of claim 1 or 2 wherein the human is suffering from said dopaminergic agent-induced dyskinesia.

21. The method of claim 1 wherein said amount of nicotine is maintained for a period of more than six months.

22. The method of claim 1 wherein said amount of nicotine is maintained for a period of more than one year.

* * * * *